US011357439B1

(12) United States Patent
Fischell et al.

(10) Patent No.: US 11,357,439 B1
(45) Date of Patent: Jun. 14, 2022

(54) ADVANCED CARDIOVASCULAR MONITORING SYSTEM WITH PERSONALIZED ST-SEGMENT THRESHOLDS

(71) Applicant: ANGEL MEDICAL SYSTEMS, INC., Eatontown, NJ (US)

(72) Inventors: David R. Fischell, Fair Haven, NJ (US); Michael Sasha John, Long Branch, NJ (US); David Keenan, Tinton Falls, NJ (US); Steve Johnson, Rochester, NY (US); Gregg Turi, Hackettstown, NJ (US)

(73) Assignee: ANGEL MEDICAL SYSTEMS INC., Eatontown, NJ (US)

( * ) Notice: Subject to any disclaimer, the term of this patent is extended or adjusted under 35 U.S.C. 154(b) by 0 days.

(21) Appl. No.: 17/304,675

(22) Filed: Jun. 24, 2021

Related U.S. Application Data

(60) Provisional application No. 62/705,397, filed on Jun. 25, 2020.

(51) Int. Cl.
| | |
|---|---|
| *A61B 5/00* | (2006.01) |
| *A61B 5/358* | (2021.01) |
| *A61B 5/366* | (2021.01) |
| *A61B 5/36* | (2021.01) |
| *A61B 5/283* | (2021.01) |
| *A61B 5/352* | (2021.01) |

(52) U.S. Cl.
CPC ............ *A61B 5/358* (2021.01); *A61B 5/0031* (2013.01); *A61B 5/283* (2021.01); *A61B 5/352* (2021.01); *A61B 5/36* (2021.01); *A61B 5/366* (2021.01); *A61B 5/7405* (2013.01); *A61B 5/746* (2013.01); *A61B 5/7455* (2013.01)

(58) Field of Classification Search
CPC ....... A61B 5/358; A61B 5/7405; A61B 5/366; A61B 5/7455; A61B 5/36; A61B 5/283; A61B 5/352; A61B 5/0031; A61B 5/746
See application file for complete search history.

(56) References Cited

U.S. PATENT DOCUMENTS

2009/0216141 A1* 8/2009 Fischell .................. A61B 5/413
600/509

\* cited by examiner

*Primary Examiner* — Scott M. Getzow

(57) ABSTRACT

A device for detecting acute coronary syndrome (ACS) events, arrythmias, heart rate abnormalities, medication problems such as non-compliance or ineffective amount or type of medication, and demand/supply related cardiac ischemia is disclosed. The device may have both implanted and external components and can communicate with other user devices such as smartphones and smartwatches for monitoring and alerting in response to detected medically relevant events or states of a patient. The processor is configured to provide event detection based upon various criteria including what is found to be statistically abnormal for a patient or what has been defined by a doctor to be abnormal. A patient's cardiovascular condition can be tracked over time using histogram, trend, and summary information related to heart rate and/or cardiac features such as those measured from the S-T segment of heartbeats. Heartbeats that are elevated but which are below what is defined as high, are used to provide medically relevant detections.

30 Claims, 22 Drawing Sheets

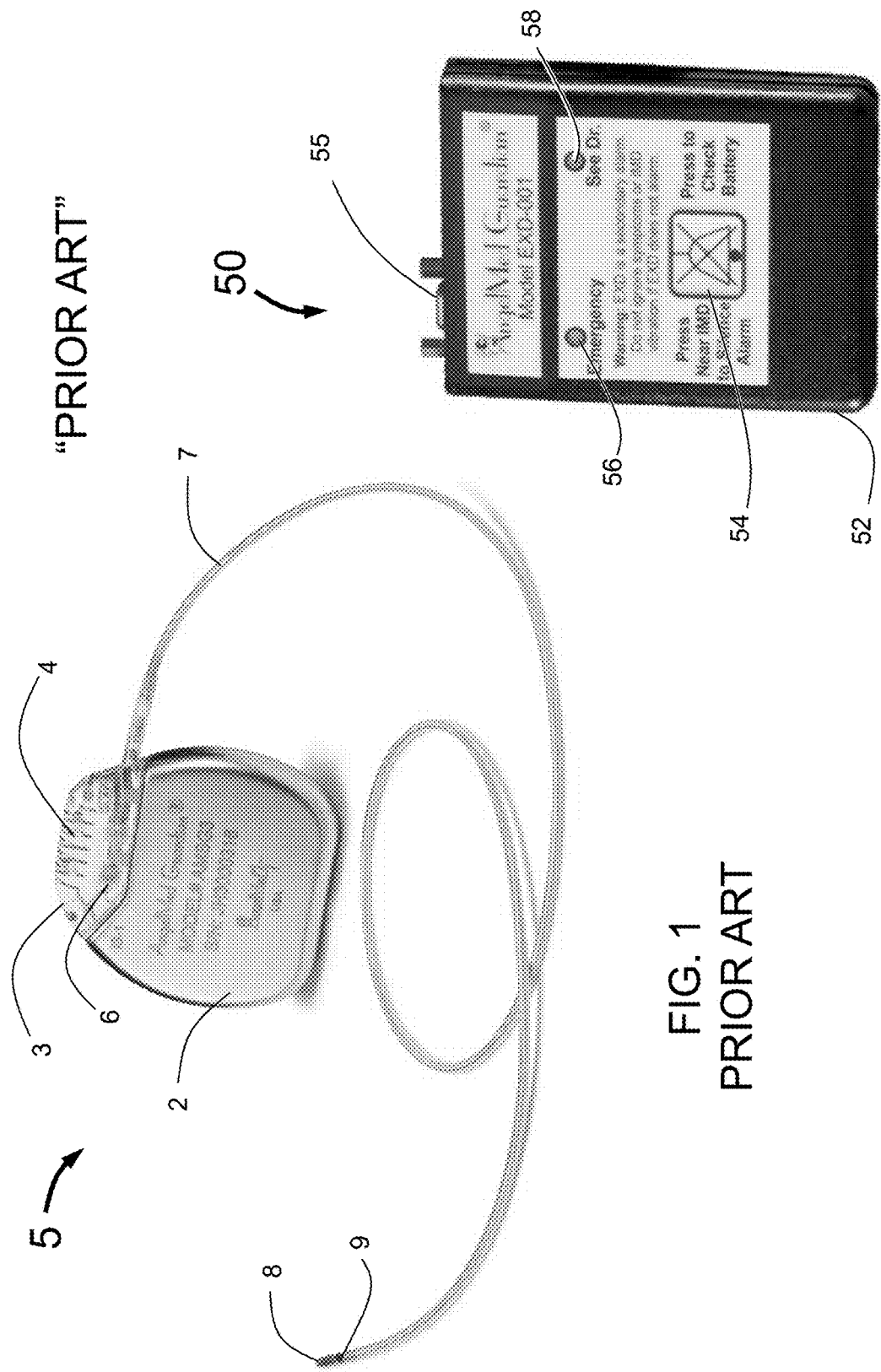

| Bin No. | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Number of Beats | | | | | | | | | | | | | | | | |
| R-R Interval range (sec.) | >1.2 | 1.09 | 1.00 | 0.92 | 0.86 | 0.80 | 0.75 | 0.71 | 0.67 | 0.60 | 0.55 | 0.50 | 0.46 | 0.43 | 0.33 | 0.33 |
| Heart Rate range (bpm) | <50 | 50-<55 | 55-<60 | 60-<65 | 65-<70 | 70-<75 | 75-<80 | 80-<85 | 85-<90 | 90-<100 | 100-<110 | 110-<120 | 120-<130 | 130-<140 | 140-<150 | >160 |

FIG. 11

ADVANCED CARDIOVASCULAR MONITORING SYSTEM WITH PERSONALIZED ST-SEGMENT THRESHOLDS

RELATED PATENT APPLICATIONS

This patent is based on U.S. Provisional App. No. 62/705,397 filed Jun. 25, 2020.

FIELD OF USE

This invention is in the field of systems that monitor, detect, or treat medical events and conditions of patient especially as related to cardiovascular health.

INCORPORATION BY REFERENCE

U.S. Pat. Nos. 6,112,116, 6,272,379, 6,609,023, 6,985,771, 7,107,096, 7,512,438, 7,558,623, 7,801,596, 7,844,323, 7,860,559, 8,002,701, 8,024,028, 8,038,624, 8,170,653, 8,244,338, 8,265,740, 8,512,257, 8,630,702, 8,655,434, 8,676,304, 8,838,215, 9,101,278, 9,468,383 and 9,788,739 are hereby collectively incorporated by reference.

U.S. Pat. Nos. 8,396,542, 8,406,862, 8,428,703, 8,427,704, 8,560,055, 8,682,422, 8,781,566, 9,031,644, 9,042,969, 9,375,151, 9,414,757 and 9,943,244 are hereby collectively incorporated by reference.

Prior Publications, Gibson et al, JACC 2019 vol. 73 No. 15, p 1919-1927; Holmes et al, JACC 2019 vol. 74, No. 16, 2019 p 2047-2055; and Kazmi et al. Medical Devices: Evidence and Research 2020 vol. 13 p. 1-12 are hereby collectively incorporated by reference.

BACKGROUND

Heart disease is the leading cause of death in the United States. A heart attack (also known as an acute myocardial infarction (AMI) typically results from a thrombus (i.e., a blood clot) that obstructs blood flow in one or more coronary arteries. AMI is a common and life-threatening complication of coronary artery disease. Myocardial ischemia is caused by an insufficiency of oxygen to the heart muscle. A blood clot totally blocking a coronary artery is often referred to as supply side ischemia as the oxygenated blood cannot get through the blockage. This differs from demand ischemia that is typically provoked by physical activity or other causes of increased heart rate when at least one coronary artery is narrowed by atherosclerosis.

Patients may experience chest discomfort (angina) when the heart muscle is experiencing either demand or supply side ischemia. Those with coronary atherosclerosis are at higher risk for AMI if the plaque becomes further obstructed by thrombus. Those patients who do not have any symptom of ischemia are said to have "silent ischemia" and if no symptoms are present during AMI it is referred to as a "Silent MI". Patents without ischemic symptoms have no warning to tell them to seek medical attention and are therefore at added risk of dying from AMI.

The current treatment for a coronary artery narrowing (a stenosis) is the insertion of a drug eluting stent such as the Xience® everolimus-eluting stent from Abbott Corporation. The insertion of a stent into a stenosed coronary artery is the most reliable medical treatment to eliminate or reduce coronary ischemia and to prevent the complete blockage of a coronary artery and AMI.

Acute myocardial infarction and ischemia may be detected from a patient's electrocardiogram (ECG) by noting an ST segment shift (i.e., voltage change) starting immediately or within a relatively short (less than 5 minutes) period after significant blockage of a coronary artery. However, without the benefit of knowing the patient's normal ECG pattern (i.e., baseline) for comparative purposes, detection from a standard 12 lead ECG can be unreliable.

Prior art does not disclose collecting and storing, in histogram and other formats, certain heart rate measures that can be valuable to the long-term management of cardiac disease patients.

Prior art subcutaneous loop recorders such as the Abbott Confirm and Medtronic Reveal® utilize two case electrodes spaced 4-6 cm apart to sense heart signal data. Data recording can be triggered automatically when arrhythmias are detected or upon patient "event tagging" using an external device. Loop recorders store subcutaneous ECG data but cannot measure ST segment changes accurately to detect heart attacks. Both high pass filtering and electrode spacing used by loop recorders preclude accurate detection of low frequency measurements of a heart's electrical signal which are needed for detection of ischemia using ST-segment measures.

Pacemakers can track the numbers of paced and not-paced beats. While pacemaker programmers can display the heartbeat data in histogram format, pacemakers do not generate and then operate upon histogram data for various heart signal parameters related to the electrogram waveform. While pacemakers track pacemaker operation, they do not measure or compute heart signal parameter histograms.

Prior art discloses classifying heart rate with respect to a "Normal" range and a "High" heart rate threshold above which tachycardia is present in the patient. Heart rates in the normal range are classified as "Normal." For example, in many patients' normal heart rates when the patient is not exercising or exerting themselves might lie in a range from 50 BPM to 90 BPM. Heart rates below the normal range are classified as "Low." Heart rates above the high heart rate threshold are classified as "High" and heart rates between the upper end of Normal and the High heart rate threshold are classified as "Elevated." Each of these heart rate ranges can have a lower and upper limit that is defined by a doctor (or an algorithm of the device) based upon assessment of the distribution of heart rates seen in the patient (shown graphically or statistically) over a sample period, or can be set in the device using default heart rate ranges that are defined based upon a sample population.

The prior art does not provide for further granularity in the "Normal" range to provide additional advantages. For example, the known prior art only discloses an ST detection algorithm with a single Normal heart rate range for triggering an Emergency alarm. This limitation might allow demand ischemia in the upper range of the defined Normal heart rate range to trigger a false positive Emergency alarm which may have the effect of incorrectly indicating an ACS event including AMI. Simply lowering the upper limit of the Normal range should reduce false positive risk, however it may increase the risk of not detecting an actual ACS event.

Cardiovascular disease (CVD) patients often use beta-blockers or drugs to promote normal rate and rhythm (e.g., prevent elevated heart rate) and avoid unnecessary strain of the heart. Patient non-compliance and/or difficulty with correct dosing increases risk for extended periods of elevated heart rate. Long-term monitoring of patient heart rate using histogram, trend analysis, and/or summary statistics provides value in CVD patients, however such is not addressed in the prior art.

U.S. Pat. No. 6,609,023 ('023) discloses algorithm logic and steps for detection of ischemic events, High, Low and Elevated heart rates. Elevated heart rates are processed by ischemia subroutine 480 of FIG. 10 ('023) which is called by the primary algorithm loop 450 of FIG. 5 ('023). The process 480 identifies ST-segment changes at Elevated heart rate that may be indicative of a partial coronary blockage similar to that seen in a failed stress test. Neither the main loop 450 nor the subroutine 480 of ('023) disclose detecting extended periods (e.g., hours) of elevated heart-rate possibly reflective of beta-blocker non-compliance or incorrect dosing. The '023 system and method is devoid of subject matter associated with detecting (and alerting to) extended periods of elevated heart rate.

U.S. Pat. No. 9,468,383 ('383) in FIG. 16 discloses communication options from an External Alarm Transceiver that can receive alerts and upload data from an IMD and then transmits the data locally to commonly referred to smart devices such as smartphones, tablets, physician's programmers or through long distance voice/data communication interfaces to a remote diagnostic center with wireless protocols such as Wi-Fi and/or Bluetooth protocols being used.

Prior art medical devices, for example, many pacemakers, loop recorders and ICDs stop working when they reach end of life without directly warning the patient. While some of these devices use telemetry to identify battery issues such as end-of-life, there is a long felt need for providing differing and detailed systems and methods to provide notification of implanted device impending end of life.

Prior art Pacemakers have used a magnet-activated-relays to initiate a programming session but this lacks security in the current environment where computer hacking is a common occurrence. Thus, there has arisen the need for a secure way to actuate or wake up an implant for programming that is not dependent on use of a magnet or a power draining wireless transceiver of the system remaining active over extended periods of time.

The '023 U.S. Patent discloses wireless communication over 1-3 meters with an EXD having circuitry that allows the patient to abort i.e., "silence" an alarm. In such prior art systems, an "alarm-off" button and related circuitry halts an alarm activated in the EXD or IMD or both. Patient acknowledgement of the alarm using the alarm silence action provides the IMD with timing of patient confirmation which may then lead to contingent provision of further alarming actions. However, such prior art systems do not provide for inadvertent deactivation of the system alarm (e.g., accidently sitting on the alarm button) which could result in a missed alarm. Further, such prior art systems, such as that disclosed in U.S. Pat. No. '023 disclose a reminder alarm that occurs if the alarm is not silenced by patient within a defined time interval. Such prior art systems do not disclose the provision of reminder alarms at one or more times after the patient has silenced an initial alarm. Thus, there is the need for a system where inadvertent deactivation of the system and continued reminder alarms are provided subsequent to the patient silencing an initial alarm.

Use of a vibrator motor in an IMD and/or the EXD, and in particular brushed vibrator motors, is an effective method to alert a patient. Unfortunately, such miniature motors with an off-center weight to produce the vibration may malfunction if not in use on a regular basis, thus there is the need for the incorporation of an alternative vibrator such as a linear resonant actuator which is not seen or disclosed in the prior art systems.

Prior art systems and methods in general, do not disclose an IMD and physician's programmer software and circuitry to adjust the intensity of vibrational alerting so that alarms are easily recognized but are not painful to the patient.

The AngelMed Guardian® underwent a pivotal ALERTS study with results that have been published in three articles incorporated by reference herein: Gibson et al, JACC 2019 vol. 73 No. 15, p 1919-1927; Holmes et al, JACC 2019 vol. 74, No. 16, 2019 p 2047-2055; and Kazmi et al. Medical Devices: Evidence and Research 2020 vol. 13 p. 1-12.

Prior art non-invasive glucose monitors use optical sensors to sense glucose levels for enhanced control of insulin injection levels but have not been incorporated in a cardiac monitor nor have they been applied to a dual-level alerting system such as that disclosed in the AngelMed Guardian®. Since diabetes is a risk factor for ACS events, it would be advantageous to provide additional specified alerting capabilities not disclosed in the prior art. For example, alerting of a patient could be defined for the IMD and/or EXD if a patient's glucose levels became unstable (e.g., changed too quickly) or dropped to a selected level that was defined as dangerous for the patient. In this manner, the ACS event detector of the subject system and method serves to provide a safety net for diabetic patients that could support their self-care by providing an alert to a potential serious medical event related to diabetes.

SUMMARY OF THE INVENTION

The present invention Advanced Cardiovascular Monitoring System (ACMS) provides cardiac monitoring and alerting features which are advantageous over those described in prior art references.

In some embodiments, the present invention is realized in medical devices that are devoid of any means to apply electrical energy to the heart or electrically stimulate the heart. As such, these embodiments cannot pace, cardiovert or defibrillate the heart.

The ACMS would include the following system components:

A) a Heart Signal Capture and Event Detection (HSCED) device with the capability to sample signals related to a patient's heart activity and detect cardiac events and realized as one of, or a combination of, an Implanted Medical Device (IMD), Subcutaneous Cardiac Monitor (SCM) or Skin Surface Medical Device (SSMD). The HSCED may also include software and hardware that enables alerting of the patient, caregivers, and/or medical personnel. Although the ACMS may provide urgent Emergency Alarms or "alarms" and less urgent See Doctor alerts or "alerts", the terms "alarm" and "alerts" can be used interchangeably to indicate a notification that is provided by the system as part of a patient's health monitoring and/or treatment, and B) an External alarm or alerting Device (EXD) with wireless connectivity to the IMD and cellular data connectivity with optional voice connectivity to a cloud server. Capabilities described herein for an IMD and EXD are applicable to any HSCED device. The capabilities described herein may be incorporated into patient worn automated external defibrillator (AED) systems (e.g., Zoll Life Vest). For non-implantable monitors like the SSMD, the EXD function can be integrated within the SSMD. In embodiments, the EXD may be realized using a patient's smartphone or by EXD communication with a smartphone.

C) an ACMS physician's programmer for setting the operational parameters for cardiac event detection and uploading data collected from the IMD, SCM or SSMD.

In embodiments, additional components of the ACMS include:

A) a HIPPA compliant External Support System (ESS) designed to securely receive and store data from the EXD;
B) a Smart Device APP (SDAPP) that provides data access to the data and alerts collected by the IMD on a smart device such as a smartphone, home base station, tablet or PC. More than one version of the SDAPP can be tailored for different users including: the patient, a caregiver, paramedics and EMS, Emergency Room (ER) personnel and physicians including GPs and cardiologists; and,
C) Other medical sensors of the AMCS are configured to sense data about the patient.

In embodiments, the ACMS capabilities and features include the use of histograms to efficiently store and analyze data to derive and display the distribution of ST-shift levels (or other ST-segment measure) as disclosed in U.S. Pat. Nos. 7,512,438, 8,024,028, 8,244,430 and 9,005,130. These are used by the ACMS physician's programmer to calculate positive and negative ischemia detection thresholds for detection of excessive ST shift. The threshold calculations are based on statistical calculations including the mean, median and variability of the distribution (e.g., standard deviations) in one Normal and one or more Elevated heart rate ranges. For example, the portion of heart rates between the upper limit of the normal heart rate range and a high heart rate threshold may include a single heart rate range or be sub-divided into a multiplicity of heart rate ranges. In one embodiment 4 of these sub-divided heart rate ranges could be programmed in the ACMS. These may be set manually or be automatically created by the ACMS based on a sub-division algorithm that sub-divides the range of heart rates between the upper limit of the normal range and the high heart rate threshold.

In embodiments, the present invention enhances this patient self-referenced excessive ST shift detection threshold setting mechanism by:

1. Separately computing, the positive and negative variability used to define the normal range of a patient's ST-segment deviation (ST level relative to another portion of the heart signal, e.g., a portion between the P and Q wave). This includes, for example, the use of histograms for storage of the ST deviation measurements.
2. Utilizing a selected number of standard deviations (e.g., 3 standard deviations) from the mean, median or zero value for ST deviation to determine positive and negative thresholds for detecting excessive ST shift (ST deviation compared to a baseline normalized to an average heart signal amplitude), with a preferred embodiment using three standard deviations.
3. Using a method that is suitable for calculating standard deviations for asymmetric ST deviation distributions. Specifically, one method "mirrors" the positive portion above a center point of the distribution to calculate the positive standard deviation while the negative distribution of ST-shift values are replaced by a mirror of the positive distribution to create a symmetrical distribution-relative to a center point. This is then used for calculating a positive ST deviation threshold (using a multiple of the positive standard deviation, e.g., 3 standard-deviations). Similarly, the method replaces the positive portion of the distribution with a mirror of the negative portion of the distribution to calculate a negative standard deviation with respect to a center point. This is then used for calculating a negative ST deviation threshold (using a multiple of the negative standard deviation, e.g., 3 standard-deviations). The center point can be the mean or median of the distribution or in a preferred embodiment, a zero value of ST deviation as the center point. This technique is the only one needed for the present invention as it will also work for both symmetric and asymmetric distributions of ST-segment levels.
4. The positive and negative excessive ST shift detection thresholds then used by the ACMS monitor are then set by normalizing the positive and negative ST deviation thresholds determined by beats analyzed over a data collection time period to an average value of heart signal amplitude over a similar data collection time period.
5. Acute adjustment of the ST-shift thresholds can also be made using a correction factor that is based upon the patient's recent history of variability as a function of time of day or other variable that characterizes a particular patient's heart rhythm profile (e.g., postural effects). For example, a correction factor may be used to slightly increase or decrease the ST-shift threshold (or other measure of ischemia relied upon by the ACMS) based upon whether a clock time indicates it is morning, afternoon, or night, based upon body angle, or other variable.

In embodiments, the system includes alerting for detection of extended periods of elevated heart rate above threshold rate and duration criteria which may be indicative of patient beta blocker non-compliance or improper beta blocker dosing.

In embodiments, the system includes at least two different methods to determine when the battery is nearing end of service (EOS) and determine an appropriate time before EOS to provide patient alerting in advance of the EOS to allow time for the patient to arrange for a device replacement.

In embodiments, a multi-range wireless communication system is realized by the EXD, ACMS physician's programmer, or other system component to provide near-field (<0.1 meter), mid-field (0.1 to 25 meters), and far-field (>25 meters) communication and is configured for providing features and methods including:

1. Rather than being continuously active, near-field triggering is used to activate longer-range communication circuitry to reduce power use;
2. A near-field mechanism that allows a user to silence alarms is configured to prevent a patient from accidentally depressing a "silence alarm" button on an EXD. This may be realized by an operational contingency requirement such as requiring a pattern of button presses [3 button presses about one-second each] to be provided sequentially within 5 a second interval.
3. A communication error signal indicating lack of response such as may occur if the EXD is held outside of the near-field range and when the Alarm Silence button is depressed (e.g., if the IMD does not respond then a single beep could be provided by the EXD and/or a message of communication error could be displayed).
4. A unique patient notification signal produced by an EXD to verify the proper functioning of the IMD. For example, the EXD is held in close (near-field) proximity to the IMD and a button such as the alarm silence button on the EXD is depressed. If the IMD is not functioning and the EXD alarm silence button is depressed, a single beep would be provided by the EXD and/or a message of communication error could be displayed. If the IMD is functioning properly and the button is pressed with the EXD in the near-field of the IMD, this would initiate a mid-field communication session between the IMD and EXD and the EXD would deliver two beeps and/or a message about device status could be displayed. This feature enables the patient, caregiver or medical practitioner to verify the IMD is active, and the telemetry communication is working. It is also envisioned the IMD would include additional status data (e.g., IMD battery status, device status/error register, recordings count and clock count) in its transmission to the EXD additional status data including IMD battery status, device status/error register, recordings count and clock count.

In embodiments, the ACMS may include reminders or notifications defined for alerting the patient which are related to an alert, due to a time of day or tied to an event. Reminders can be provided by the IMD, EXD, or through a message or notification to the patient's phone, tablet or PC. Reminders can be a text message and/or spoken message. Examples include:

1. Reminders to take medications including:
   a. A reminder to chew an aspirin or consume medication after an Emergency Alarm;
   b. A non-compliance notification suggesting that the patient may have skipped their beta blocker medications following alerts for High or extended Elevated heart rate;
2. A reminder to perform a task due to a patient notification (e.g., 2 or 3 days after a See Doctor alert has occurred the patient is reminded that a doctor appointment should have been scheduled); and,
3. Reminders to perform daily exercise or other behaviors that promote good heart health.

In embodiments, the ACMS detects the occurrence of an event defined as requiring notification. The ACMS provides a first alarm to notify the patient. If defined for the event, then at least one additional reminder alarm is provided at a preset delay after either a) the initial alarm or b) the patient acknowledgment/silencing of the initial alarm using the EXD. The attributes for the reminder alarm are defined as a function of the alerted event type and may be provided by the EXD, the IMD, and/or other ACMS system component. If the EXD provides the reminder alarm then the EXD can be programmed to provide this without requiring the IMD to send another alert trigger to the EXD (to save power). Further, reminder alarms can be defined contingently. For example, if a patient does not silence the initial alarm then the reminder alarm can occur after a shorter amount of time and at a louder intensity (than the initial alarm or than an alarm that occurs after patient confirmation). Reminder alarms can also be silenced. It is important to recognize the value of patient acknowledgement of alarms in the long-term management of high-risk patients in a home or ambulatory environment. While the prior art describes reminders if the patient does not acknowledge/silence the alarm, reminder alarms are also useful in situations such as when a subject silence the initial alarm that wakes them from sleep, while decreasing the risk of falling back asleep without taking action. Accordingly, even when an alarm silence button is pressed, providing at least one additional reminder alarm provides an advantage. Additionally, the EXD is provided with an alarm module that is configurable by the patient or doctor to increase the number of reminder alarms that will occur in addition to the first alarm. Further, when a bedside monitor or an EXD is provided which communicates with a remote center, then a remote telemedicine session may be defined to occur as part of the reminder alarm.

In embodiments, the EXD is configurable to respond to communication signals emitted by a single IMD to which it is paired. The EXD and IMD pairing can occur during initial programming session with instructions from the programmer, or the EXD itself could allow a user to place it into a "pairing mode" that is provided by its communication module which enables it to pair with a unique IMD. During an actual alarm event, the IMD communicates a signal which may be detected by an EXD, but the EXD will not alert unless the handshaking routine indicates the IMD signal is from its "paired" IMD. Additionally, in certain situations (when two patients live together) it may be advantageous to allow the EXD to be paired to more than 1 IMD, or to be toggled to operate in a mode where it will alert if any IMD in its vicinity sends an alert signal. While this may be helpful when two family members are both patients with IMDs (since it decreases the risk of an alarm unintentionally being ignored), allowing EXDs to respond to any IMD may cause confusion or other problem when used in public areas where two strangers may be in proximity to each other upon the triggering of an alarm. The EXD may also use geolocation or other methods of determining location (detection of a wifi network of a patient's home) to determine if a user is located in their house or other environment and can alter the alerting methods based upon the patient's location.

In an embodiment, the EXD is also configurable to provide different notifications at pre-defined intervals. For example, an EXD communication module may be configured to send a text message to a defined contact (e.g., family member) upon receipt of an alarm from the IMD, or after a delay of for example, 15 minutes, so that the patient is not contacted by a concerned family member prior to calling for an ambulance (e.g., 911).

In embodiments, the present invention ACMS also includes means to activate training alarms to allow patients to experience and practice using the EXD to silence alarms and alerts including:

1. IMD alarm selection software of the ACMS physician's programmer to increase or decrease the intensity of the vibration delivered by the vibrator of the IMD for patient alarms. The ACMS programmer can activate training alarms at different levels to obtain patient feedback and then can operate to program the intensity level(s) for actual alerts provided during treatment.
2. EXD alarm selection software of the ACMS physician's programmer to increase or decrease the intensity of the EXD acoustic alert to be sure the patient can hear it, and EXD vibration alert if also provided. In addition to the acoustic intensity being adjustable, for example from about 70 dB to 120 dB, the frequency can be modifiable to address patients with low or high frequency hearing loss. Additionally, the tones can include 2 or more alternating frequencies such as 1000 Hz and 2000 Hz to increase the likelihood of the tone being outside of frequency range of hearing loss.
3. physician's programmer software which enables adjusting of the pattern or content of one or more types of patient alert to make it more detectable by the patient in various manners. For example, patients are more likely to attend to their own name or voice instead of simply tones. The patient (or a caretaker or family member) can record their own name into the EXD which can be played back to them during an alert or may be presented only they fail to press the alarm silence button.
4. Allowing the patient to use the EXD during training alarms to teach the patient how to properly silence an alarm.

In embodiments, the ACMS includes features that enhance differentiation between ST changes due to coronary occlusion at a normal resting heart rate and ST-changes due to demand ischemia:
1. Additional histograms bins that collect data on the distribution of ST Shift levels in a subset of beats that lie within the "Normal" heart rate range but are within a higher portion of the normal range. Instead of a single Normal heart rate range histogram for calculating ST detection thresholds, two (or more) histograms are defined to cover the normal range. These would be a Low-Normal histogram and High-Normal histogram that would be used to calculate the respective positive and negative thresholds for the respective range.
2. For beats with RR intervals in the high-normal range the ischemia detection would require an increased number of shifted beats or increased interval of excessive ST shift to trigger an Emergency alarm.
3. Demand ischemia ST shifts recorded by the IMD (with a can-to-tip vector), are negative. Added processing as described in 1. or 2. above, can be set to occur for both positive and negative shifts, or can only be defined for excessive ST shifts beyond a negative threshold within a high-normal range.

In embodiments, the ACMS includes features that enhance differentiation between ST changes due to coronary occlusion and ST-changes due to demand ischemia:
1. Adding additional histograms to collect data on the distribution of ST Shift levels in a subset of beats that lie within the "Normal" heart rate range but are within a higher heart rate portion of the normal range. These can be used to create a "High-normal" ST threshold for detecting an occlusive event.
2. For beats with RR intervals in the high-normal range the ischemia detection rule requires an increased number of required beats or increased time period of excessive ST shift that must occur before triggering an Emergency alarm for an occlusive event.
3. In some patients, demand ischemia ST shifts recorded by the IMD (with a can-to-tip vector), may be negative. The present invention contemplates that the added processing as described in 1. or 2. above, will only occur to identify excessive ST shifts beyond a negative threshold within a high-normal range.

In embodiments, additional features are incorporated into the EXD including:
1. a rechargeable battery with optional inductive recharging realized using a bedside stand that allows patients to keep an EXD with a rechargeable battery refreshed;
2. a wristwatch form factor that includes a vibrator and a vibration-only mode to address privacy concerns and a sonic alarm that for privacy concerns may use the same sound as a phone call, or other sound selected by a user. The EXD is realized as, or communicates with, a software module or APP of a commercially available or custom built smart-watch or other wrist-worn accessory (e.g., health tracker);
3. wireless circuitry to enable cellular, Bluetooth or other wireless data transmission to another device with cellular connectivity that allows HIPPA compliant cloud storage, data transmission, processing, and alerting, with a remote center or medical practitioner. This can include data capabilities to upload to a cloud server External Support System (ESS) designed to securely send and receive data from the EXD collected by the IMD, EXD, or from sensors and associated with a cardiac event or with monitoring a cardiovascular condition of a patient;
4. a real time clock with or without the ability for wireless time synchronization, to provide for local or international time-stamping of detected events and saved heart signal parameter data;
5. standardized local wireless connectivity (for example: Bluetooth) to the IMD or to allow the EXD to communicate wirelessly with a local Smart Device such as a Smartphone, Tablet or PC running an APP allowing both local alerting and communication with the IMD and data communication through the cloud with external equipment and personnel;
6. capability to verify its status and IMD status using distinct acoustic and/or visual signals provided in response to a button push on the EXD when it is held outside of or placed within the near-field range of the IMD; and
7. Wireless connectivity to sensors for monitoring of: Body temperature and blood pressure; Glucose level and oxygen saturation such as by using optical sensing methods; Fatty acid Binding Protein 3 (FRBP3), CPK and/or Troponin which are indicators of a heart attack.

In embodiments, the ACMS provides additional histogram format data storage to that described in the prior art. The ACMS uses histograms to track ST levels and also uses histograms to track measures such as glucose levels, temperature, blood pressure and/or patient activity such as heart signal parameters including: R-R interval variability, R peak height; R wave width; QRS voltage; QRS width; RS width; T wave width and/or amplitude; and T wave alternans.

Histogram data can be analyzed by IMD, the EXD and/or the patient's physician using analysis tools in the physician's programmer or SDAPP that may include 3D and/or surface plots. Storage can be based on data collection on a sub-hourly, hourly, daily, weekly, monthly and for periods longer than a month.

Tracking patient heart rate (or RR Interval) over long periods of time is an important capability for the ACMS. These data can be used for allowing better medication management and may include pre-set detection thresholds to identify abnormal heart function.

Additional sensor capabilities in the IMD or that can communicate with the IMD and/or EXD include: Glucose monitoring; temperature monitoring; blood pressure monitoring; accelerometer monitoring to monitor patient activity including exercise, falls or the patient lying down; and sound monitoring via microphone.

It is envisioned that the ACMS could include a streaming data mode where data sensed by the IMD is directly transmitted in segments or continuously to allow patient local or remote monitoring. The data may include ECG, electrogram or other heart signal data as well as any other telemetry sensed by the ACMS.

As the aforementioned features have indicated, the features of present invention allow for improved patient medical monitoring and care which are realized as a number of objects of the invention.

An object of the present invention is to separately determine positive and negative excessive ST shift detection thresholds by separate statistical analysis of ST shift histograms of positive and negative distributions.

Another object relates to processing asymmetric distributions of ST histograms to set positive and negative detection thresholds and comprises mirroring of the positive portion of the ST distribution to calculate the positive standard deviation and mirroring of the negative portion of the ST distribution to calculate the negative standard deviation.

Another object is to multiply the positive and negative ischemia detection thresholds by adjustment coefficients that are based upon positive and negative distributions for an individual or a suitable population value (e.g., matched demographically).

Another object is to use at least one of a different number of standard deviations for positive and negative ischemia detection thresholds, or a different minimum interval across which the ST-measure must be exceeded, or both.

Another object is to set the positive and negative excessive ST shift detection thresholds at the zero value, mean (or median) plus or minus 2 or more standard deviations.

Another object is to set the positive excessive ST shift detection threshold at the zero value, mean (or median) plus a multiple of 2 or more of the positive standard deviation.

Another object is to set the negative excessive ST shift detection threshold at the zero value, mean (or median) minus a multiple of 2 or more times the negative standard deviations.

Still another object is to provide an ACMS including an IMD designed to alert the patient to extended periods of elevated heart rate or shortened R-R interval to facilitate dosing and compliance of beta blocker or other medications that influence heart rate.

Still another object is to provide an ACMS with at least two methods of determining battery end of service (EOS) and means to alert the patient when either of the two methods indicates that the battery capacity is close to being exhausted.

Still another object is to provide an ACMS where patient alerts for the need for battery replacement are triggered at an Effective Replacement Indicator (ERI) which occurs before battery EOS.

Still another object is to provide the ERI set to occur at least 30 days before end of battery service leaving sufficient energy for at least one additional alert by the IMD.

Still another object is to provide a cumulative energy usage tracking capability in the ACMS where functions and states are given a unique integer unit to simplify tracking.

Still another object is to provide one of the two methods of determining battery end of life which is a battery voltage measurement under applied load.

Still another object is to provide the load used for battery measurement by turning on the vibrator or wireless radio transceiver.

Still another object is to have wireless communication capability in the IMD that can operate over two ranges including a near-field close proximity range of less than 0.1 meter from the implant and a longer range on the order of 1 or more meters.

Still another object is to require alarm silencing from an External alarm or alerting device (EXD) only operated in the near-field.

Still another object is to provide an EXD that can be used to verify its status as well as that of the IMD by use of unique acoustic and/or visual signals provided in response to a button push on the EXD when it is held outside of or placed within the near-field range of the IMD.

Still another object is to provide an ACMS that can provide an appropriate additional reminder for the patient to perform a pre-specified task that may include taking a pre-specified medication.

Still another object is to require initiation of a programming session begin with a command to the IMD that uses the near-field communication capability.

Still another object is to provide at least one reminder alarm following patient acknowledgement of a first alarm at a preset delay of more than 5 minutes after the first alarm.

Yet another object is to provide the ability of the ACMS to activate training alarms to allow patients to experience and practice using the ACMS EXD to silence alarms and alerts.

Yet another object is to have the ability of the ACMS to activate vibrational and/or acoustic training alarms at 2 or more different intensities and/or patterns.

Yet another object is to provide additional capabilities to differentiate an occlusive transmural ischemic event from demand ischemia.

Yet another object is to provide an EXD with one or more additional features including: Capability to verify EXD and IMD functionality; Vibrational alerting capability; A rechargeable battery; Incorporation into a wearable including a wrist worn device such as a smart watch; Incorporation of cellular data and/or voice capability; A real time clock that can be synchronized to local time using wireless communication for improved time stamping of events; Incorporation of Bluetooth, Wi-Fi or other local wireless connectivity to allow pairing with a smart device including methods to do so at the time of ACMS programming; Connectivity to sensors for monitoring of parameters including temperature, blood pressure, Oxygen saturation, Glucose level and MI related enzymes.

Yet another object is to provide two or more versions of the Smart APP for smartphone, tablet or PC to optimize for different uses including: the patient, a caregiver, paramedics and EMS, Emergency Room (ER) personnel and physicians including GPs and cardiologists.

Yet another object is to utilize histogram format data collection and storage for the tracking of heart signal parameters and non-cardiac sensed data including an ACMS physician's programmer and/or SDAPP that can display 3D surface diagrams of histogram data.

Yet another object is to provide an IMD capable of tracking heart rate/RR interval data for long term patient health monitoring including pre-set detection thresholds.

Yet another object is to provide the ACMS IMD with sensors for monitoring a patient's health.

Yet another object is to provide a real-time electrogram streaming to a SDAPP on a PC, tablet or smartphone.

Still another object is to enhance IMD reliability through use of: Periodic exercising of a brushed vibrator motor; Use of a linear resonant actuator to provide vibrational alerts; Use of a Lithium Carbon Mono-Fluoride (CFx) chemistry battery.

These and other objects and advantages of the disclosed invention will become obvious to a person of ordinary skill in this art upon reading of the detailed description of this invention including the associated drawings and claims as presented herein.

BRIEF DESCRIPTION OF THE DRAWINGS

FIG. 1 is a schematic view of the prior art AngelMed Guardian IMD showing the IMD body (or "can"), header, and lead.

FIG. 2 is a schematic view of the prior art AngelMed Guardian EXD.

FIG. 11 is a table showing the structure of the R-R interval/heart rate histogram data memory for a single data collection time period.

DETAILED DESCRIPTION OF THE INVENTION

Figure 3:
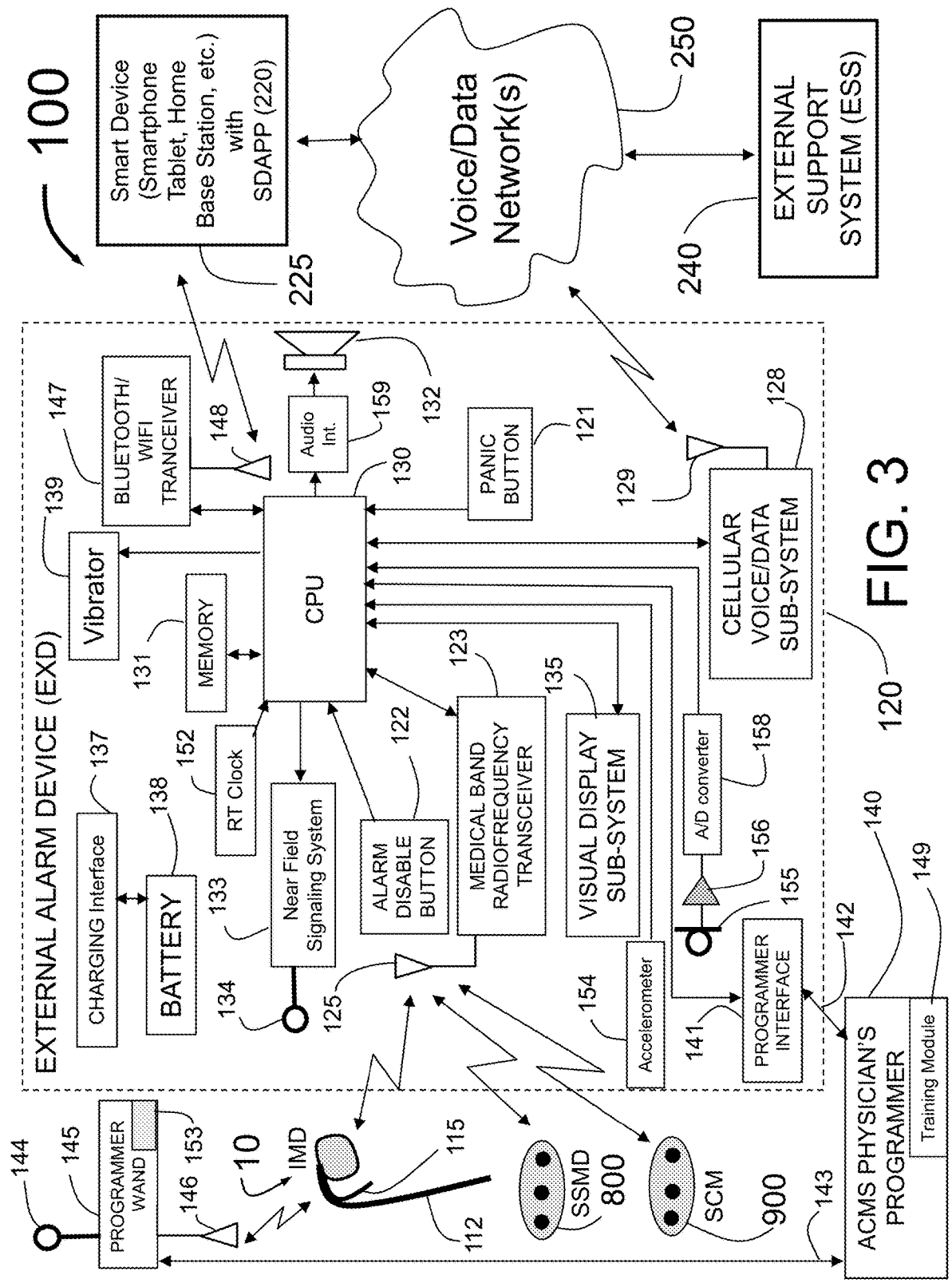
FIG. 3 is a block diagram of the present invention ACMS with its EXD, showing how the EXD connects wirelessly to the IMD, Subcutaneous Cardiac Monitor (SCM), Skin Surface Monitoring Device (SSMD) and to the External Support System (ESS) accessed by a Smart Device APP (SDAPP).

When masculine pronouns "he" and "his" are used herein, the patient or medical practitioner may be a man or a woman.

The term "medical practitioner" is used herein to mean any person involved in the medical treatment of a patient. Such a medical practitioner would include, but is not limited to, a medical doctor (e.g., a general practice physician, an internist or a cardiologist), a medical technician, a paramedic, a nurse or an electrogram analyst.

The term "cardiac event" includes an acute myocardial infarction, ischemia caused by effort (such as exercise) and/or an elevated heart rate, bradycardia, tachycardia or an arrhythmia such as atrial fibrillation, atrial flutter, ventricular fibrillation, premature ventricular contractions or premature atrial contractions (PVCs or PACs) and the rejection of a transplanted heart.

The term "electrocardiogram" (ECG) is understood to be the heart's electrical signal. This may be sensed through subcutaneous or skin surface electrodes that are placed in a position to indicate the heart's electrical activity. An ECG segment refers to ECG data for either a specific length of time, such as 10 seconds, or a specific number of heart beats, such as 10 beats. For the purposes of this specification, the PQ segment of a patient's ECG is the typically flat segment of a beat of an ECG that occurs just before the Q and R waves. For the purposes of this specification the ST segment of a patient's ECG is that segment of a beat of an ECG that occurs just after the S wave.

Although often described herein as an electrocardiogram (ECG), the electrical signal from the heart as measured from electrodes within the heart is may more properly be termed an "electrogram" or intra-myocardial electrogram (IMEG). An "electrogram segment" refers to a recording of electrogram data for either a specific length of time, such as 10 seconds, or a specific number of heart beats, such as 10 beats. The terms ECG, electrogram, and IMEG may be used interchangeably herein.

For the purposes of this specification, the term QRS voltage is defined as a measure of QRS complex voltage amplitude which may either be measured from Q to R, or S to R of a beat of the ECG. The term QRS segment or QRS complex is that segment of the electrogram from the Q through the R and ending at the J point of the S wave. The terms "detection" and "identification" of a cardiac event have the same meaning. A beat is defined as a sub-segment of an ECG segment which covers the electrical signal from the heart for exactly one beat of the heart and includes exactly one R wave. If the heart rate is 60 bpm, then the sub-segment of the electrogram that is exactly one beat would represent a sub-segment of the electrogram that is exactly 1.0 second in duration. For the purposes of this invention, the term "average value", "average amplitude" or "average voltage" of any segment (viz., QRS complex, ST segment or PQ segment) of the electrogram shall be defined as meaning either the mean or the median of a multiplicity of measurements of that segment. It is also envisioned that in some cases both mean, and median may be computed and will on occasion be described separately herein.

"Heart signal parameters" are defined to be any measured or calculated value created during the processing of one or more beats of ECG/electrogram data. Heart signal parameters are features of the electrogram derived from one or more measured values and include PQ segment average voltage, ST segment average voltage, R wave peak voltage, ST deviation (ST segment average voltage minus PQ segment average voltage), ST shift (ST deviation compared to a baseline average ST deviation from heart signal data collected at some prior time normalized to an averaged heart signal amplitude), average signal strength, T wave peak height, T wave average voltage, T wave deviation, QRS complex width, QRS voltage, heart rate and R-R interval. Counts of the number of arrhythmia related events such as PACs, PVCs and/or episodes of atrial fibrillation are not considered herein to be heart signal parameters as they do not directly result from a measured value derived from a beat of the electrogram. ST segment related heart signal parameters include, ST segment average voltage, ST deviation, ST shift and ST Shift % which is ST-Shift normalized to an average heart signal amplitude (e.g., QRS amplitude or R-wave amplitude/height.

The term "data collection time period" should be understood to generally mean the time during which the IMD will be updating a histogram and/or computing an average value of heart signal amplitude from a multiplicity of beats. The data collection period could be as short as a minute and as long as many months. Ideally, a data collection time period of 6 to 24 hours would provide important information and would minimize effects from daily cycles.

The "collected data retention time period" should be generally understood to be the period over which data retained in the IMD such as average heart signal amplitude, histograms or histogram sets are stored in IMD memory before it is overwritten with new data. For example, if the data collection time period is one day, there are 5 histograms for 5 different heart rate ranges collected each day and there are 8 sets of histogram memory (each corresponding to a day), then one set will be the current day with histogram stored from the 7 previous days thus the collected data retention time period is 7 days. Thus at any one time there would be 40 total histograms.

The "extracted data retention time period" should be generally understood as the period over which the analysis data from an individual histogram (extracted histogram data) is stored in IMD memory before it is overwritten with new data. For example, if the extracted histogram data is the median ST deviation from the day's histogram and that median is stored in IMD memory for 6 months before it is overwritten with new data, then the extracted data retention period is 6 months.

FIG. 1 is a schematic view of the prior art AngelMed Guardian IMD 5 showing the body (or "can") 2, header 3 and lead 7. The header 3 includes a helical antenna 4 and IS1 lead interface 6. The lead 7 is for example an IS1 compatible standard bipolar pacemaker lead with a lead tip 8 and ring electrode 9. The AngelMed Guardian® IMD 5 is typically implanted similarly to a single chamber pacemaker with the lead tip 8 imbedded in the heart muscle at or near the apex of a patient's right ventricle. The AngelMed Guardian® IMD 5 disclosed herein utilizes some of the features (and corresponding systems and methods) disclosed in prior art systems, with the primary function of alerting patients to ST segment changes indicative of coronary occlusion that may indicate the patient is having a heart attack.

FIG. 2 is a schematic view of the prior art AngelMed Guardian EXD 50 with a case 52, a battery door on the reverse side (not shown) housing a replaceable battery inside a battery compartment on the back side (not shown). On the front side of the case 52 is an alarm silence button 54 and alarm related visual alerts including an emergency alarm warning LED 56 and a "See Doctor" alert warning LED 58. On the top surface of the AngelMed Guardian® EXD 50 is a serial interface connection port 55 used to connect the AngelMed Guardian® EXD 50 to the AngelMed Guardian® physician's programmer. When connected to a physician's programmer, the AngelMed Guardian® EXD 50 functions as the wireless interface for programming the IMD 5 or uploading data stored in the IMD 5 to the programmer. The AngelMed Guardian® EXD 50 and physician's programmer disclosed herein utilizes some of the features (and corresponding systems and methods) disclosed in prior art systems, incorporated by reference herein.

FIG. 3 is a block diagram of an embodiment of the ACMS 100 including the following components: an IMD 10; an EXD 120; a Subcutaneous Cardiac Monitor (SCM) 900; a Smart Device APP (SDAPP) 220 on a smartphone, tablet or PC; a Skin Surface Monitoring Device (SSMD) 800; an External Support System (ESS) 240; an ACMS physician's programmer 140, and; a programmer wand 145 with activation button 153, connection 143, near-field antenna/coil 144 and far-field antenna 146; a voice/data network 250 which may be a cellular network or a data network like the internet that also allows voice connectivity. The ACMS 100 disclosed herein utilizes some of the features (and corresponding systems and methods) disclosed in the prior art systems, incorporated by reference herein, FIG. 3 shows additional details of the EXD 120 including a microphone 155, acoustic transducer 132, EXD CPU or processor 130 with EXD memory 131, EXD battery 138, event tagging or panic button 121, visual display sub-system 135, programmer interface 141 with connecting cable 142 for connection to physician's programmer 140 external to EXD 120, alarm silence/disable button 122, near-field signaling system 133 with near-field antenna/coil 134, medical band radiofrequency transceiver 123 with EXD antenna 125 and cellular voice/data sub-system 128 with cellular voice/data sub-system antenna 129. In an embodiment, the EXD 120 may include a transceiver 147 having Bluetooth or Wi-Fi capability with antenna 148.

In embodiments, the EXD 120 connects wirelessly to:
the IMD 10, SSMD 800 and SCM 900, and using Bluetooth or Wi-Fi through the transceiver and antenna 148 or an approved medical band through the medical band radiofrequency transceiver 123 with EXD antenna 125. The medical band radiofrequency transceiver 123 would use a chipset such as the Microsemi Zarlink ZL70103 MedRadio product among others. The medical band is preferred for implanted devices because of its ability to transmit through a patient's skin;

a smart device 225 such as a smartphone, tablet, home base station or PC through the transceiver 147 with antenna 148 that could utilize Bluetooth or WiFi protocols; and through the voice/data network 250 to an External Support System (ESS) 240 and/or a Smart Device APP (SDAPP) 220 on a smart device 225 such as a smartphone, tablet, smart watch/Fitbit or PC which may function as a home-based station with connectivity of internet, phone line or cellular means to provide for transmission of data collected by the IMD 10, SCM 900 or SSMD 800 through the voice/data networks 250 to other smart devices 225 or an external support system 240.

Communication using the voice/data network 250 can be accomplished by the cellular voice/data sub-system 128 with cellular voice/data sub-system antenna 129 which could include a chipset such as the Sierra Wireless LTE-M or equivalent chipset and/or use of the Bluetooth/Wi-Fi transceiver 147 paired with a smart device 225 that has access to the voice/data network 250.

The EXD 120 includes an EXD CPU 130 with EXD memory 131. The EXD CPU 130 connects to an alarm silence button 122 realized as similar to the AngelMed Guardian® EXD 50 of FIG. 2. The EXD CPU 130 can also connect to at least one additional button such as an event tagging or panic button 121 which is used by the patient to indicate an event that may need medical review. Use of the panic button 121 could initiate voice or data messaging through the voice/data network 250 as well as sending a signal to the IMD 10, SSMD 800 or SCM 900 to sense a defined duration of data for later review.

The EXD 120 provides patient alerting through its acoustic transducer 132 which may be a loudspeaker or a piezoelectric transducer. Additional alerting is provided by the visual display sub-system 135 that would typically be one or more LEDs or an alpha/numeric display. A vibrator 139 may also be incorporated into the EXD 120 as an additional alerting or feedback mechanism. The vibrator 139 may be realized as a piezoelectric transducer, a vibrator motor or a Linear Resonant Actuator (LRA). An LRA is like a speaker coil driving a mass inside an enclosed case. Similar in size and shape to a pancake style vibrator motor and available with z-axis motion ideal for the patient alerting application. Such an LRA vibrator can be configured and programmed to control the vibration, resonant frequency and add haptic feedback for either the EXD 120 or IMD 10.

The AngelMed Guardian EXD 50 of FIG. 2 provides only local alerting from sound producing internal speaker (not shown) and/or flashing LEDs 56 and 58. The present invention ACMS EXD 120 expands upon the AngelMed Guardian® EXD 50 capabilities by adding connectivity to voice/data networks 250. This would enable alarms and alerts with or without captured data from the IMD 10, SSMD 800 or SCM 900 to be passed to those who need to know about the event who have a smart device 225 with SDAPP 220, without need for an ACMS physician's programmer 140. Those who might receive such a notification include: a patient's cardiologist; an on-call cardiologist for the practice managing the patient; a patient's emergency contact; a patient caregiver; a patient's GP; an Emergency Department closest to the patient which is predefined or dynamically determined using geolocation methods (e.g., GPS, cellular location, etc); an Emergency Department selected by the patient; an alarm monitoring service which expedites patient triage and transportation to a medical facility.

In embodiments, the EXD 120 is in a wristwatch form factor that provides the alerting capabilities of the EXD 120. Such a unit could include a vibrator 139 that would have a vibration-only privacy mode defined in the EXD CPU 130 which provides patient notification with sound turned off for privacy concerns as is common in standard cell phones. The privacy mode is enabled by the physician's programmer at the time of programming or may incorporated into a switch (not shown) or pressing together two buttons on the EXD 120. Further, a privacy protocol may be defined with a sonic alarm that for privacy concerns may also be realized as the same sound as a phone call, or is unique. Further, the EXD 120 may be realized as, or may communicate with the SDAPP 220 of a smart device 225 that can be a commercially available system worn on the wrist (e.g., Apple Watch, Fit-Bit) or custom built smart-watch.

The EXD 120 may include an accelerometer 154 to detect patient motion and activity levels.

The present invention EXD 120 also includes a near-field signaling system 133 and near-field antenna/coil 134. The present invention EXD 120 includes a programmer interface 141 used to connect the EXD 120 with the connecting cable 142 to the ACMS physician's programmer 140. This lets one embodiment of the EXD 120 serve dual purposes of a patient external alerting system and as the wand for the physician's programmer 140 to be used to program a patient's IMD 10, SSMD 800 or SCM 900 and to upload data to the physician's programmer 140 from the IMD 10, SSMD 800 and SCM 900. Similar to U.S. Pat. No. ('023), the EXD 120 could also use a wireless connection for communication with the physician's programmer 140. Connections, for example, may be a serial, USB cable or a Wi-Fi or Bluetooth wireless connection.

Also shown are embodiments of the SSMD 800 and/or the SCM 900 realized using three electrodes. Without being bounded by theory, while 2-5 electrodes may be realized on a small housing with a form factor somewhat longer than a standard loop recorder (implanted) or patch (cutaneous), it is contemplated that three electrodes would be one preferred embodiment for use in ST monitoring for ischemic events including ACS events/heart attacks and demand ischemia. The separation between electrodes in the SCM 900 may need to be longer than that of a standard loop recorder.

Figure 14:
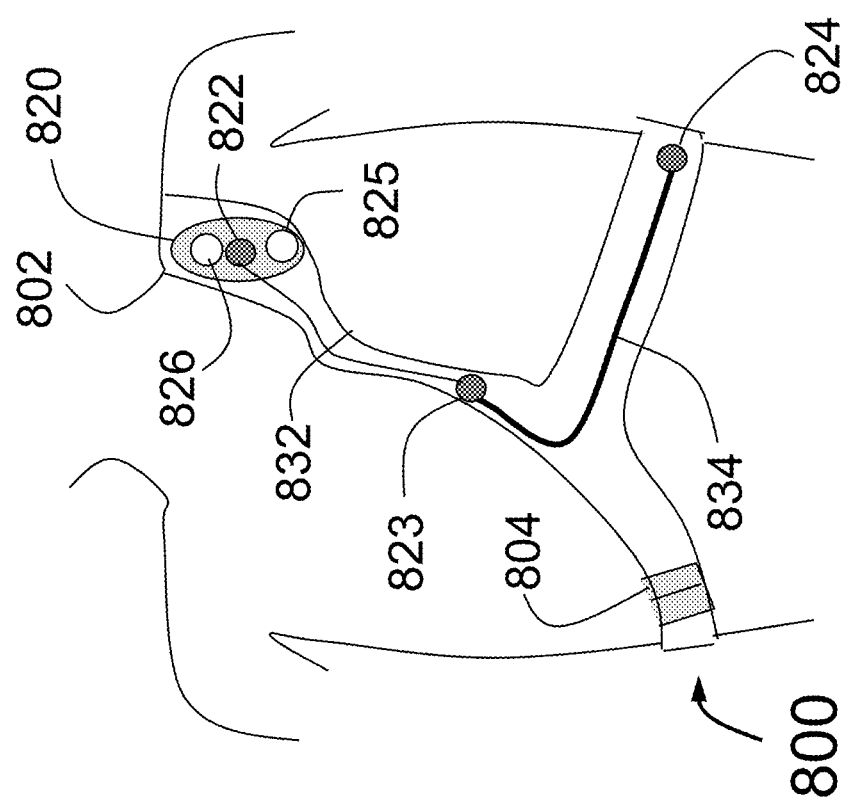
FIG. 14 is a schematic view of a Skin Surface Monitoring Device (SSMD)

FIG. 14 shows a 3-electrode vest embodiment of the SSMD 800. Two electrodes would be sufficient for heart rate monitoring and arrhythmia detection. Without being bounded by theory, a combination of two or more SCMs 900 may function to obtain sufficient coverage across the torso to identify ST segment changes associated with occlusions of all three major coronary arteries.

The physician's programmer 140 of the ACMS 100 would have a separate programmer wand 145 with activation button 153, near-field antenna/coil 144 and far-field antenna 146 to enable EXD 120 to be produced without the programmer interface 141. In this case the programmer wand 145 utilizes the wired or wireless connection 143 for communication with the physician's programmer 140. The programmer wand would typically have a device access button (not shown) to initiate near-field communication to the IMD 10, SSMD 800 or SCM 900 through the near-field antenna/coil 144. Such an initiation would signal the IMD 10, SSMD 800 or SCM 900 to turn on the far-field communication capability.

In embodiments, the processor of the EXD 120 operates a communication protocol that is configurable to respond to communication signals emitted by a single IMD 10 or SCM 900 to which it is paired. The EXD 120 pairing can occur during initial programming session with instructions from the physician's programmer, or the EXD 120 itself could allow a user to provide user input (e.g. pressing a sequence on its alarm silence button such as 5 button presses of about 1 second each) that initiates a "pairing mode" defined in the EXD CPU 130 that is provided by a communication module in the EXD memory 131 of the EXD CPU 130 which enables it to pair with a unique IMD 120 which is within the communication range of the EXD 120. Subsequent to this pairing, during an actual alarm event, the IMD 10 or SCM 900 transmits a signal which may be detected by an EXD 120 through its medical band radiofrequency transceiver 123 with EXD antenna 125, but the EXD 120 will not alert unless the alarm signal is from its "paired" IMD 10 or SCM 900. Additionally, when two patients live together, it may be advantageous to allow the EXD 120 to have a "multi-pairing mode" defined in the EXD CPU 130 that allows the EXD 120 to be paired to more than one IMD 10 or SCM 900. Alternately, it is envisioned that the EXD 120 can be set to turn off its "pairing mode" as defined in the EXD CPU 130 to enable the EXD 120 to operate in a non-paired mode defined so that it will alert if any IMD 10 or SCM 900 in its vicinity transmits an alert signal. While a multiple-paired mode may be helpful when two family members are patients with implanted devices (since it decreases the risk of an alarm unintentionally being ignored) allowing EXDs 120 to respond to any IMD 10 or SCM 900 may cause confusion or other problem when used in public areas where two strangers may be in proximity to each other upon the triggering of an alarm. Accordingly, pairing modes may be selected by a physician or user, or may be selected by the processor of the EXD 120 based upon geolocation data indicating whether a patient is at home or not.

In an embodiment, notification protocols defined in the memory 131 of the EXD 120 can define different notifications to occur at pre-defined intervals. For example, a notification protocol may define an alarm protocol in which the EXD CPU 130 may be configured to provide secondary alerting by sending a text message through the Bluetooth/Wi-Fi transceiver 147 with antenna 148 or the integrated cellular voice/data sub-system 128 with cellular voice/data sub-system antenna 129 to a smart device 225 to a defined contact upon receipt of an alarm signal transmitted by the IMD 10 or SCM 900. This secondary alerting could be immediate or after a delay of for example, 15 minutes, so that the patient is not contacted by a concerned family member prior to calling for an ambulance (e.g., 911).

An embodiment of the EXD 120 includes a real time clock 152 to provide for local or internationally time-stamping of detected events and saved heart signal parameter data that may be transmitted to it by an 1 MB. The real time clock 152 of the EXD 120 may experience clock-drift and so the processor of the EXD 120 may be configured to adjust the time of the real-time clock using a wireless time synchronization protocol which periodically obtains time updates from a smart device 225 or through the voice/data network 250. The EXD 120 can obtain a time-signal from a smart device 225 through the cellular voice/data sub-system 128 or other source. The clock time (or cumulative counter tick value) of the IMD at the time of the alert, the identification of the physician's programmer used to communicate during any data communication operation, the source of the synchronization signal (e.g., smart-phone), time of the synchronization, and any other relevant information (e.g. time zone, any daylight savings time parameters that may be toggled) may be included in a synchronization log stored in the memory 131 of the EXD 120. The order of the devices, and list of permitted devices, which can provide time synchronization signals can be defined by a user or the ACMS physician's programmer 140. The ability of the EXD 120 to obtain and store date and time information registered by the EXD 120 and IMD 10 and physician's programmer as part of the communication protocol that occurs when communication occurs or is attempted between any of these devices enables accurate determination of the timing of the alarmed event, timing of a button press for event tagging or to calculate the duration between being alarmed and patient input indicating acknowledgement of the alarm, the time at which the EXD 120 establishes communication with a physician's programmer (at an Emergency department or ambulance). The communication protocols of the physician's programmer and IMD 10 should also allow for sending and receiving timestamp information for added redundancy. Further, the EXD 120 can be configured with RFID or other communication protocol that interacts with internet of things (IOT) sensors/transmitters which are established at Emergency departments to automatically establish the time of arrival of a patient after an alarm occurs.

The battery 138 of the EXD 120 could be rechargeable and operate with charging system 137 realized with a surface interface connector such as a mini or micro-USB connector and/or a charging coil (not shown) for wireless recharging.

While the EXD 120 can connect to the physician's programmer 140 through a programmer interface 141, that can also occur wirelessly such as through Wi-Fi or Bluetooth. Inductive EXD 120 charging may occur using standard cell phone inductive charging stands or a home base station version of the smart device 225.

In embodiments, the EXD 120 may have or communicate with sensors for monitoring Body temperature and blood pressure, Glucose level or Oxygen saturation level, for example, using optical sensors and related methods, or Fatty acid Binding Protein 3 (FRBP3), CPK and/or Troponin which are indicators of a heart attack.

The ACMS 100 is configured to communicate data including, for example, alarm/alert and heart signal related data from the IMD 10, SSMD 800 or SCM 900 to the ESS 240. The data includes event related data such as data associated with an ischemic event typically characterized by ST changes, heart rate and rhythm related events including arrhythmias, an extended/prolonged period heart rate elevation, direct capture of heart electrocardiogram and electrogram data. Other data for monitoring the cardiovascular condition of a patient can include: ischemia tracking data such as the ST deviation histograms; heart rate tracking data; periodically captured electrocardiogram and electrogram data; data from other sensors such as blood pressure data, blood oxygen saturation data, body temperature, patient activity from an IMD accelerometer 75 etc; and streamed electrogram data that allows the visualization of the patient's heart signal as it is happening. The streaming may be in near real time with only small delays associated with the processing and transmission. To avoid running down the IMD battery, through use of the wireless transceiver this may be accomplished using a burst mode protocol for communication. For example, 10 seconds of data are stored by the IMD and then transmitted to an external device in a fraction of a second or other limited duration. The burst mode provides time data from a real-time clock or counter of the IMD, to enable the physician's programmer to determine the exact time at which the IMD data were recorded to enable these to be temporally aligned with samples of externally recorded data.

Voice connectivity provided by use of the microphone 155 with amplifier 156 and A/D converter 158 and audio interface with acoustic transducer 132 of the EXD 120 can allow a patient and medical practitioner to both speak as may occur during a communication session that is established as part of the post-alerting operations defined in the processor of the EXD 120 in response to a detected event, patient pressing an event tagging or panic button 121, or in response to transmission of longer term tracking data collected by the ACMS 100. Alternately, such voice connectivity can be provided by a patient smart device 225 as current smart-phone, tablet or PC typically have integrated voice communications capabilities. These can be enhanced further by video apps such as Facetime, Skype or Zoom which are integrated into the post-alerting operations defined in the processor of an EXD 120 or home base station.

Voice connectivity can be used in numerous ways including:
1. an automated call from the EXD 120 or patient smart device 225 to a medical practitioner when a cardiac event is detected,
2. a call launched by the patient using the EXD 120 or patient smart device 225 after an alarm has occurred, for example by using the panic button 121, 3. a data message sent through the voice/data network 250 to a medical practitioner that uses their SDAPP 220 to initiate a voice session with the patient.

It is also envisioned that the patient's wired home, cell or work phone, or a wearable like a Fitbit or Apple watch might be called.

The ACMS 100 would at a minimum have a physician's programmer 140, heart sensing device (an IMD 10, SCM 900 or SSMD 800) with the capability to sample electrical signals from a patient's heart and an EXD 120 with wireless connectivity to the sensing device.

In a preferred embodiment the EXD 120 would have cellular data connectivity to the voice/data network 250 and an ESS 240 typically in the form of a HIPPA compliant cloud server accessible by medical practitioners, technicians and care givers through the SDAPP 220. Where applicable, EXD 120 capabilities described herein could be combined into the SSMD 800. It is also envisioned that the capabilities described herein may be applicable to systems like the Zoll Life Vest which is a patient worn Automated Electronic Defibrillator (AED).

In a preferred embodiment of the present invention, the IMD 10 is implanted along with the primary/secondary leads 112/115 that have electrodes that can sense the heart's electrogram. Although the present invention (as described herein) in most cases refers to the preferred embodiment of an IMD 10 which can process electrogram data from pacemaker like implanted electrodes, the techniques described are equally applicable to embodiments integrated into a pacemaker, cardioverter of ICD or using one or more SCMs 900 or an SSMD 800 to process heart signal data from appropriately placed subcutaneous or skin surface electrodes.

In one embodiment of the IMD 10, either or both subcutaneous electrodes or electrodes located on a pacemaker type right ventricular or atrial leads can be used. It is also envisioned that one or more electrodes may be placed within the superior vena cava or other vessels of the circulatory system. Skin surface electrodes or other external or implantable sensors are envisioned as well forming a multi faceted health monitoring system.

A preferred embodiment of the SSMD 800 or SCM 900 for ST monitoring would have at least three sensing electrode locations. If exactly three are used, a preferred embodiment would have electrodes at locations below the left clavicle, near the sternum and under the skin on the patient's left side near the bottom of the rib cage. Still another embodiment of the IMD 10 could utilize epidural electrodes attached externally to the heart.

The ACMS physician's programmer 140 is used to program the sensing devices with respect to any or all of diagnostic, detection, alarming and alerting functions. The physician's programmer 140 is also used to retrieve and analyze recorded electrocardiogram/electrogram segments and event related and processed heart signal data from the sensing device memory. The physician's programmer 140 would include two modes of operation:
1. A first mode where it communicates by wired or wireless means in proximity to the sensing device (IMD 10, SSMMD 800 or SCM 900) through the link H2 to the EXD 120,
2. A second mode where it communicates through the cellular data capability of the EXD 120 allowing the sensing device data to be programmed remotely and data stored in the sensing device to be uploaded to the physician's programmer 140. Additional security protocols are envisioned for device programming remotely.

An additional preferred mode of operation of the ACMS 100 is to have alerts based on events detected by the IMD 10, SSMD 800 or SCM 900 that are received by the EXD 120 be communicated directly with the SDAPP 220 on the Smart Device 225 using the Bluetooth/WiFi transceiver 147 with antenna 148. This can provide additional alerting and information to the patient and the cellular or Wi-Fi connectivity of the Smart Device 225 can be used to transmit the alert and related data through the voice/data network 250 to either the external support system 240 or directly to a 3rd party such as a caregiver, cardiologist, emergency department at a local hospital or a medical practitioner or technician that is part of a concierge service. This method has the advantage that the smart device is likely to have patient GPS location that can be of huge benefit should the patient be disabled during a potential event.

It is also envisioned that one or more embodiments of the ACMS 100 of FIG. 3 would include a streamed telemetry mode where the IMD 10, SSMD 800 or SCM 900 could stream electrogram/ECG signal data for local display and/or data collection. This feature would be of great benefit for remote patient management or to see existing heart signal data from the patient upon presentation at a medical facility without the need to attach ECG electrodes to the patient's skin. Other measurements sensed by the IMD 10, SSMD 800 or SCM 900 could also be streamed including temperature, blood pressure and O2 saturation.

In the 1960s Star Trek showed a medical bed where without attaching wires to the patient, there could be streamed medical information displayed above the bed for the doctor's use. This streaming capability can turn the science fiction into reality for patients with an ACMS.

The streaming function may be conducted in one of several ways including:
1. Use of the EXD 120 as a transceiver to send the streaming data to a smart device 225. This could use the SDAPP 220 that could have a streaming function.
2. Directly from the IMD 10, SSMD 800 or SCM 900 to a version of the EXD 120 that utilize the wireless technology used by the IMD 10, SSMD 800 or SCM 900.

In embodiments, the present invention ACMS 100 also includes software routines for patient alarm training that allow patients to experience the vibratory, auditory and visual alarms provided by the IMD 10, SSMD 800, SCM 900 and/or EXD 120, or other system component that provides notification of a patient or remote entity during actual alarm. The physician's programmer 140 includes a training alarm module 149, which enables a medical practitioner to trigger an alarm signal. It is envisioned that the training alarm module 149 could also be used to adjust the intensity of the alarm for the IMD 10, SSMD 800, SCM 900 and/or EXD 120. The intensity adjustments can include adjustments for the ACMS 100 alerting mechanisms including vibrators acoustic transducers and/or visual alerts. The training alarm module 149 can adjust intensity and trigger any of the alerting modes of the ACMS 100. For example, if the ACMS 100 includes two modes, Emergency Alarms and See Doctor Alerts as described in the prior art, then the training alarm module 149 can turn on and off and adjust intensities of either mode. Such training alarms are also important to allow the patient to practice silencing the alarm using the alarm disable button on the EXD 120. In a preferred embodiment this requires the EXD 120 be brought into the range of the near-field signaling system 133 with near-field antenna/coil 134 when the alarm disable button 122 is pressed.

The training alarm module 149 when used to program the intensity level(s) for actual alerts provided during treatment allows for increasing or decreasing the intensity of the IMD 10 or SCM 900 vibrational alerts to be sure the patient can feel it and it is not so intense as to cause pain.

The training alarm module 149 when used to program the intensity level(s) for actual alerts provided during treatment allows for increasing or decreasing the intensity of the EXD 120 or SSMD 800 acoustic alert to be sure the patient can hear it, and EXD 120 vibration alert if also provided. In addition to the acoustic intensity being adjustable, for example from about 70 dB to 120 dB, the frequency can be modifiable to address patients with low or high frequency hearing loss. Additionally, the tones can include 2 or more alternating frequencies such as 1000 Hz and 2000 Hz to increase the likelihood of the tone being outside of frequency range of hearing loss. In one embodiment, the training alarm module 149 enables adjusting of the pattern or content of one or more types of acoustic alert to make it more detectable by the patient in various manners. For example, patients are more likely to attend to their own name or voice instead of simply tones. The patient (or a caretaker or family member) can record their own name into the EXD 120 which can be played back to them during an alert or may be presented only they fail to press the alarm silence button.

The training alarm module 149 when used to program the intensity level(s) for actual alerts provided during treatment allows for increasing or decreasing the intensity of the EXD 120 or SSMD 800 visual alert to be sure the patient can see it, and in some embodiments adjust the color of the visual alert if it is a flashing light or LED to ensure the patient can tell the difference if they are color blind.

Figure 4:
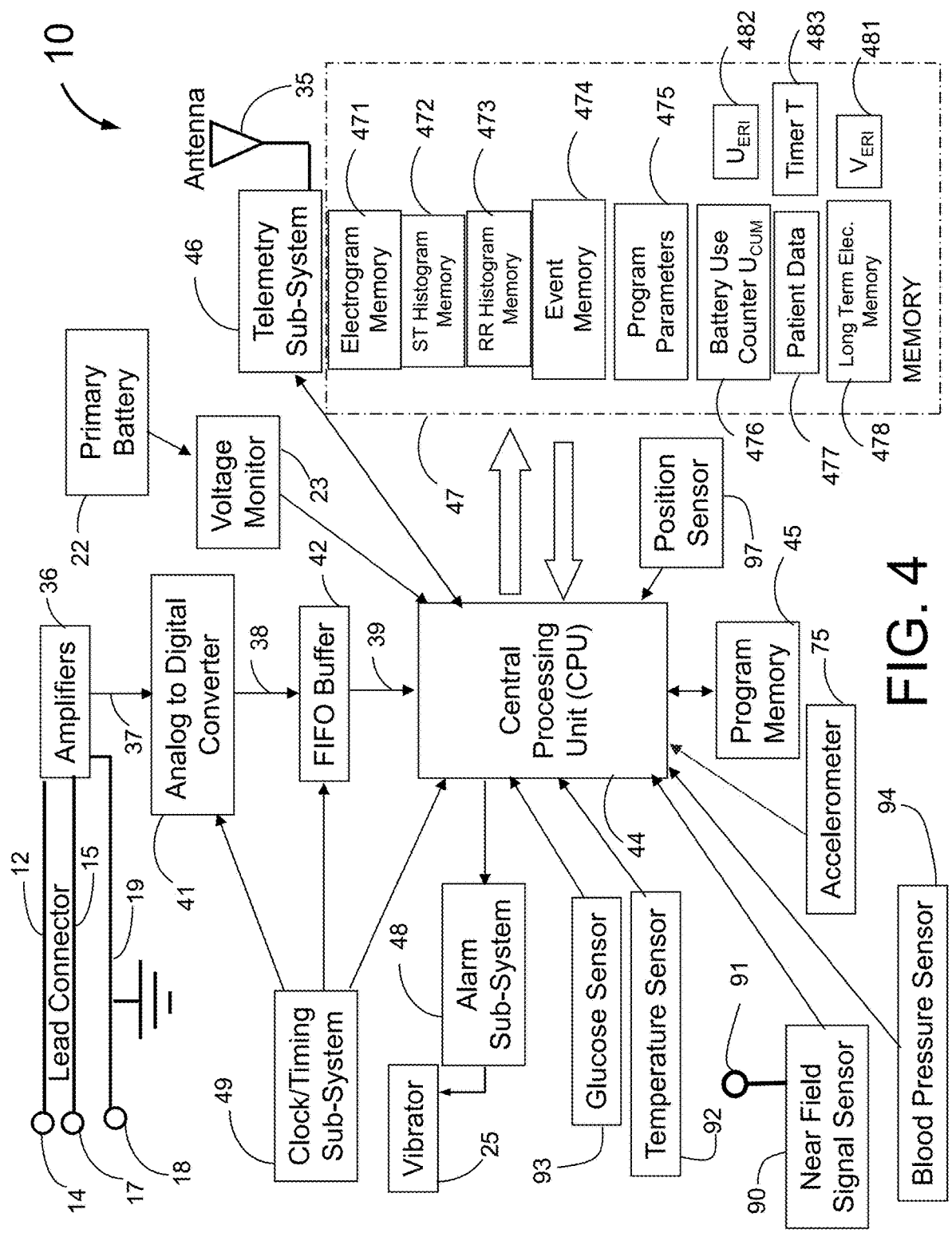
FIG. 4 is a block diagram of the present invention ACMS IMD/SMD.

FIG. 4 is a block diagram of the present invention IMD 10 which a component of the ACMS 100. Some of the functionality of the IMD 10 and the SCM 900 is described in prior art systems. The IMD 10 includes a IMD CPU 44, program memory 45, a lead connector with electrodes 14 and 17. The electrodes 14 and 17 may be part of a standard lead interface such as the IS1 lead interface 6 of FIG. 1, which may be an IS1 pacemaker lead interface. A feed thru (not shown) is part of the conductors 12 and 15 which connect to the electrodes 14 and 17. The IMD 10 system ground 18 is typically the can of the IMD 10. While the term IMD 10 is used here, the block diagram shown in FIG. 4 is also applicable to the SCM 900 and SSMD 800 of FIG. 3 that provide respectively subcutaneous and skin surface electrode sensing of heart signal data. As seen in FIG. 4 amplifier 36 through conductor 19 goes to ground 18.

The IMD 10 includes memory 47 with allocations for electrogram memory 471, histogram memory 472, Event Memory 474, Program Parameters Memory 475, Patient Data Memory 477 and Long term electrogram memory 478. In addition, the IMD 10 includes one or more amplifiers 36, and analog to digital conversion circuit 41, a clock timing sub-system 49, a First-In-First-Out (FIFO) memory buffer 42 feeding digitized heart signal data to the IMD CPU 44. Also included is an Alarm Sub-System 48, a position sensor 97, IMD accelerometer 75, Vibrator 25, Telemetry Sub-System 46 and antenna 35 for wireless data communication to external equipment. It is also envisioned that a microphone (not shown) could be added for additional input to the IMD CPU 44. The clock timing sub-system 49 is coupled to one or more of the digital converter 41, FIFO Buffer 42, and IMD CPU 44 for providing control signals in operating the IMD 10.

In implanted cardiac monitors such as the IMD 10 and SCM 900 of FIG. 3 the external system components would typically include the EXD 120 of FIG. 3. For an external embodiment like the SSMD 800 of FIGS. 3 and 14, the telemetry sub-system 46 and antenna 35 could be Bluetooth transceiver to communicate with a computer, smartphone or tablet or could be a cellular voice/data transceiver similar to the cellular voice/data sub-system 128 with cellular voice/data sub-system antenna 129 of the EXD 120 of FIG. 3.

Unlike the prior art systems, the IMD 10 has the additional inclusion of a battery voltage monitor 23, a near-field signal sensor 90 with antenna/coil 91 and additions to the memory 47 (which may be RAM memory) of R-R Interval Histogram Memory 473, Battery Use Data Cumulative Counter ($U_{CUM}$) 476, Timer T 483, Battery Voltage Effective Replacement Indicator (EM) threshold $V_{ERI}$ 481 and Cumulative battery usage Estimated Replacement Index threshold $U_{ERI}$ 482. Other sensors that may be combined in the IMD 10 include, for example, a Glucose Sensor 93, Temperature Sensor 92 and Blood Pressure Sensor 94. The blood pressure sensor 94 could be best positioned as part of the primary lead 112 or a secondary lead 115 shown in FIG. 3.

A preferred embodiment of the telemetry sub-system 46 with antenna 35 uses the FCC approved medical band with Radiofrequency based on a chipset such as the Microsemi ZL70103 MedRadio product among others. The medical band is preferred for implanted devices because of its ability to transmit through a patient's skin. Low power Bluetooth is also envisioned as a wireless standard that could be used by the telemetry sub-system 46.

The near-field signal sensor 90 with antenna/coil 91 is designed to receive a signal from the near-field signaling system 133 and near-field antenna/coil 134 of the EXD 120 of FIG. 3. The near-field signal sensor 90 provides several important features of the ACMS 100. One feature allows the IMD 10 to have its telemetry sub-system 46 turned off almost all the time. As these systems use a significant amount of power, the ability to have the near-field signaling system 133 of the EXD 120 cause the IMD 10 CPU 44 to turn on the telemetry sub-system 46 only when needed will conserve power and lengthen the life of the primary battery 22. There are four important examples of where this is used in the present invention ACMS 100.

1. For local programming or to retrieve data from the IMD 10 or SCM 900, the programmer wand 145 or EXD 120 of FIG. 3 are first connected to the ACMS physician's programmer 140 of FIG. 3. To activate a programming session using the wireless communication between the telemetry sub-system 46 with antenna 35 of the IMD 10 and the medical band radiofrequency transceiver 123 with EXD antenna 125 of the EXD 120, the EXD 120 is positioned close to (in the near-field of) the implanted IMD 10. The near-field could be for example against the patient's chest over the implanted device or within a pre-set distance for example 1-5 cm. The maximum range should be 20 cm or less. This provides an important level of security as it requires access to the device be initiated right against the patient.

Once in position, a button such as the alarm silence button 122, an event tag button (not shown) or the panic button 121 of the EXD 120 of FIG. 3 is depressed activating the near-field signaling system 133 which sends a signal through the near-field antenna/coil 134 of the EXD 120. That signal is sensed by the IMD 10 near-field signal sensor 90 with antenna/coil 91. The antenna/coil 91 can be a simple coil or some type of antenna or pickup to receive the near-field signal from the EXD 120. In one example, the near-field signal sensor 90 could change the voltage on a pin of the IMD CPU 44 from zero to one indicating a request to turn on the telemetry sub-system 46. The programmer wand 145 activation button 153 of FIG. 3 would typically be used with a similar near-field access technique.

Additional levels of security can be achieved in by either a unique initial signal or with "hand shaking" security protocols that would occur with the EXD 120 or physician's programmer 140 begin a far-field communication session with the IMD 10.

2. To silence an alarm, the patient would place their EXD 120 within the near-field as described in 1 above and depress the alarm silence button 122. The IMD CPU 44 of the IMD 10 will see this and terminate the vibratory internal alarm as well as signal the EXD 120 to stop the visual alarms displayed through the visual display sub-system 135 and audible alarms sent to the acoustic transducer 132 of the EXD 120 of FIG. 3. For the ACMS 100 of the present invention this would also put in motion the process shown in FIG. 10 to provide a reminder alarm.

3. To request assistance from a medical practitioner or service support person who would interact with the patient to facilitate their treatment (could be called a cardiac concierge), or to lock in memory 47 current data including electrograms stored in the IMD 10 for later review by a medical practitioner, near-field activation can be initiated by depressing the panic button 121 with the EXD 120 placed in the near-field. For example, if the EXD 120 is placed in the near-field and the panic button 121 is depressed, a unique sound or LED flash might occur to confirm the activation of a request to the IMD 10. In one example of this occurring, the IMD 10 could upload to the EXD 120 all the recent data stored in its memory from the last 24 hours for transmission through the EXD 120 cellular voice/data sub-system 128 and cellular voice/data sub-system antenna 129 to the ESS 240 of FIG. 3 with an additional message indicating a patient request for assistance. A message can then be sent by the ESS 240 to a medical practitioner who is enabled activate the SDAPP 220 to view the information that would typically also include the patient's contact information or means to enable the voice connection feature in the EXD 120. Alternately, the message with or without associated data could be sent directly to the smart device 225 of FIG. 3 of a medical practitioner, care giver or technician. This is further discussed in the detailed description of FIG. 18.

4. It is envisioned that the alarm silence button 122 of the EXD 120 when depressed other than in the near-field of the IMD 10 or SCM 900 of FIG. 3 would normally induce an acoustic or visual signal on the EXD 120, for example a single beep or flash of an LED to act as a device check for the EXD 120. This is designed to be different than the depression of the alarm silence button 122 in the near-field of the IMD 10 or SCM 900 of FIG. 3 where the reception of a near-field signal by the IMD 10 would cause the IMD 10 to turn on its telemetry sub-system 46 where the IMD 10 would send a confirmation signal to the EXD 120 through the medical band radiofrequency transceiver 123 which causing the EXD 120 to provide an additional confirmatory sound, light or both signal. For example, a 2nd beep and light flash could be provided. This allows the patient (or medical practitioner) to verify that the IMD 10 is alive and functioning. If no additional data communication occurs between the IMD 10 and EXD 120 after a time out period, the IMD 10 telemetry sub-system would turn off to conserve energy. If no communication occurs whatsoever, it is also envisioned that the EXD 120 could display using the visual display sub-system 135 of FIG. 3 and save in EXD memory 131 a communication error message.

One mechanism for providing this near-field wake-up function for the features 1-4 above is to have the near-field antenna/coil 134 of the EXD 120 and antenna/coil 91 of the IMD 10 be simple wire coil. Then the wake-up signal received by the near-field antenna/coil 134 could be a magnetic pulse produced by the near-field signaling system 133 of the EXD 120 of FIG. 3. Such a magnetic pulse can easily go through the skin and be received by the antenna/coil 91 and be detected by the near-field signal sensor 90.

Additional processing to facilitate detection of the signal may include where the signal is amplified, filtered, the signal envelope is demodulated and the signal is input to the IMD CPU 44, which upon reception of a valid digital data packet the IMD CPU 44 would initiate the turning on of the telemetry subsystem 46 and the opening of a communication session with the medical band radiofrequency transceiver 123 of the EXD 120. As the IMD CPU 44 executes it firmware instruction loop as stored in the program memory 45 it will periodically look for the digital data packet from the near-field signal sensor 90. The IMD CPU 44 will time out after a pre-set time period if no communication occurs.

While the activation button 153 on the programmer wand 145 of FIG. 3, the alarm silence button 122 and panic button 121 have all been cited as potential ways to initiate a communication session between the IMD 10 and EXD 120 using near-field communication, it is also conceived that simply placing the EXD 120 or programmer wand 145 near the IMD 10 could activate the near-field sensor. For example, since the IMD 10 and EXD 120 would both be aware if an alarm has occurred as the EXD 120 is always listening with its medical band radiofrequency transceiver 123, the EXD 120 could initiate sending out appropriate near-field pulses that would activate the near-field signal sensor 90 when the EXD 120 is brought within the near-field without the need for the patient to depress the alarm silence button 122.

In another embodiment, the EXD 120 (or programmer wand 145 of FIG. 3) could periodically send pulses or its near-field signal to activate the near-field signaling system 133 by simply placing the EXD 120 in the near-field allowing it to initiate a communication system. This is particularly practical for the programmer wand 145 that could begin sending pulses once the physician's programmer 140 is turned on.

The Vibrator 25 can be a piezoelectric buzzer, a miniature vibrator motor with an off-center weight such as that typically used in cell phones or an LRA, or some like mechanism which provides for a tactile sensation. In cases where a miniature brushed motor is used, such motors are more reliable if exercised on a regular basis. One aspect of the present invention IMD 10 is to have the IMD CPU 44 enable periodic activation of the vibrator 25. This should be done in a way, however, that will not frighten or alarm the patient. As such it can be either a daily activation that occurs at a specified time that can be sensed by the patient—such as a "noon whistle" that lets the patient know the device is functioning or a very short burst of several turns of the motor that would be imperceptible to the patient.

The present invention IMD 10 alarm sub-system 48 includes means to increase or decrease the intensity of the vibration delivered by the vibrator 25. This can be accomplished through an increase in voltage, current and/or pulse frequency used to turn the vibrator 25 from its off state to its on state. Intensity level may be either a continuous adjustment or preferably two or three preset levels.

In embodiments, the physician's programmer 140 of FIG. 3 is used to: 1) establish a programming session with the IMD 10 by near-field activation; 2) program the appropriate settings for ST level monitoring, 3) Program other detection settings as required; 4) inform the patient that they will now get to experience the vibrational alarms; 5) initiate a patient training session. An example of such a session using the training alarm module 149 would involve the following steps:

Step 1—activate the vibrator 25 to demonstrate Emergency Alarms at 2 or more intensity levels;

Step 2—obtain patient feedback to determine an appropriate level to set the alarm parameters of the IMD 10 (e.g., as high as possible without being painful).

Step 3—set parameters for Emergency Alarms and/or See Doctor Alerts based on patient feedback.

Step 4—train the patient by providing Emergency Alarms and See Doctor Alerts. This can occur for a particular alarm component (e.g., just for vibration) or using more than one alarm modality, and for the IMD 10 or EXD 120 in isolation, or both together. As part of step 4 the patient is trained to use the EXD 120 of FIG. 3 to silence an alarm using near field communication.

Step 5—Provide any additional instructions to the patient (e.g., instruction to not ignore symptoms since the alarm may not always occur or severe symptoms may occur earlier).

The ACMS 100 realizes features supported by the firmware contained in the program memory 45 of the IMD 10 including: 1) monitoring of the primary battery 22 with patient alerting at an appropriate time interval before end of life of the primary battery 22; 2) identification and patient alerting for extended periods of elevated heart rate (e.g. to indicate non-compliance or improper dosing of heart rate regulating medications such as beta blockers); 3) reminder alarms even when the patient properly silences an initial alarm; 4) use of histograms and other tracking methods to monitor patient heart rate/R-R interval; and 5) alarms provided by the EXD 120 of FIG. 3 or the SDAPP 220 (operated on another device) which prompt the patient to perform a task or take a medication. The alarms can be associated with a detected event or may occur according to a predefined schedule. Notifications can be spoken words or text. Examples include: instructions to Call 911 and take an aspirin as part of an Emergency Alarm; instructions to take a beta blocker for an alert for an extended period of elevated heart rate; and, instructions to take an anti-arrhythmia medication for a detected irregular heart rate or AFIB.

In an embodiment, the IMD 10 is configured to detect and count arrhythmia related events including: a) incidence of PACs or PVCs b) PVC beats per electrogram segment, c) occurrences of two consecutive beats that each have a PVC, d) the incidence and duration of episodes of ventricular tachycardia, e) occurrences of three consecutive PVCs and/or f) the incidence and time duration of episodes of atrial fibrillation. Also envisioned is the identification of T-wave alternans. Arrythmia related events are computed using heart signal parameters. In addition to detection and counting of these events, the IMD 10 is configured to store sample waveforms and timestamps for these events.

Data sensed by the IMD can be predictive of ventricular fibrillation. For example, a change in the frequency of beats with a heart signal parameter may be predictive of a forthcoming episode of ventricular fibrillation. In this instance, patient notification may lead to a doctor detecting the new onset of an unknown condition in the patent and medication may be prescribed or an implantable cardioverter defibrillator (ICD) could be implanted.

Figure 5:
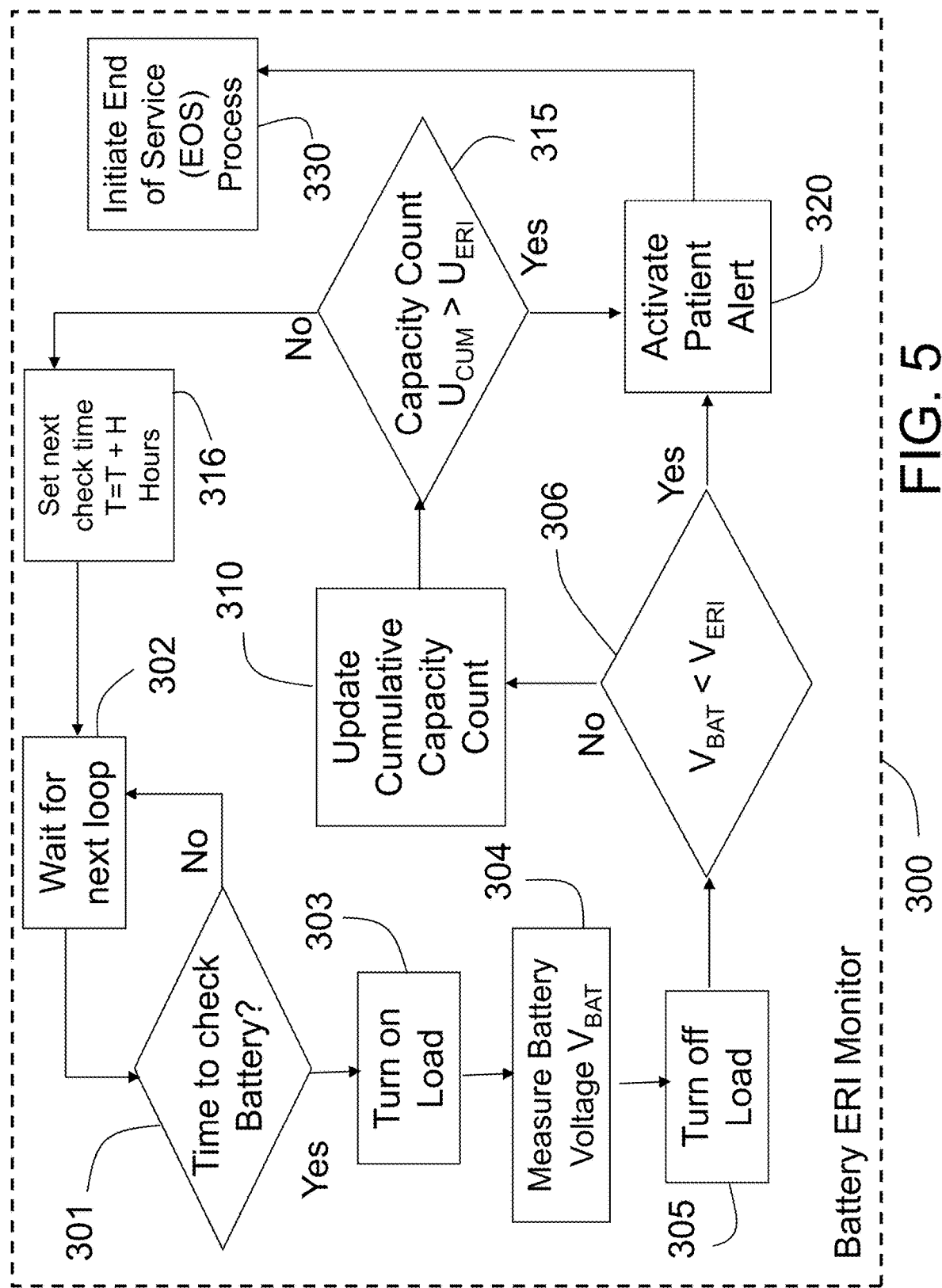
FIG. 5. is a flow chart showing the process for detecting battery Effective Replacement Indicator that uses both battery voltage and capacity count methods.

FIG. 5. is a flow chart showing the Battery Effective Replacement Indicator (ERI) process 300 stored in the program memory 45 and run by the IMD CPU 44 of the IMD 10 in FIG. 4 for alerting a patient or remote entity of the need to replace the IMD as it nears end of usable service due to primary battery 22 depletion or other battery performance issue of FIG. 4. This process also applies to the SCM 900 of FIG. 3.

In embodiments, the IMD 10 uses two independent strategies to detect battery end of life (EOL) and determine the appropriate Effective Replacement Indicator (ERI) threshold to alert the patient with sufficient remaining capacity to enable certain performance requirements to be met (e.g., provide at least one additional vibrational alert and remain active for a pre-set period of time by the end of which the IMD 10 must be replaced. Strategy #1 includes using the battery voltage monitor 23 of FIG. 4 to identify the drop in voltage that occurs in batteries as batteries become depleted. Strategy #2 includes providing an "energy use counter" which is managed by the IMD CPU 44 of FIG. 4 that is based on the known energy drain for each activity of the IMD 10. For example, the milliamp hours (or microamp hours) for each activity/function can be identified. Some activities have a defined duration such as data collection and processing of an electrogram segment or a vibrator pulse, while others such as wireless radio use have a known energy use per second or minute and the count is therefore calculated by multiplying the use rate by the duration of the event. If the evaluation of the energy counter data (e.g., the sum of the values in the energy use counter or the cumulative sum) meets a criterion then the patient is alerted to by the ERI process 300.

In one embodiment, the EM process 300 operates in the primary operating loop within the IMD 10 firmware/software to determine if it is time to check the battery voltage in step 301. If a time amount is not met in step 301, in step 302 the ERI process 300 waits for the next time through the loop. It is also envisioned that a separate timer or counter (not shown) could provide an interrupt to the IMD CPU 44 of FIG. 4 to run a battery check. The battery check could be incorporated into the code during a periodic update function for baseline data collection, e.g. per hour or per day. Alternatively, checking the battery for ERI may occur less frequently such as once per week or month. Additionally, the interval for checking the battery be set dynamically, such as once per month, until the battery level is below a selected amount at which time the interval is decreased to a shorter duration such as once per week.

Either way, if it is time to check the battery, then in step 303, the ERI process 300 has the IMD CPU 44 of the IMD 10 in FIG. 4 turn on a load so that the battery voltage monitor 23 of FIG. 4 can be measure the voltage under load. Measuring under a fixed and consistent load is important to reduce, to the extent possible, variation in measured values that have nothing to do with the health of the battery. Examples of loads that might be turned on include turning on the telemetry sub-system 46, analog to digital (A-D) conversion circuit 41 or the vibrator 25 of FIG. 4. A preferred load can be the A-D converter during sensing of an electrogram or activation of the telemetry sub-system 46. Operating the vibrator for a very short duration e.g., 10 msec, may also serve as a reasonable load.

The battery voltage under load is then measured in step 304 and the load is turned off in step 305 to minimize power use. To further obtain a stable/reliable measurement, at the time for making the measurement, multiple measurements should be made. For example, 4 sequential measurements might be taken. The high and low measurements are discarded and the remaining 2 are averaged to arrive at the functional measurement value. Additionally, the range of the measurements may be calculated. If the variation of the range exceeds a threshold then the IMD initiates an alert to the patient indicating that the power supply may be unstable. In one embodiment, to provide some hysteresis, these daily measured values may be exponentially averaged (new value=(previous value+current measurement value)/2) to arrive at the value used to compare against Effective Replacement Indicator (ERI) or End of Service (EOS) voltage thresholds described in the following sections.

Step 306 compares the measured battery voltage $V_{BAT}$ to see if it is below (less than) the pre-set EM threshold $V_{ERI}$. If the measured battery voltage $V_{BAT}$ is below (less than) $V_{ERI}$ the ERI process 300 moves to step 320 to alert the patient with a See Doctor alert and then proceeds to the EOS process 330 shown in FIG. 8. $V_{ERI}$ is determined during product development and testing to be the battery voltage indicative of sufficient capacity remaining so that not only is there energy to run the vibrator 25 and telemetry sub-system 46 to initiate internal and external patient See Doctor alerts for the need for device replacement but that there will be sufficient capacity left so that the device can remain operational for a pre-set period of time while the patient schedules the device replacement with their doctor. In one embodiment, there would also remain sufficient capacity for one additional patient Emergency Alarm if a potential heart attack with excessive ST shifts were to occur during the time between ERI and EOS.

If the measured battery voltage $V_{BAT}$ is not below (less than) $V_{ERI}$, the ERI process 300 continues to update the cumulative battery usage counter in process step 310, which includes process steps in FIG. 7. After updating the cumulative battery usage count in process step 310, the ERI process 300 proceeds to step 315 to check if the device needs replacement due to energy usage even though the battery voltage is still above $V_{ERI}$. This usage determination is based on the cumulative capacity count $U_{CUM}$.

Figure 8:
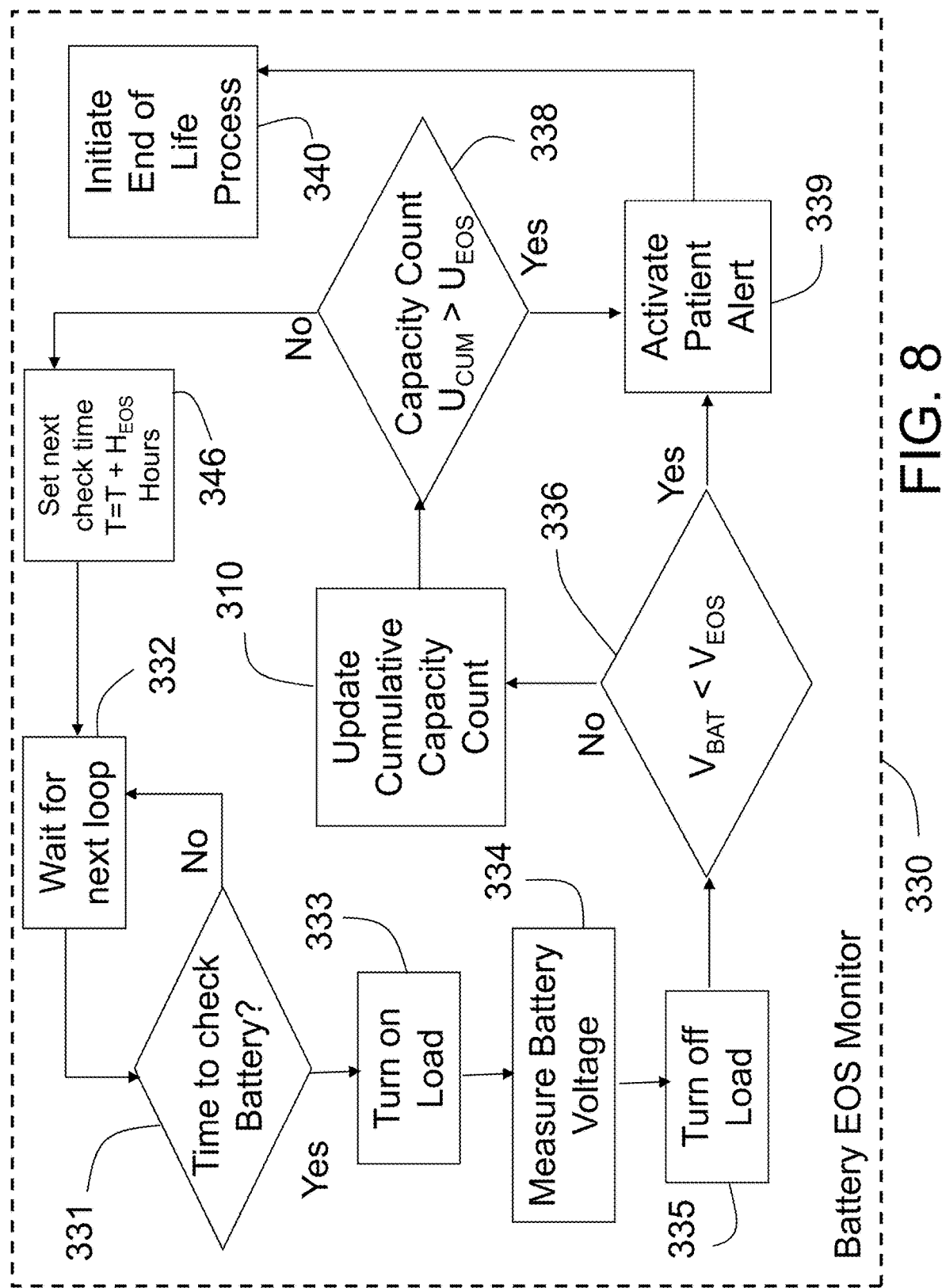
FIG. 8 is a flow chart showing the process implemented at device end of service.

In step 315 if the updated battery usage cumulative capacity count $U_{CUM}$ is greater than the preset ERI usage count threshold for cumulative battery use $U_{ERI}$ the ERI process 300 proceeds to step 320 to alert the patient with a See Doctor alert and then proceeds to the EOS process 330 shown in FIG. 8. In this embodiment, the (capacity based) ERI threshold $U_{ERI}$ is used to determine when to alert the patient a desired number of days before EOS and optionally to allow at least one Emergency Alarm to occur.

For both voltage based and usage based determinations, for example, to be able to claim at least 30 days between ERI and EOS, one might use 45 days for selecting the ERI capacity threshold. This embodiment has the advantage in that the patient remains protected by the cardiac monitoring capability during the period between the alert for EM and the replacement implant.

If the updated battery usage cumulative capacity count $U_{CUM}$ is not greater than the preset battery replacement count threshold for cumulative battery use $U_{ERI}$ the ERI process 300 then proceeds to step 316 where the time for battery check T is increased by H hours and the ERI process 300 returns to operating within the main loop of the IMD CPU 44 of FIG. 4. In an alternate embodiment, step 316 would reset a timer for the next interrupt-based trigger to the IMD CPU 44 to initiate a battery check.

It is envisioned that H can be a time of between 1 hour and 360 hours (30 days) with the preferred being 24 hours. As other functions of the IMD 10 occur once a day, this allows the timer register T to be used for multiple functions or an existing 24-hour event could be used to trigger the battery checks. It is also possible that the H could be longer during the first few years of service and/or be internally adjusted by the IMD CPU 44 as the voltage measured $V_{BAT}$ decreases or cumulative battery count $U_{CUM}$ increases.

The pre-set values $U_{ERI}$ 482, T 483, and $V_{ERI}$ 481 are stored in the memory 47 of FIG. 4. H and other parameters are stored in the Program Parameters Memory 475 section of the memory 47 of FIG. 4.

While it envisioned in one embodiment of the present invention that one could use the EOS voltage and capacity thresholds to alert the patient when there is just enough energy for a single patient alert, it is desirable to alert the patient several days or weeks before EOS just to be sure there is both enough energy left to sound the alarm and to keep the monitor going until the patient can schedule a replacement implant.

The present invention's unique use of two independent methods to determine when to alert the patient that a replacement is needed (or do other defined operation contingently upon determining a battery status meets a criterion) has the advantage that any method of trying to assess capacity ERI, either by estimation or by actual measurement of battery capacity used, must address the issue of determining a capacity threshold. If the capacity threshold is set too low, batteries with above typical capacity are not used to their fullest extent. On the other hand, if it is set too high, a higher, and potentially a much higher, percentage of batteries will run out of capacity before the EM capacity is reached. In that case, alerting the patient depends on voltage monitoring described in the EM process 300 of FIG. 4 which may not be as reliable depending on the type of battery used. This dual method is particularly of value with battery chemistries having steep voltage drops near end of life that could be difficult to catch with a voltage only measurement. Alternatively, only one method may be used and may be selected using the physician's programmer.

Figure 6:
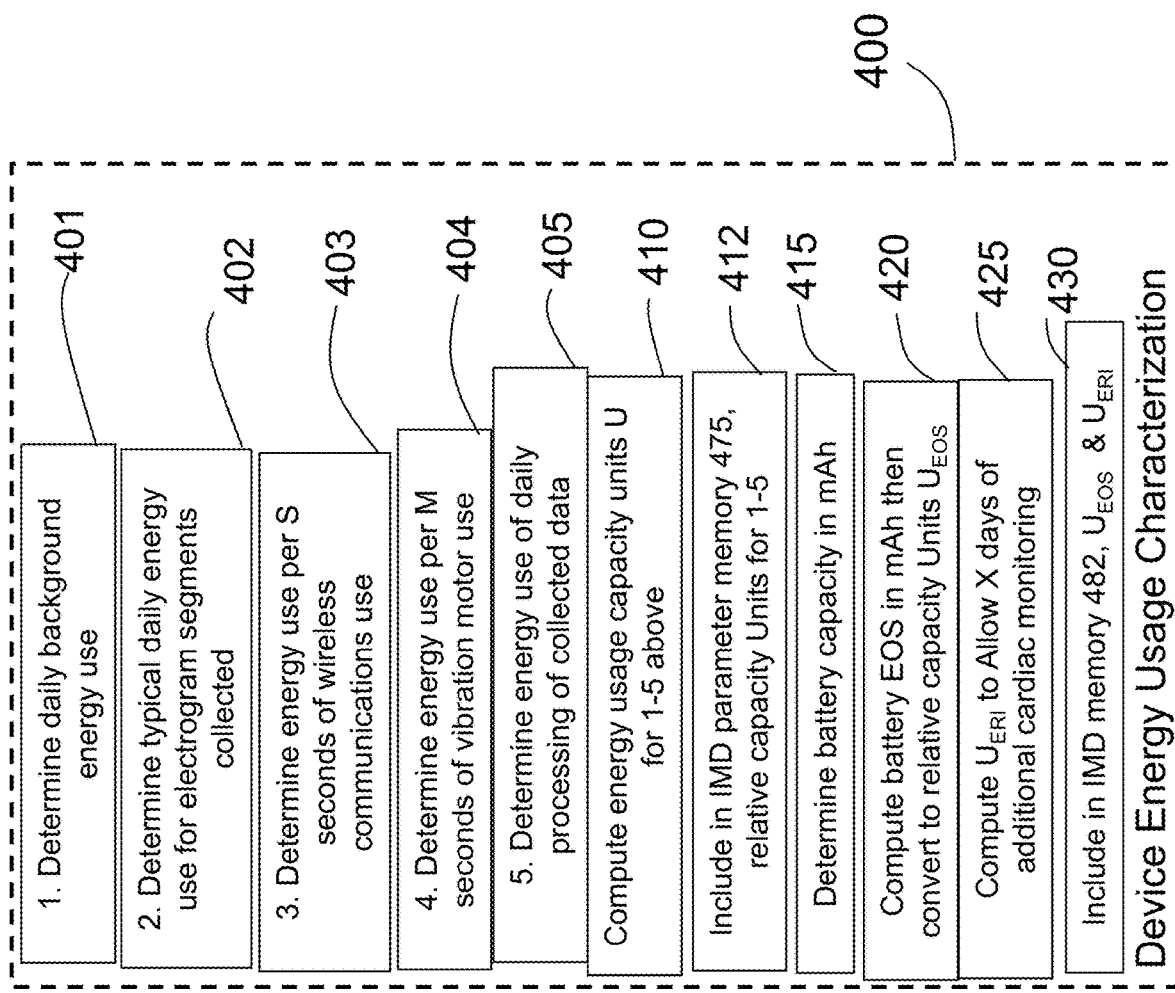
FIG. 6 shows the steps used to determine the End of Service (EOS) and Elective Replacement Indicator (ERI) for battery capacity.

A key item required to successfully use the capacity estimation process in the IMD 10 to identify battery EOS, the steps of which are shown in FIG. 8, is the Device Energy Usage Characterization Process 400 shown in FIG. 6. The process 400 is used to determine typical device energy consumption for its operational functions, determine battery energy capacity and compute an appropriate battery ERI threshold based on having sufficient capacity remaining to run the vibrator 25 of FIG. 4 and send a signal to the EXD 120 to alert the patient to battery EOS and operate the IMD 10 until a replacement can be provided. In a preferred embodiment ERI would allow residual energy as well for at least one Emergency Alarm to be provided.

In the process 400, completed during device development and testing, one characterizes energy usage of each function of the IMD 10 of FIG. 4 as well as the total energy capacity the primary battery 22 of FIG. 4. The second function includes the need to determine the threshold $U_{ERI}$ 482 stored in memory 47 of FIG. 4.

For the first of these items, the current/energy use is determined for at least the five functions states, such as:

function 1) daily background consumption when the ACMS/ IMD is idle, sub-process 401; function 2) daily data segment collection consumption when electrical data is collected for a prescribed period of time and then analyzed, sub-process 402; function 3) communication session per time period consumption during communication with other equipment during alarms, data retrieval and/or programming, sub-process 403; function 4) vibrator energy consumption per pulse and/or per time period during running of the motor for alarms and patient training, sub-process 404 and; function 5) daily processing of baseline and other data including baselines updated once per hour and histograms updated once per day as examples. It is also envisioned that the hourly events could be included with the data segment collection sub-process 405.

While sub-processes 401, 402 and 405 (function 1, function 2, and function 5 above) are characterized on a daily use basis, it envisioned that a different interval than one day can be used. For example, it could be characterized on an hourly, twice a day, every 2 days, weekly or monthly basis. Sub-processes 403 and 404 (3 and 4 above) can be characterized per second, per minute, per hour or as shown in the example below, per 10 seconds.

For example, the below table shows what might be a typical energy use for these functions.

| State/function | IMD typical consumption |
| --- | --- |
| background consumption | 251 µA-hr/day |
| data segment collection | 33 µA-hr/day for every 512 segments collected |
| communications session | 43 µA-hr/10 seconds |
| Vibration | 110 µA-hr/10 seconds |
| periodic processing | 2 µA-hr/day |

Rather than measuring or using microamp hours µA-hr for monitoring usage, an arbitrary capacity count unit would be more efficient since digital devices are best if they can keep simple counts and do not need to perform large amounts of multiplication and division. As part of the process 400, energy usage in capacity count units or units per timer period would be computed for functions 1-5 in sub-process 410.

In overall concept, the system operates to calculate a number of dimensionless relative power capacity count units, namely $U_{BAC}$, $U_E$, $U_{VR}$ for calculation of a relative capacity count. Power usage for each function (such as background usage, telemetry usage, and vibrator usage) is initially measured prior to implant of the IMD 10. In an embodiment, the measurements of each function should occur during device development, for example in the final verification and validation testing of the manufactured IMD 10. Further, a preset power conversion unit is determined to be applied to the obtained power usage of each function. This power conversion unit is an arbitrary predetermined number having the dimensions of power per time interval.

The $U_{BAC}$ is defined as the relative background power capacity unit and is associated with the background power usage of the IMD 10. This background power usage may be the battery power used during a specific time interval where IMD 10 is not activating components within the IMD 10. This may be during what is generally termed a "sleep mode" of the IMD 10. An incrementing factor of $U_{BAC}$ is then calculated by taking the time interval that the IMD 10 is in a background mode and dividing the background power usage in the time interval by the power conversion unit. The dimensionless $U_{BAC}$ is calculated by initially setting a counter within IMD 10 to zero and incrementing the counter during the background time interval by the incrementing factor.

The $U_{VR}$ is defined as the relative vibrator and telemetry subsystem power capacity unit and is associated with the power usage of the vibrator 25 within the IMD 10 and the telemetry subsystem 46. An incrementing factor for the vibrator power usage of the vibrator 25 is then calculated by taking the time interval that the vibrator 25 of the IMD 10 is activated and dividing the vibrator power usage in the time interval by the power conversion unit. A dimensionless vibrator power usage is calculated by initially setting a counter within IMD 10 to zero and incrementing the counter during the vibrator activation time interval by the incrementing factor to obtain an intermediate relative capacity count $U_V$ associated with the vibrator 25 activation. An incrementing factor for the telemetry subsystem power usage of the telemetry subsystem 46 is then calculated by taking the time interval that the telemetry subsystem 46 of the IMD 10 is activated and dividing the telemetry subsystem power usage in the time interval by the power conversion unit. A dimensionless telemetry subsystem power usage is calculated by initially setting a counter within IMD 10 to zero and incrementing the counter during the telemetry subsystem 46 activation time interval by the incrementing factor to obtain an intermediate relative capacity count $U_R$ associated with the telemetry subsystem 46 activation. Finally, $U_{VR}$ is calculated by adding $U_V$ to $U_R$ to provide the relative capacity count associated with the vibrator activation usage and the telemetry subsystem activation.

The $U_E$ is defined as the relative data collection power capacity unit and is associated with the number of electrogram segments power usage collected during a predetermined time interval within the IMD 10. This data collection power usage may be the battery power used during a specific time interval for a specific number of data segments collected by the IMD 10. An incrementing factor of $U_E$ is then calculated by taking the number of electrogram segment data during a time interval that the IMD 10 and dividing the data collection power usage during the time interval by the power conversion unit. The dimensionless $U_E$ is calculated by initially setting a counter within IMD 10 to zero and incrementing the counter during the data collection time interval by the incrementing factor.

A cumulative relative power capacity $U_{CUM}$ is calculated by the equation $U_{CUM}=U_{CUMPRIOR}+U_{VR}+U_E\pm U_{BAC}$.

For the example above, 36 µA-hrs per usage count might be selected. Consequently, the estimation count was incremented by: 7 (251/36=6.97≈7) at midnight to account for background consumption; 1 (33+2/36=0.97≈1) at midnight for every 512 segments collected the previous day plus the hourly and daily periodic processing; 1 (43/36=1.19≈1) every 10 seconds that there is an active communications session; 3 (110/36=3.06≈3) every 10 seconds while the motor is vibrating with an Emergency Alarm (approximately 20 pulses per 10 seconds)

With this approach, at any given time in the life of the device, multiplying the estimation counter value by 36 and dividing by 1000 would be an estimate of mA-hrs consumed so far.

Also, as part of process 400, the relative capacity units used for each function would be included in sub-process 412 and stored in the program parameters memory 475 of the memory 47 of FIG. 4.

Next in process 400 is to determine the battery capacity in sub-process 415 in milliamp hours (mA-hrs). From this a battery EOS with just enough left to alert the patient is computed in sub-process 420 at a pre-set percentage of the total battery capacity. This number should represent a conservative estimate of the capacity the battery can provide while maintaining a voltage (just) above the input requirement of the voltage regulator circuit to keep the IMD 10 alive.

For example, if the battery is 2,000 mA hours, 90% might be selected as the EOS preset threshold. This threshold is first computed in mA-hrs then converted to the relative capacity units creating the EOS capacity threshold $U_{EOS}$ in terms of the relative capacity units.

Next in sub-process 425 one would compute the ERI threshold $U_{ERI}$ in relative capacity units to allow a selected number of days of additional cardiac monitoring and optionally, the addition of providing at least one emergency alarm before EOS. This provides an added safety margin as it can take a month or more for the patient to arrange to get a replacement device. For example, one might like to have 45 days of use before EOS to allow scheduling and completion of IMD device replacement.

Finally, in sub-process 430, the capacity threshold for EM is included in the IMD 10 memory 47 for $U_{ERI}$ 482 of FIG. 4.

With 6 months being the typical patient follow-up interval for the ACMS 100 of FIG. 3, alerting for battery EOS is important. This differs from modern day pacemakers typically upload data on a more frequent basis. The present invention ACMS 100 is configured to use either or both measured voltage and calculated capacity methods and would alert the patient with a See Doctor alert upon detecting ERI. If action is not taken an additional See Doctor Alert could be provided at upon detection of EOS.

The above scenario assumes normal functioning of the device. Various unlikely though possible fault scenarios can result in the battery being depleted sooner than expected. In such cases, the calculated capacity estimation offers less value. However, voltage measurements will help to provide an advantage of the dual monitoring scheme.

Figure 7:
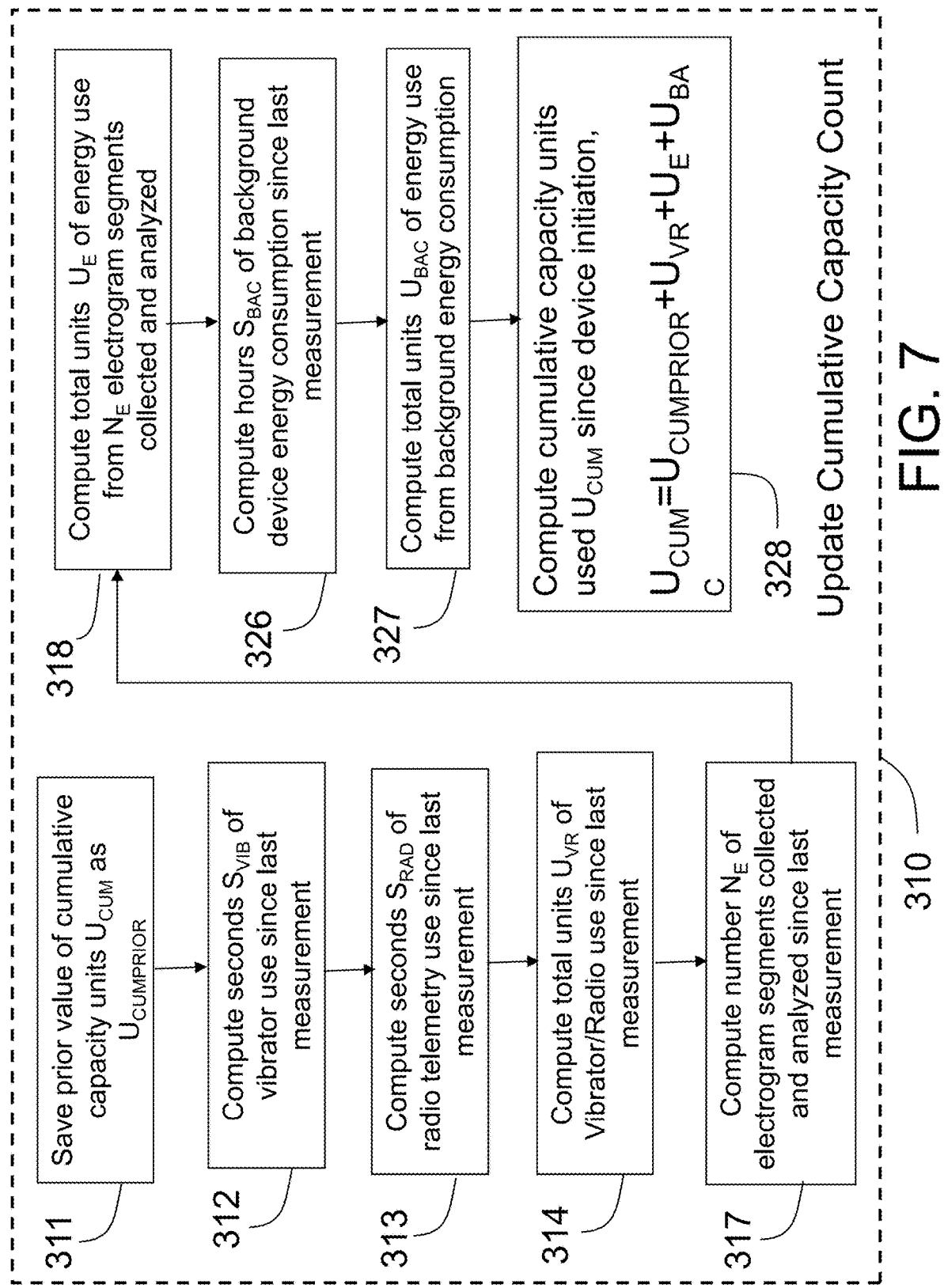
FIG. 7 shows the steps in the process of FIG. 5 for updating the Cumulative Capacity Count $U_{CUM}$.

FIG. 7 is a flow chart showing the detail of the process step 310 of FIG. 5 for updating cumulative capacity count $U_{CUM}$.

The process step 310 begins in step 311 where the prior value of $U_{CUM}$ is saved as $U_{CUMPRIOR}$.

Next in steps 312 and 313, the time of use of vibrator and telemetry radio since the last update are computed and in step 314, are converted into the relative capacity count units and combined into the vibrator/radio use count $U_{VR}$.

Next in step 317 the number of electrogram segments collected and analyzed $N_E$ since the last update is computed and in step 318 this usage is converted into relative capacity count units $U_E$. This might also be estimated by multiplying the hourly or daily typical number of segments collected by the number of hours or days since the last update.

Next in step 326, the hours of background device energy consumption since the last update is computed and in step 327 this is converted into relative capacity count units $U_{BAC}$. Steps 317, 318, 326 and 327 can be simplified if the updates are done on a regular basis where the capacity units $U_E$ and $U_{BAC}$ are the same every time and no computing is needed. For example, the ideal update period is once per day when many other functions of the IMD 10 of FIG. 3 are updated.

Finally, in step 328, the updated cumulative capacity unit value $U_{CUM}$ is calculated using the formula $U_{CUM} = U_{CUMPRIOR} + U_{VR} + U_E + U_{BAC}$. $U_{CUM}$ can then be returned to the ERI process 300 of FIG. 5 where it is compared to the ERI value $U_{ERI}$ to see if it is time to notify the patient to seek device replacement.

FIG. 8 shows detail of the EOS process 330 of FIG. 5 that would occur after either of the voltage or capacity methods for determining ERI has triggered a patient alert. This strategy allows the IMD 10 of FIG. 4 to operate with battery voltage and capacity use being tested as until the patient can get a replacement device or the EOS thresholds are reached which triggers a final alert before the device goes to the end of life (EOL) process 340.

The process 330 like the ERI process 300 of FIG. 5 operates in the primary operating loop within the IMD 10 firmware/software, or occurs as a part of an already scheduled event such as once an hour baseline data collection or once a day creation of new histograms or is invoked after every seventh histogram is created. Either way, the process 330 evaluates if it is time to check the battery voltage in step 331, if it is not time it waits for the next time through the loop or for the next scheduled event. This too can also be accomplished by a timer interrupt to the IMD CPU 44 as described for the ERI process 300.

If it is time to check the battery status, then in step 333, the process 330 has the IMD CPU 44 of IMD 10 in FIG. 4 turn on a load so that the battery voltage monitor 23 of FIG. 4 can be measure the voltage under load. The battery voltage under load is then measured in step 334 and the load is turned of in step 335 to minimize power use. In one embodiment, multiple voltage measurements are made and all or some of the measured voltages are averaged together.

Step 336 then compares the measured (or averaged) battery voltage $V_{BAT}$ to see if it is below (less than) the pre-set EOS replacement interval battery voltage threshold $V_{EOS}$. If the measured battery voltage $V_{BAT}$ is below (less than) the $V_{EOS}$ the process 330 proceeds to step 339 to alert the patient with a See Doctor alert and then proceeds to the end-of-life process 340 shown in FIG. 9. $V_{EOS}$ is determined during product development and testing to be the battery voltage indicative of sufficient capacity remaining to initiate a single patient alert for the need for battery replacement.

If the measured battery voltage $V_{BAT}$ is not below (less than) $V_{ERI}$, the process 330 continues update the cumulative battery usage counter in process step 310. Details of process step 310 are shown in FIG. 7. After updating the cumulative battery usage count in process step 310, the process 330 proceeds to step 338 to check if the device is in need of replacement based on the battery capacity count.

Figure 9:
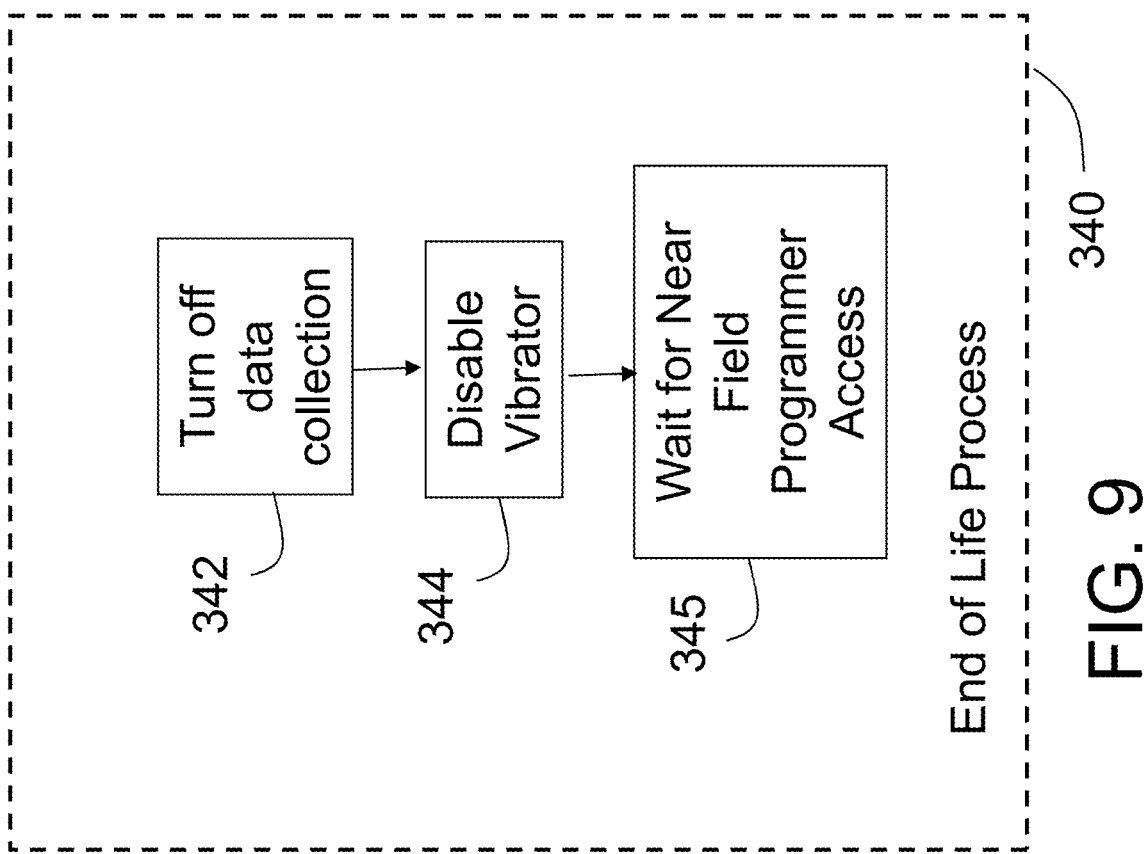
FIG. 9 is a flow chart showing the process implemented at device end of life.

In step 338 if the updated battery usage cumulative capacity count $U_{CUM}$ is greater than the preset EOS usage count threshold for cumulative battery use $U_{EOS}$ the process 330 proceeds to step 339 to alert the patient with a See Doctor alert and then proceeds to the end-of-life process 340 shown in FIG. 9.

If the updated battery usage cumulative capacity count $U_{CUM}$ is not greater than the preset battery replacement count threshold for cumulative battery use $U_{EOS}$ the process 330 then proceeds to step 346 where the time for battery check T is increased by H hours and the process 330 returns to operating within the main loop of the IMD CPU 44 of FIG. 4 or being triggered by a scheduled event or clock interrupt.

It is envisioned that $H_{EOS}$ can be a time of between 1 hour and 320 hours (1 month) with the preferred being 24 hours. As other functions of the IMD 10 occur once a day, this allows the timer register T to be used for multiple functions. It is envisioned that $H_{EOS}$ could be shorter than H used in the ERI process 300.

The pre-set values $U_{EOS}$, $V_{EOS}$, $H_{EOS}$ and other parameters or stored in the Programmer Parameters Memory 475 section of the memory 47 of FIG. 4.

FIG. 9 shows the end-of-life process 340 that is implemented once there is no longer energy left in the battery to power any additional patient alerts. It is put in place so that there is hopefully sufficient energy remaining for a final communication session with the ACMS physician's programmer 140 of FIG. 3.

Process 340 begins by discontinuing all data collection in step 342, disabling the vibrator 25 of FIG. 4 in step 344 so it cannot be turned on. The final step 345 is to minimize all power use other than to periodically look for programmer access through the near-field signal sensor 90 with antenna/coil 91 of FIG. 4.

While it envisioned in one embodiment of the present invention that one could use only the EOS voltage and capacity thresholds to alert the patient when there is just enough energy for a single patient alert, it is desirable to alert the patient days or weeks before EOS just to be sure there is both enough energy left to sound the alarm and to keep the monitor going until the patient can schedule a replacement implant. This is why the preferred embodiment, uses the ERI thresholds $U_{ERI}$ and $V_{ERI}$ to alert the patient a desired number of days before EOS would occur.

The dual method described here is likely to be the best way to prevent the end of life happening without the patient being notified.

In an embodiment where a rechargeable battery is used by a component of the system such as the IMD. In this instance, the ERI indicator can be used as a proxy for a recharge-necessary indicator (RNI). The RNI level may be set to provide residual capacity such as a level of remaining power that allows two days of operating power or sufficient power to provide two additional emergency alarms. Additionally, the RNI may cause the system to operate so that it will only issue Emergency alarms or See Doctor alarms or both via the EXD 120 to conserve power. The RNI alert may be defined for the IMD 10/EXD 120 or both, and an RNI log may be created to determine patient compliance with respect to recharging the IMD without allowing the power to fall below a level that is sufficient to provide continued operation.

Figure 10:
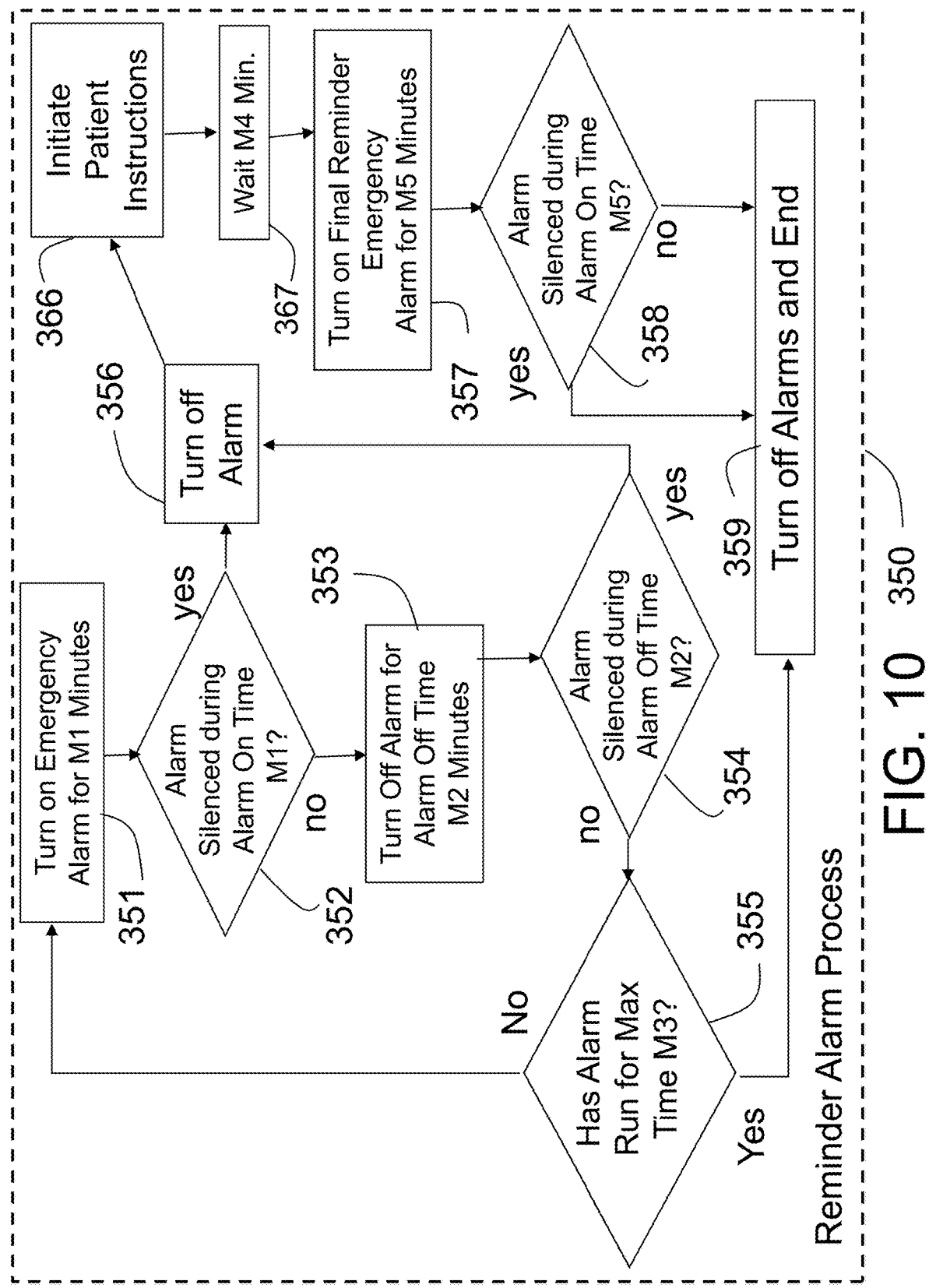
FIG. 10. is a flow chart showing the process for providing reminder alarms.

FIG. 10. is a flow chart showing the process 350 implemented in the program memory 45 of the IMD CPU 44 of the IMD 10, SSMD 800 or SCM 900 of FIG. 4 for providing an Emergency Alarm with reminder alarms if the patient silences the alarm or fails to do so.

In embodiments, the ACMS 100, IMD 10 or SCM 900 of FIG. 3 detects the occurrence of an event that has been defined as requiring an alert be provided to the patient. The ACMS 100 provides a first alarm to notify the patient. If defined for the event, then at least one additional reminder alarm is provided at a preset delay after either the initial alarm or the patient acknowledgment/silencing of the initial alarm using the EXD 120 of FIG. 3. The attributes for the reminder alarm are defined for the alerted event type and may be provided by the EXD 120, the IMD 10 or SCM 900, and/or other ACMS 100 system component.

Reminder alarms can also be silenced. Patient acknowledgement of alarms, and tracking of such acknowledgement in an EXD log, is useful in assessing compliance in the long-term management of high-risk patients in a home or ambulatory environment. Additionally, the EXD 120 is provided with an alarm module managed by the EXD CPU 130 of FIG. 3 that is configurable by the patient or doctor to increase the number of reminder alarms that will occur in addition to the first alarm. When the EXD 120 or a smart device 225 of FIG. 3 operates with a home base station that can communicate with a remote center, then a remote telemedicine session may be also defined to launch as part of the reminder alarm.

In FIG. 10, the reminder alarm process 350 begins after an Emergency Alarm is initiated in step 351 for an Alarm On period of M1 minutes which will alert the patient in a pattern of bursts of vibrational pulses from the IMD 10 and/or acoustic and visual alerts from the EXD 120 of FIG. 3.

Next, in step 352 the near-field signal sensor 90 will be checked periodically by the IMD CPU 44 of the IMD 10 of FIG. 4 during the Alarm On period to determine if the EXD 120 of FIG. 3 has been placed in the near-field and then the near-field signaling system 133 has been activated by the user pressing the alarm silence button 122. If no button press has been detected, alerting will be turned off for the Alarm Off period of M2 minutes in step 353. Step 354 will continue to monitor for the occurrence of an alarm silence signal to be transmitted from the EXD 120 during the M2 period which would indicate the user had pressed the alarm silence button 122.

If the Alarm silence signal is provided during either Step 352 or 354 the process 350 will turn off the alarm signal in step 356, then in step 366 may provide additional instructions to the patient before waiting a duration of M4 minutes in step 367 then initiating a Final Reminder Emergency Alarm in step 357 for an Alarm On duration of M5 minutes. If the Final Reminder Emergency Alarm is either silenced by a user during the M5 minutes or continues for the entire M5 minute duration, then the alarm signals will be disabled and the process 350 till terminate in step 359.

In embodiments, if only the EXD 120 provides a reminder alarm then the processor of the EXD 120 can operate software which is programmed to provide one or more reminder alarms without requiring the IMD 10 to send another alert trigger to the EXD 120 (to save power). Further, reminder alarms can be defined to occur contingently by software operated by the processor of the EXD 120. For example, if a patient does not silence the initial alarm then the reminder alarm be defined to occur after a shorter duration and at a louder intensity than the initial alarm.

There are a wide range of possible patient information such as patient instructions or guidelines that can be provided by step 366. This information can be related to one or more of the following actions: 1) Taking or injecting one or more medications prescribed or suggested by the patient's doctor—for example chewing an aspirin can have a significant benefit during a coronary occlusion caused by a blood clot; 2) Calling a phone number to speak to a medical professional or caregiver; 3) Performing a physical action, for example, lying down or raising one's legs above one's body.

The patient information may be provided by one of the following: 1) by the EXD 120 through incorporation of voice announcement or a text display; 2) through a verbal or text message sent to the patient's or caregiver's home base station, tablet or smartphone using standard messaging techniques and/or using the SDAPP 220 of FIG. 3., and/or; 3) by a phone call to the patient or care giver with an announcement placed to a voice telephone; or 4) by a skype, zoom, facetime or other video call placed to the patient's smart device 225 that may be also incorporated into the SDAPP 220.

If the alarm is not silenced by a user in either step 352 or step 354, then step 355 will check if the maximum duration M3 for an unsilenced emergency alarm has been met or exceeded. If the M3 duration has not been met or exceeded then the process 355 will return to step 351 and activate the Emergency Alarm for a duration of M1 minutes. If the maximum duration has been met or exceeded then the process will terminate in step 359.

Examples of M1, M2, M3, M4 and M5 are as follows: M1 might be between 5 seconds and 30 minutes; M2 might be between 30 seconds and 30 minutes; M3 might be between 5 minutes and 24 hours; M4 might be between 5 minutes and 1 hour; M5 might be between 15 seconds and 30 minutes.

For example, the Emergency Alarm could be realized using an international standard for Emergency signals which comprises of 5 pulses repeated in pattern of 3-2 for an M1 period of 5 minutes, then off for an M2 period of 15 minutes and kept going for an M3 period of 2 hours. If silenced during the M3 period, the process 350 could wait an M4 period of 15 minutes then reactivate the Emergency Alarm for an M5 duration of 30 seconds unless silenced.

FIG. 11 is a table 500 showing the structure of a portion of an R-R interval and heart rate histogram data memory 473 of FIG. 4 for a single data collection interval. The term "data collection interval" is defined as the time during which the IMD 10, SCM 900 or SSMD 800 of FIG. 3 will be updating a specific histogram. The data collection interval could be as short as a minute and as long as many months. Additionally, several data collection intervals may be used and related to each other. For example, daily histograms can be used to generate weekly histograms or monthly histograms. In a preferred embodiment tracking a patient's daily heart rate profile, an hourly data collection interval is used to provide 24 histograms per day. That is a small amount of data. For example, the histogram table 500 of FIG. 11 has 16 bins that at two bytes of data per bin needing only 32 bytes per histogram or 24×32=768 bytes per day, 23K bytes per month and 276K bytes per year. This is an efficient way to store this data and 2 bytes of data per bin will allow counts of up to ~65 thousand.

In an embodiment, R-R interval/heart rate histograms are stored in the R-R interval Histogram memory 473 of the IMD 10. This heart rate tracking capability using histograms is a desirable feature in addition to the ability of the IMD 10 to detect acute heart rate abnormality events such as High, Low and Irregular heart rates described in the prior art.

As an example, the histogram table 500 of FIG. 11 has 4 rows, the bin number 504 in row 1, the values for the number of beats 502 for a particular bin in row 2, the heart rate range 506 in row 4 and the corresponding RR interval range maximum 508 in row 3. Only the actual number of beats data is stored in the R-R interval histogram memory 473 while the ranges are preset (for all patients or can be specific to each patient) in the program parameters memory 475 of FIG. 4.

Histogram data can be combined to evaluate or present views of heart rate/R-R distributions over days, weeks, months or years as a feature of the physician's programmer 140 and SDAPP 220 of FIG. 3 to select how and which data is combined to best help a clinician understand changes over time and provide insights as to what is going on in a patient's heart.

Figure 12:
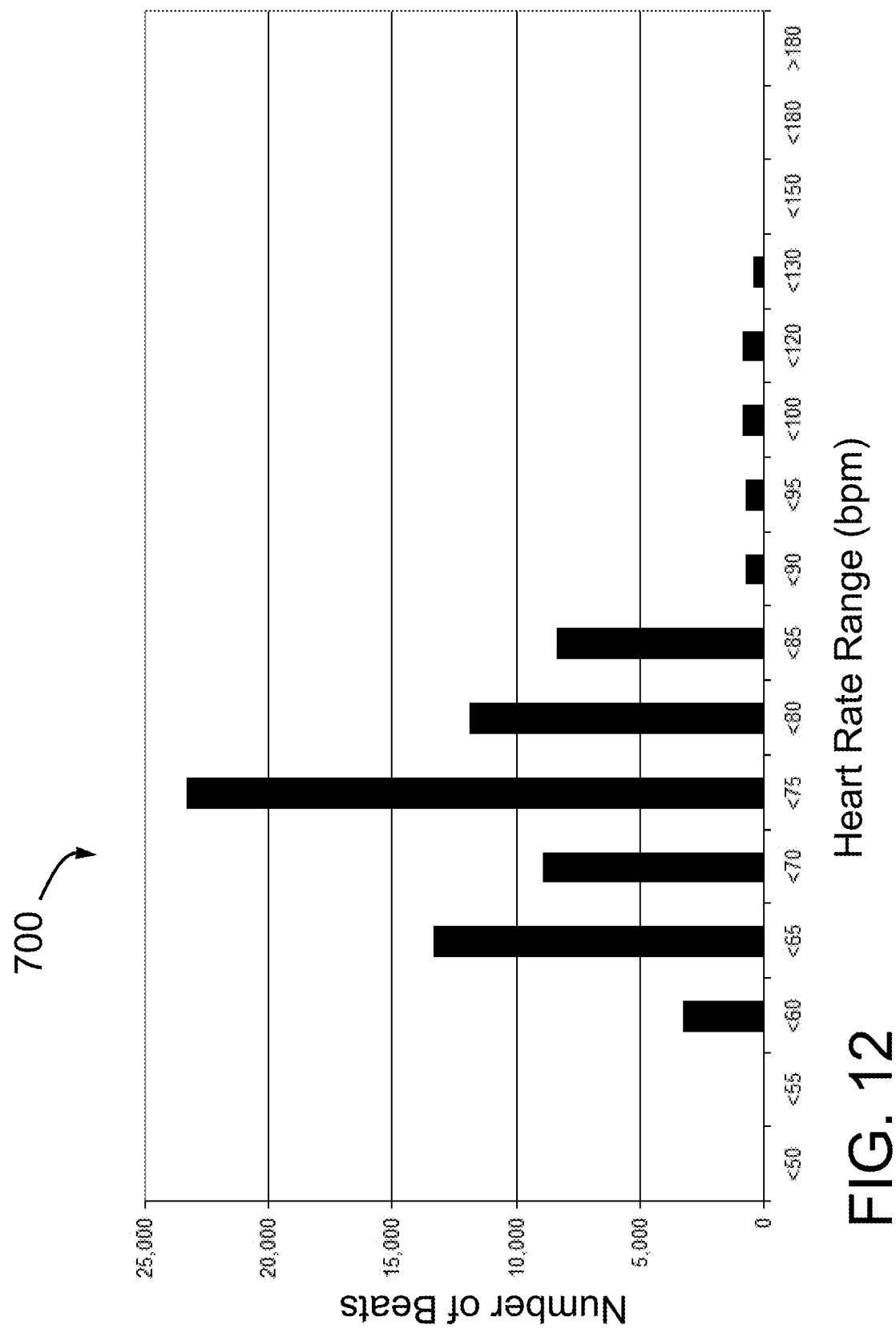
FIG. 12 is an example of the plot of the R-R interval histogram data for a day.

FIG. 12 is an example of the present invention display screen implemented on the physician's programmer 140 or the SDAPP 220 of FIG. 3 showing a two-dimensional histogram plot 700 of heart rate captured over a week interval. It is envisioned that such plots would be the result of combining a week's worth of hourly histograms to help a medical professional identify anomalies over longer periods of time of weeks, months or more. For example, a new incidence of many beats below 50 bpm could indicate need for a pacemaker. A new incidence of beats above 160 bpm could indicate the need for an anti-tachycardia pacemaker. If no beats are above 90 bpm for a week, the patient may need to be encouraged to exercise. A selected number or percentage of beats with R-R intervals corresponding to an elevated heart rate range (e.g., between 100 and 150 BPM, or otherwise set by a user or device algorithm) could indicate a compliance issue or need for a dose change of the patient's beta blocker prescription.

Furthermore, the IMD 10 of FIGS. 3 and 4 can process histograms to compute extracted histogram data including statistical data such as: 1) the median, mean, maximum and minimum heart rate or R-R interval for each histogram; 2) the standard deviation of the histogram distribution with respect to the highest value bin or with respect to the mean or median; 3) the number of beats per hour, day, week or month per histogram exceeding a pre-specified threshold of R-R Interval or heart rate; 4) The moving average over two or more data collection time periods of any of items 1 through 3.

In embodiments, extracted histogram data is compared by the IMD 10 with a pre-set or machine learned detection threshold for ST-segment ischemia detection or other cardiac measure. If a threshold is exceeded for a selected number of segments or time period, the IMD 10 can perform operations including: alerting the patient by means of a SEE DOCTOR ALERT or EMERGENCY ALARM; transmitting the event and/or associated data through the EXD 120 to an External Support System (ESS) 240 for storing of historical records or later clinician review; transmitting the event and/or associated data through the EXD 120 to a medical practitioner or care-giver who would have access through the SDAPP 220.

Histogram data, summary statistics, and extracted histogram data and other data in the IMD 10 may be uploaded to the ESS 240 through the EXD 120 on a periodic basis. The EXD 120 is continuously or periodically operating its communication circuitry to receive signals if they are transmitted from the IMD 10 which is programmed to turn on its telemetry sub-system 46 and connect thru the EXD 120 to transmit through the voice/data network 250 to the ESS 240.

In embodiments, the IMD 10 processor is configured to compare changes in extracted histogram data between two time periods to detect a change that is defined to trigger any of the above operations. Changes can be evaluated using one or more comparison thresholds which are used to evaluate the comparison of one or more features of a histogram or features calculated therefrom. For example, shape of the histogram can be compared using a "broadness", skewness, asymmetry above and below the median, or other variance of two histograms which are compared to threshold values.

The physician's programmer 140 of FIG. 3 allow for programing to define or select the heart signal parameters that will be tracked using the histogram technique. It is also envisioned that the physician's programmer 140 will be able to process the histogram data downloaded from the patient's IMD 10 of FIGS. 3 and 4 to suggest detection thresholds for the detection by the IMD 10 of future cardiac events that warrant patient notification or other operations.

In an embodiment, populating the histogram 700 of FIG. 12 is accomplished as follows:

1. The IMD 10 of FIG. 4 will capture an electrogram segment N seconds long every M seconds (or minutes) and measure the R-R intervals for each beat. For example, a sensing protocol which senses a 10 second electrogram data segment every 90 seconds is established.

2. A new histogram with B bins is created every K minutes and the prior histogram saved for a preset retention period (which can be very long since the memory use of these histograms is small). For the new histogram each time a beat with an R-R interval occurs over the K minutes the IMD CPU 44 of FIG. 4 will increment by one (1) the value in the histogram bin corresponding to the R-R interval range associated with the measured R-R interval of the electrogram segment. The bins may alternately correspond to a heart rate range with associated R-R interval range.

For example, FIG. 11 shows a table 500 representative of a histogram with 16 bins (0-15) in line 504 with 16 R-R interval ranges 508 with corresponding heart rate ranges 506. As mentioned in the prior example, a histogram table such as this might be created every 60 minutes (i.e., K=60.).

The value of being to track a patient's heart rate over days, months or years can be of great value in reflecting heart function status or change in status, and for diagnosing heart rate anomalies such as arrhythmias or issues with beta blocker compliance or dosing.

Similar histograms could be used to track other heart signal parameters including: 1. ST segment voltage 2. ST deviation (ST segment amplitude minus PQ segment amplitude for a single heart beat), 3. R-R interval (time period between successive R waves), 4. R-R interval variability, 5. R peak height, 6. R wave width 7. QRS voltage, 8. QRS width, 9. RS width, 10. T wave width and/or amplitude, 11. T wave alternans, and 12. QRS shift (a recent average value of QRS voltage over a data collection time period minus the baseline QRS voltage where baseline QRS voltage is the average value of the QRS voltage for a multiplicity of heart beats at a time when the heart of a heart transplant patient is not undergoing rejection).

Figure 13:
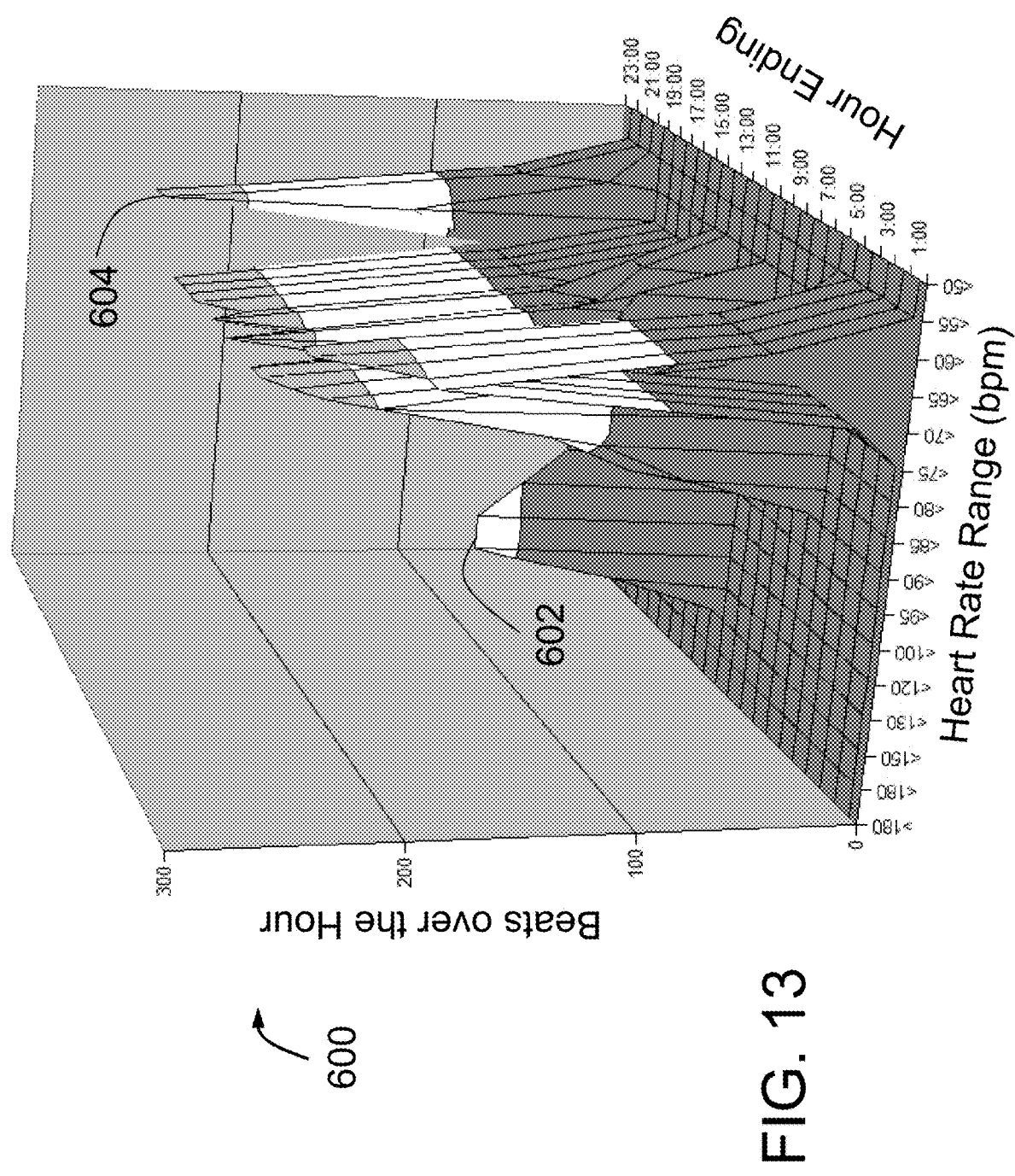
FIG. 13 is an example from a present invention display screen implemented on the programmer of FIG. 3 showing a surface graphical plot of the R-R interval data for a patient with 1 hour data collection time intervals.

The present invention IMD 10 of FIGS. 3 and 4 analyzes processed heart signal parameter data including that stored as histograms and statistical data extracted from the heart signal parameters and statistical data extracted from the histograms to identify changes in cardiovascular condition over time periods of days, weeks, months or even years. The statistical data is valuable for identifying cardiac events, for example such as detecting when a median heart rate exceeds a 100-bpm value for a number of hours. The histogram data can also be displayed for human analysis by the patient's physician using analysis tools provided in the ACMS physician's programmer 140 or the SDAPP 220 of FIG. 3. Such displays can be for individual or combined histograms such as that shown in FIG. 12 or a surface plot such as shown in FIG. 13.

Returning to FIGS. 3 and 4, an exemplary embodiment of a system for alerting patients to a potential heart attack by identification of excessive ST shift from the heart signal of a patient is shown. As seen in FIG. 3, a pair of electrodes 112, 115 are connected to an IMD 10 containing a vibrator 25 or some other alerting mechanism. Electronics within the IMD 10 are electrically coupled to the electrodes 112, 115. The IMD 10 contains a processor 44 with associated digital memory adapted to compute the values of the ST deviation and the ST shift. ST deviation is the difference between the average values of a portion of a ST segment and a portion of the PQ (or PR) segment of a beat of the heart signal sensed by the two electrodes 112 and 115. ST shift is the change in ST deviation compared to baseline ST deviation normalized to the average baseline heart signal amplitude for a multiplicity of beats sensed by the two electrodes 112, 115. The processor 44 is adapted to save in memory the values of ST deviation for a pre-set data collection time period. The collected data provides the distribution of ST deviation over the data collection time period. The ST deviation distribution has a mean, a median, a positive (values greater than zero) portion and a negative (values less than zero) portion.

A positive standard deviation is computed by creating a first symmetric distribution by mirroring the positive portion of the ST deviation distribution about a central value. The central value may be the mean of the distribution, the median of the distribution, or a zero ST deviation value. A negative standard deviation is computed by creating a second symmetric distribution by mirroring the negative portion of the ST deviation distribution about a central value. Again, the central value may be the mean of the distribution, the median of the distribution, or a zero ST deviation value.

The system calculates positive and negative ST deviation thresholds. The positive ST deviation threshold is the central value of a ST deviation distribution histogram plus a multiple of (e.g., at least two) positive standard deviations. The negative ST deviation threshold is the central value of the ST deviation distribution histogram minus a multiple of (e.g., at least two) negative standard deviations.

The system further calculates positive and negative excessive ST shift detection thresholds as the respective positive and negative ST deviation thresholds normalized to an average heart signal amplitude captured during the data collection time period.

In a preferred embodiment the ST deviation data is stored in one or more histograms and the positive and negative excessive ST shift thresholds are computed from the positive and negative portions of one or more of the histograms.

The processor activates the patient alerting mechanism based on either the positive or negative excessive ST shift detection thresholds being exceeded by the ST shift for a multiplicity of beats of the patient's heart signal.

Techniques to capture electrogram data and heart signal parameter data computed from electrogram segments over days, weeks or months are important because, some of the processes of heart malfunction are gradual. It is desirable to detect and treat such conditions before the onset of an acute event such as an AMI, heart failure onset, ventricular ejection fraction decrement, or ventricular fibrillation or the complete rejection of a transplanted heart. Use of histograms helps to limit the amount of memory and electrical power needed in the IMD 10, SSMD 800 or SCM 900 of FIGS. 3 and 4, to collect, store and analyze the heart signal data looking for trends is especially important in implantable and portable systems.

FIG. 13 is an example of a present invention display or data print out implemented on the physician's programmer 140 or SDAPP 220 of FIG. 3 showing a surface graphical plot 600 of 24-hourly data collection time interval heart rate histograms similar to that of the table 500 of FIG. 11. Two features are of interest in this plot. The first is a period of elevated heart rate 602 between 11 am and noon. This could correspond to the patient exercising. In an embodiment of the IMD 10, an IMD accelerometer 75 of FIG. 4 is provided, to provide data that can displayed with elevated heart rate data to help differentiate elevated heart rate from exercise vs. elevated heart rate data from issues with beta blocker dosing or medication non-compliance.

Data from the IMD accelerometer 75 of FIG. 4 may also be used to create separate histograms that are for higher heart rates related to exercise. These histograms can be used to enable the IMD 10 to provide historical records akin to "stress tests" data, showing distributions of heart rates and ST changes for those heart rates during exercise. In this manner the system can be tailored to provide stress tests results in addition to monitoring for ACS events which occur during the normal heart rate range.

In an embodiment, the patient can press a button (not shown) on the EXD 120 of FIG. 3 labeled "stress test" before pursuing a period of exercise and the IMD 10 of FIGS. 3 and 4 operates in stress-test mode according to a stress test protocol operated by the EXD CPU 130 in order to collect ST segment data over a range of heart rates. The stress test data (e.g., raw ECG waveforms, histogram data, summary statistics) that is collected during the stress-test mode is stored in event memory 474 of the IMD 10 that is allocated for stress test result data so that it does not contribute to the standard histograms data stored in the IMD 10. The patient exercises during the stress-test until the IMD 10 sends a signal to the EXD 120 that indicates the stress test is over causing the EXD 120 to emit a series of beeps to alert the user.

Additionally, the EXD 120 can operate in a "Stress Test" mode which includes toggling a stress test LED (not shown in FIG. 3) on an on state to indicate a stress test is occurring and then transmitting the stress test data to a central station as the end of the stress test. Rather than using the EXD 120, the SDAPP 220 of FIG. 3 running on the patient's smart device 225 could provide appropriate instructions and notifications to structure the stress test.

Further, the EXD 120 or SDAPP 220 can instruct the patient to increase or decrease their exercise level to attain heart rates in selected ranges during this stress test protocol under the guidance of a pulse oximetry device.

The SDAPP 220 can initiate an "end stress test" command to through the EXD 120 to the IMD 10 when a sufficient amount of data at different heart rates indicates the IMD 10 heart rate histogram has sufficient data.

In an embodiment, the SDAPP 220 asks the patient if they are running on a treadmill or riding a stationary bike or walking up stairs or doing a different activity and then performs a stress test by presenting the patient with a virtual program for biking or running on a treadmill which makes the exercise more engaging and fun for the patient.

The EXD 120 or SDAPP 220 can transmit the stress test dataset collected by the IMD 10 to a remote center for review or store the data for upload to a physician's programmer 140 of FIG. 3 on a future clinic visit. Even if the stress test data are transmitted, the IMD 10 can be given sufficient memory that it retains certain stress tests data such as summary statistics in its memory in order to retain a history more than one stress test session result. The stress test dataset would include ST-level values as a function of HR as well as samples of the raw electrogram segments collected at different heart rates and the stress test continues until a minimum number of heart beats have populated each of the histograms or a maximum time limit has occurred. After the stress test data are transmitted to remote center, a medical professional at the remote location can then compare the current stress-test dataset to one or more stress test datasets of the patient that were collected previously to assess if there has been a change in the patient's heart health.

In an embodiment, the physician's programmer 140 and/or SDAPP 220 would have the capability to display a graph of the stress test duration showing heart rate and ST deviation of shift.

In an embodiment the stress test design can be based the patient's characteristics. For example, if the patient is older maybe the test is shorter, or the target heart rate criteria are lower and customized in the tablet that is running the test.

Another important feature shown in FIG. 13 is, the drop in heart rate 604 beginning at 10 pm (22:00) is an indication of the patient going to sleep. This low heart rate period extends until around 7 am when the plot shifts to higher heart rates after the patient is awake. These data can be used to monitor patient sleep as well as if the patient is getting up frequently during the night. Further, in patients with sleep apnea (obstructive or central), summary statistics, histogram, and raw electrogram segment data can be used to assess the effects of sleep disorders on cardiac activity and ischemic burden.

Collection of data by the IMD 10 that allow waterfall plots to be generated by the physician's programmer could be very useful to the patient's doctor with respect to diagnosing episodes of arrhythmias. For example, an elevated heart rate (such as 602) for 3 or more hours could be an indication of beta blocker improper compliance or dosing. If the heart rate elevated above 160 bpm it might indicate an episode of tachycardia. Similarly, an extension of the surface to the right along the heart rate value axis can detect episodes of bradycardia. A widening of the daily distribution of heart rate values could be an indication of irregular or unstable heart rate that is indicative of change in cardiac health status or onset of atrial fibrillation. In an embodiment, data which is sufficient to generate a waterfall plot over a 1-2 day period is collected by the IMD periodically (e.g. once every 2 months), and stored in the IMD 10 for future download such as may occur every 6 months during a visit to the patient's cardiologist. The waterfall plot data may be stored for heart rate, ST shift, and any other measures collected by the IMD 10.

FIG. 14 is a schematic view of a SSMD 800 that can be realized as a form factor that is worn on a patient such as a strap on vest including the vest 802 with buckle 804. In the shown embodiment, there are three electrodes 822, 823 and 824 that are located under the vest in contact with the patient's skin. Hopenfeld et al in U.S. Pat. Nos. 8,560,055, 8,682,422 and 9,375,151 describes an exponential averaging technique for ST monitoring that can identify occlusions of all three major coronaries when implemented with three electrodes as shown here. These include an electrode 822 in the upper left chest, 823 at the patient's sternum and 824 below the ribs on the patient's left side. These are known to allow two nearly perpendicular vectors for assessing ST changes with the first vector being from electrode 822 to 823 and the second vector being from electrode 823 to 824.

In this embodiment these electrodes would be connected through the cables 832 and 834 to a monitoring electronic device 820 which may be the SSMD 800 shown in FIG. 3. The monitoring electronic device 820 is envisioned to be able to include the features and capabilities of the ACSM 100.

The SSMD 800 and vest 802 could be configured in different sizes and shapes to accommodate men and women of different sizes. The use of the sternum of electrode 823 makes it possible to have the SSMD 800 place the electrode 823 and cable 832 between a woman's breasts. Ideally, the shape of the vest 802 as shown in FIG. 14 should route from the shoulder area along the clavicle and then down to the sternum since this will avoid women's breasts and problems due to movement of the shoulder.

Most of the features of the IMD 10 and EXD 120 of FIGS. 3 and 4 could be combined in the SSMD 800 which would not need a separate EXD as it is outside of the patient's skin and can easily have direct access to the cellular network, Bluetooth to pair it with a smart device 225 of FIG. 3 or local Wi-Fi. The SSMD 800 could therefore also include an alarm silence button and/or an event tagging/panic button 826.

It is also envisioned that an implantable version of the SSMD 800 could be implemented with tunneled leads under the skin or a combination of subcutaneous and wearable components. In one embodiment, the external components could be implemented to provide inductive power transfer to the subcutaneous components.

Figure 15A:
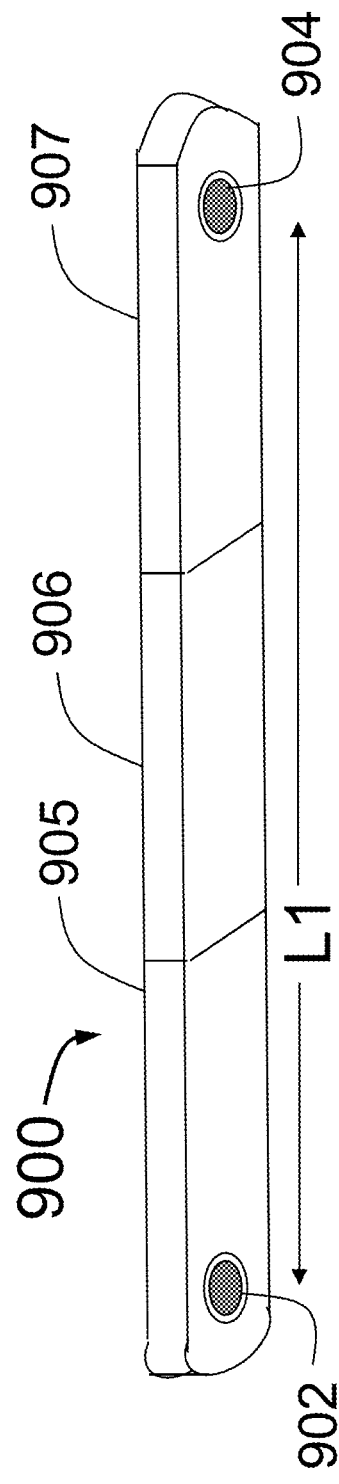
FIG. 15A is a schematic view of a Subcutaneous Cardiac Monitor (SCM) which may be implemented in a form factor similar to the Medtronic Reveal or Abbott Confirm.

FIG. 15A is a schematic view of a Subcutaneous Cardiac Monitor (SCM) 900. It has two electrodes 902 and 904 separated by a distance L1. L1 should be 4 to 50 cm. The electrode 902 is in end section 905 of the SCM 900, the electrode 904 is in end section 907 of the SCM 900. The center section 906 of the SCM 900 is envisioned to contain the components that include electronics, battery, RF transducer and vibrator similar to the IMD 10 of FIG. 4. With a two electrode SCM 900, R-R monitoring and syncope detection similar to current loop recorders can be performed.

The sections 905 and 907 would preferably be flexible to better to contour to the subcutaneous space where it is implanted. While the end sections 905 and 907 are shown as the same cross section as the center section 906, it is envisioned they could be of smaller cross section and act as a lead. The electronics could also be located in any or all of the three sections.

To adequately identify coronary occlusive events using ST shift detection, it is envisioned that two SCM 900 devices positioned appropriately with a spacing of the electrodes 902 and 904 greater than 5 cm and ideally greater than 10 cm with an ST shift algorithm. This would replace the need for a long tunneled lead to get the needed two subcutaneous vectors preferred for ST monitoring of all three major coronary arteries. For example, one lead might be under the skin of the left chest above the breast parallel to the cable 832 of FIG. 14, a second SCM 900 could be under the left ribs. It is envisioned that if either device detected an acute ST change, an internal or internal and external alarm with or without cellular messaging could occur.

Figure 15B:
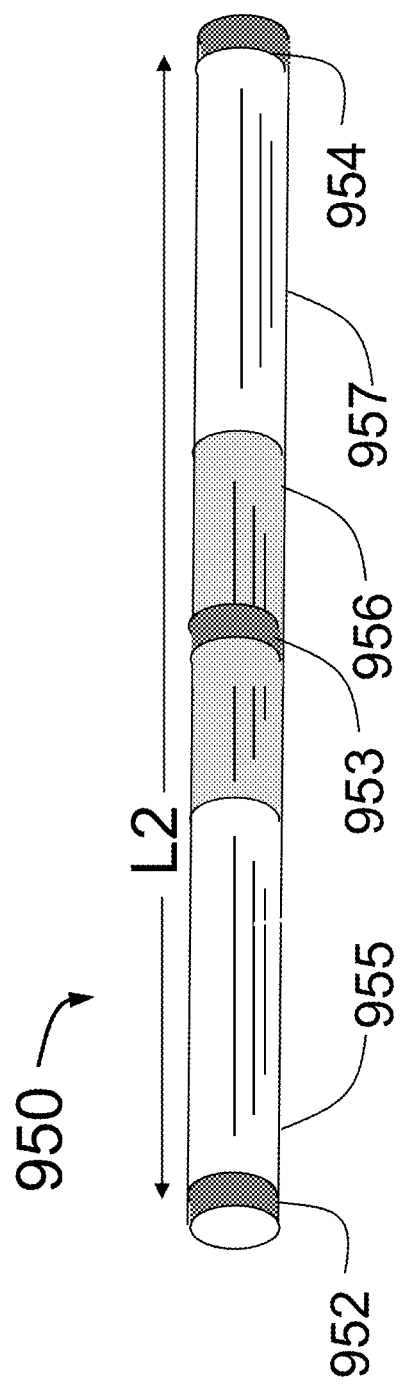
FIG. 15B is a schematic view of an additional embodiment of a subcutaneous Cardiac Monitor (SCM).

FIG. 15B is a schematic view of an additional embodiment of a subcutaneous Cardiac Monitor (SCM) 950. The SCM 950 is envisioned to have a length L2 between 10 and 100 cm and would have at least 2 electrodes 952 and 954 but would preferably have a third electrode 953. It has two end sections 955 and 957 and a center section 956. The center section 956 of the SCM 950 is envisioned to contain the components that include electronics, battery, RF transducer and vibrator similar to the IMD 10 of FIG. 4, however the components could also be located in any or all of the three sections.

The embodiment of the SCM 950 with three electrodes 952, 953 and 954 and a length of 50 to 100 cm would be practical for implementation of the ST shift detection algorithms. Specifically, a preferred use would have the SCM 950 tunneled under the skin in a similar electrode configuration to that of the SSMD 800 of FIG. 14 with one end electrode such as 952 located under the left clavicle the center electrode 953 located near the sternum and the other end electrode such as 954 located near the bottom of the rib cage on the patient's left side. This configuration produces two orthogonal vectors that are needed to accurately identify ST changes induced by occlusion of all three major coronary arteries. It is also envisioned that two SCM 950 configured with two electrodes each could together accomplish the same ability of two orthogonal vectors for occlusion detection based on ST shifts.

Current loop recorder such as the Medtronic REVEAL or Abbott CONFIRM are a type of SCM but have only about 4-10 cm spacing, do not have an appropriate patient referenced machine learned algorithm and high pass filter so that ST monitoring is not a viable capability. It is envisioned that the SCMs 900 and 950 could be configured to provide not only ST monitoring and patient alerting like the AngelMed Guardian®, but could do so in a format that does not require intracardiac sensing.

Figure 16A:
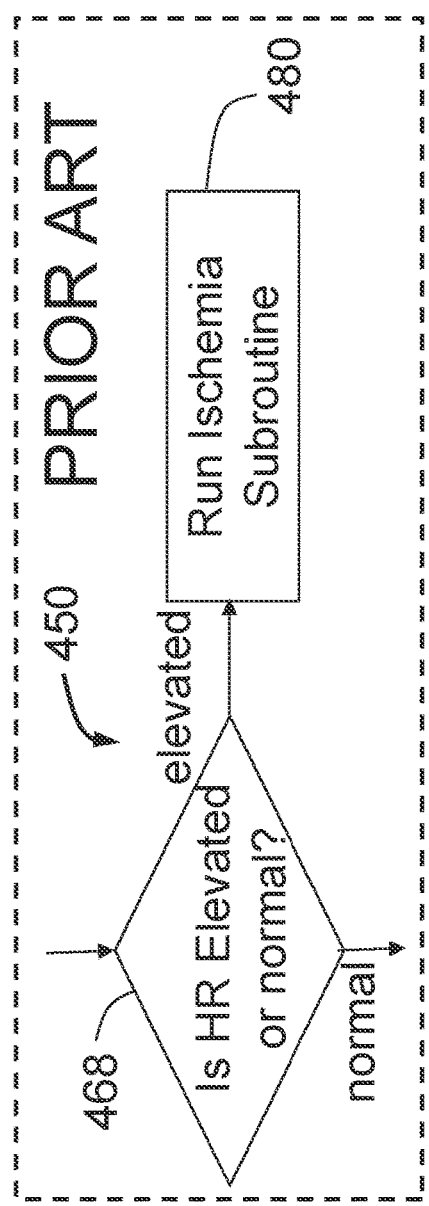
FIG. 16A shows a flow chart of a prior art system.

FIG. 16A shows the ST shift verification subroutine 450 of a prior art system. In the subroutine 450 in step 468 the average R-R interval for an electrogram segment being processed is checked to see if the average heart rate for the segment is in the elevated range. As the R-R interval for a beat in the segment being the time elapsed from the prior beat R wave to the current beat's R wave, the average R-R interval can be calculated by taking the average of the collective multiple R-R intervals for the beats in the segment. Note, the first beat does not have an R-R interval used in the average as there is no prior beat. The average heart rate for the segment is calculated from the average R-R interval of the segment as 60 seconds/average R-R interval in beats per minute (BPM).

If the segment in step 468 is elevated, subroutine 450 runs the ischemia subroutine 480 to determine if there is demand ischemia characterized by excessive ST shifts at elevated heart rate. In an embodiment, the routine 480 may also assess accelerometer data to assess if the patient is likely to be exercising. This capability is similar to running a stress test where the patient exercises to elevate their heart rate and ST changes are looked for to indicate demand ischemia. This prior art embodiment, however, does not evaluate the duration of elevated heart rate which if extended or prolonged can be an indication of improper compliance or dosing related to beat blocker medications.

Figure 16B:
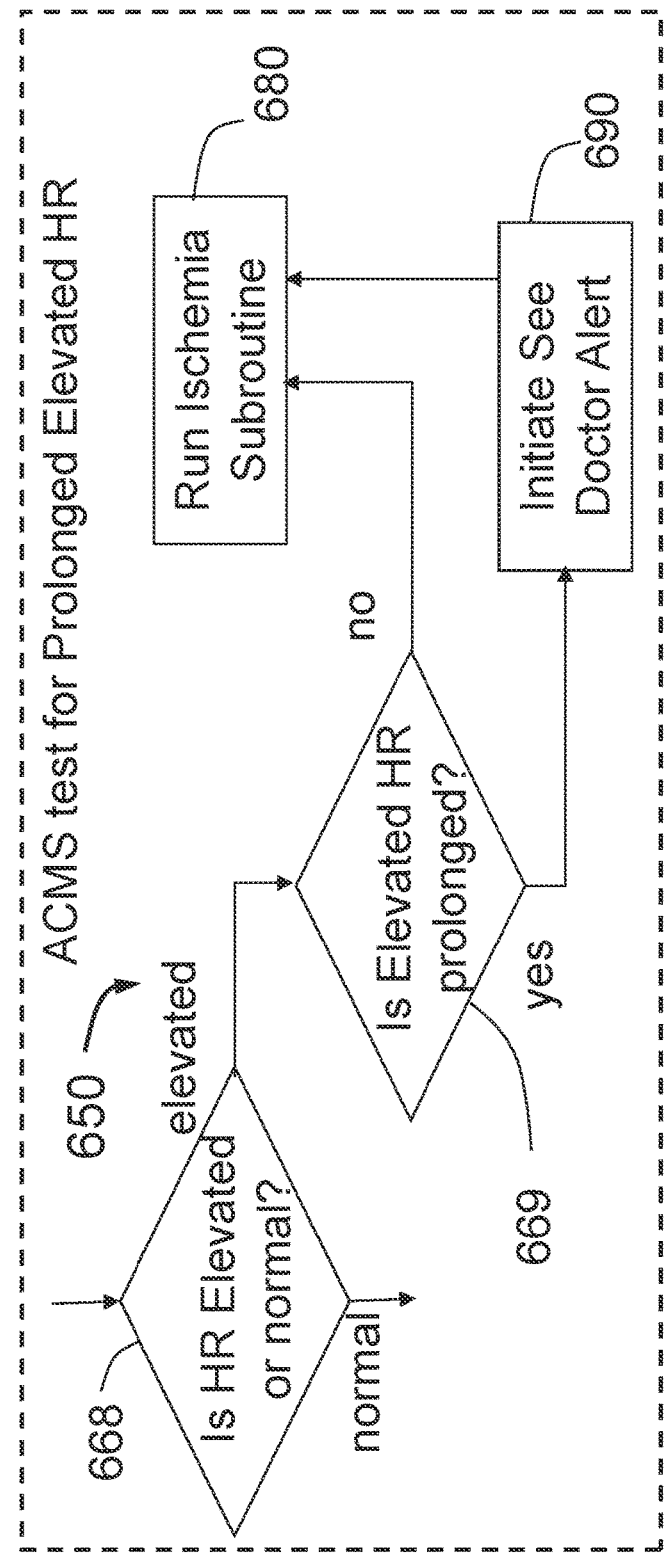
FIG. 16B is a flow chart implemented in the 1 MB, SCM or SSMD of FIG. 3 to detect extended periods of elevated heart rate indicative of improper beta blocker compliance of dosing.

FIG. 16B is a flow chart of the subroutine 450' which is a novel modification to the subroutine 450 of U.S. Pat. No. 6,609,023 implemented in the present invention IMD 10 of FIGS. 3 and 4 to detect prolonged periods of elevated heart rate that may be indicative of improper beta blocker compliance of or dosing. In 650, detection by step 668 of an electrogram segment with an average elevated heart advances the subroutine 650 to step 669 where the duration of elevated heart rate is compared to a pre-set threshold. If the duration exceeds the threshold, and the elevated heart rate is determined to be prolonged or extended, the subroutine 650 initiates a See Doctor Alert in step 690 and then moves on to run the Ischemia subroutine 680 as in the prior art subroutine 450 to see if the patient is experiencing demand ischemia. In other words, step 680 is otherwise the same as step 480 of FIG. 16A. Step 668 also performs the same function as step 468 of FIG. 16A.

Figure 16C:
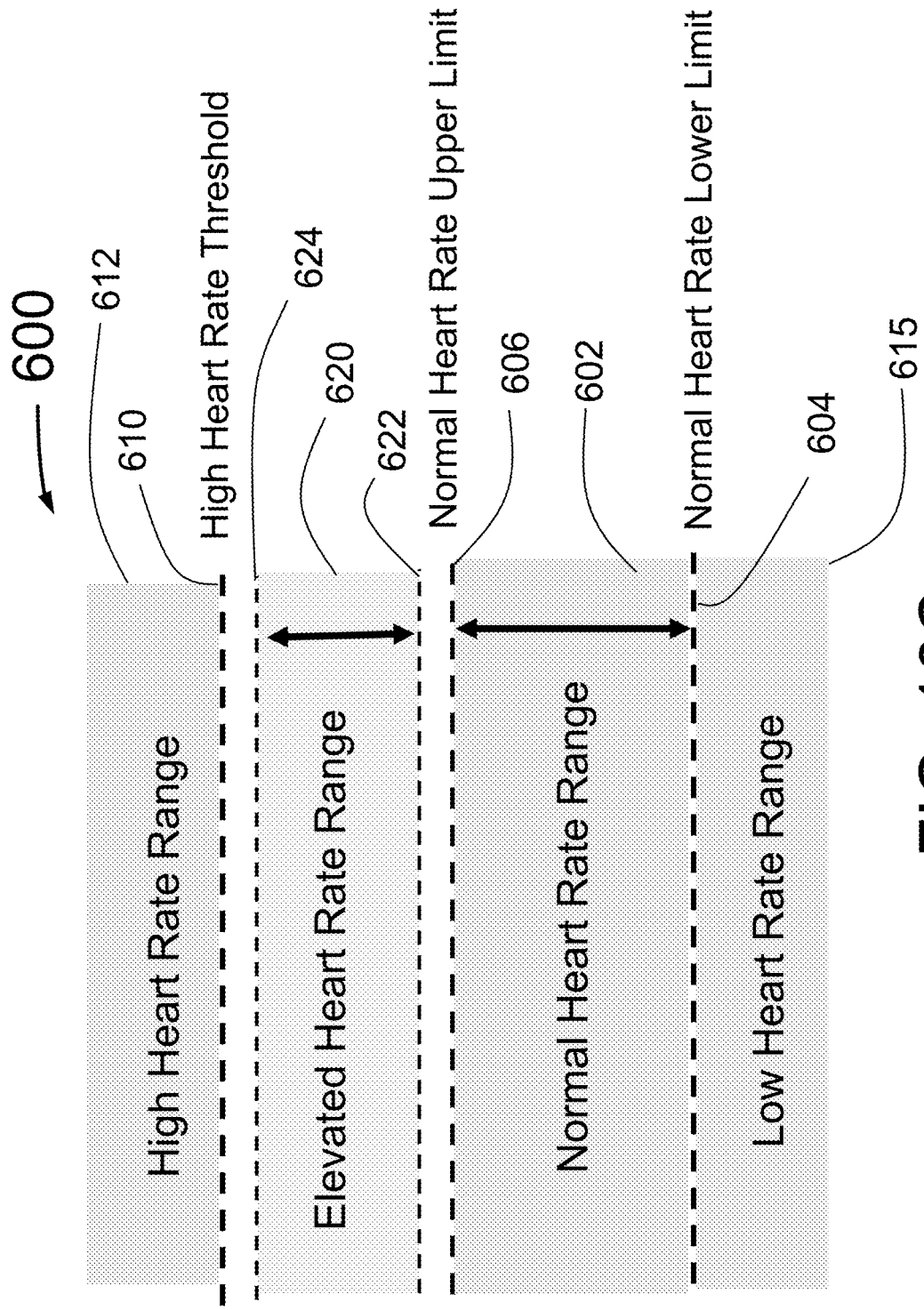
FIG. 16C is a sketch showing the ACMS heart rate limits, thresholds and ranges.

The capabilities described in the prior art for the detection and patient alerting for heart rate anomalies are incorporated herein. This includes the use of at least four ranges of heart rates. As seen in FIG. 16C for the heart rate range schematic, these are: a) a low heart rate range 615 is shown for any heart rate below a lower limit 604 of the normal heart rate range b) a normal range 602 with lower limit 604 and upper limit 606; c) an elevated range 620 with lower limit 622 and upper limit 624 where the lower limit 622 of the elevated range 620 is greater or equal to the upper limit 606 of the normal range 602 and the upper limit 624 is less than or equal to the high heart rate threshold 610 and; d) a high heart rate range 612 is shown for any heart rate above the high heart rate threshold 610.

In some embodiments, the elevated range 620 may be broken into sub-ranges that can be set manually or in one embodiment the ACMS 100 would automatically set these sub-ranges based on the normal heart rate upper limit 606 and the high heart rate threshold 610.

The present invention ACMS 100 of FIG. 3 includes the ability to detect and alert the patient to detection over a pre-set period of time, for each of the following: a) high heart rate above the high heart rate threshold 610, b) low heart rate below the lower limit 604 of the normal range 602, and c) irregular heart rate. Additionally, the present invention provides detection and alerting for extended or prolonged periods of elevated heart rate that is set above the normal range 602 and below a high heart rate threshold 610. The pre-programmed duration for detecting an extended period of elevated heart rate beyond which an alert is provided that may be for example, 10 minutes or more, with a preferred embodiment of more than 1 hour.

The ACMS 100 includes alerting mechanisms that can provide two or more types of alerts associated with at least two levels of severity. The levels of severity would correspond to different levels of danger to the patient associated with the alert. The levels of specific levels of severity for each detected event with an alert would be pre-programmed into the ACMS 100. In programming the ACMS 100 using the physician's programmer 140 of FIG. 3, each type of detected event can be pre-programmed to no alert or one of the two or more levels of severity. For example, a detected ST shift indicative of a potential heart attack would be set to the highest level of severity while detection of an extended period of elevated heart rate would be set to a lower level of severity.

Figure 17:
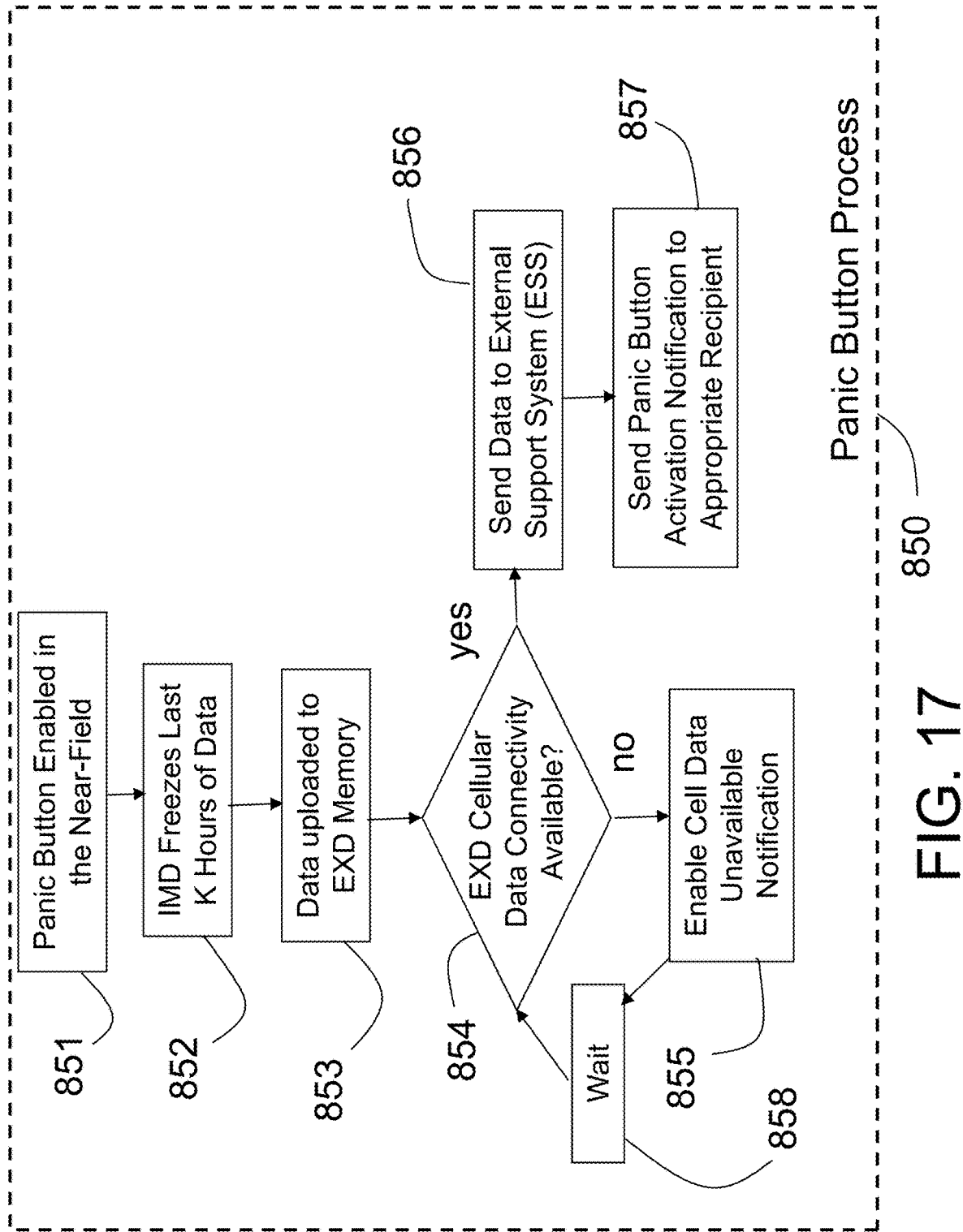
FIG. 17 is a flow chart of the process used by the ACMS to enable patient request for assistance via a "panic button."

FIG. 17 shows the event tagging/panic button process 850 for the ACMS 100 responding to the patient activation in step 851 of the event tagging/panic button feature. It begins with the event tagging/panic button 121 of the EXD 120 of FIG. 3 being activated by the patient in the near field of the IMD 10 (or SCM 900). This activates the IMD 10 or SCM 900 to freeze in memory data collected over the last 24 hours in step 852 (or to transfer these data to an area of IMD 10 memory which is reserved for storing event/panic/stress test data, so the memory/storage operations of the IMD 10 remain unchanged). In step 853 these data along with additional data stored in the IMD 10 or SCM 900 such as ST shift or RR histograms are uploaded to the EXD 120 memory. Next in step 854, the EXD 120 checks for cellular data connectivity either directly through the cellular voice/data sub-system 128 with cellular voice/data sub-system antenna 129 of FIG. 3 or through a paired smart device 225 through the Bluetooth/Wi-Fi transceiver 147 with antenna 148 of FIG. 3. If connectivity is available, the EXD 120 in step 856 transmits the data it uploaded in step 853 to the external support system 240 of FIG. 3 which is typically a HIPPA compliant server. The EXD 120 would then in step 857 send notification of a panic button being activated to the appropriate recipient. Such a recipient could be a medical practitioner having a Smartphone, Tablet or PC running the SDAPP 220 of FIG. 3 and/or a text message or other notification to the patient's care giver, cardiologist or other appropriate recipient. Data relating to the event can be sent to the smart device 225 of FIG. 3 running the SDAPP 220 or the message sent to the smart device 225 could allow the SDAPP 220 to retrieve the additional data from the ESS 240.

If connectivity is not available, step 855 has the EXD 120 and/or IMD 10 (or SCM 900) notify the patient that cellular data is unavailable using vibration, a visual display or acoustic message. It is also envisioned that after notification of cellular connectivity being unavailable in step 855, that the process could wait a pre-set time in step 858 and then try again. If this occurs, the event tagging/panic button process 850 would only allow a certain number of tries before giving up, or halting for a second pre-set time of several hours or days, and providing the patient with notification of the failure.

It is also envisioned that instead of a first step of uploading data to the EXD 120 followed by the EXD 120 transmitting the data after cellular connectivity is established, the process could first establish cellular connectivity then the data could be transmitted through the EXD 120 to the ESS 240 without first storing the data.

A similar process to event tagging/panic button process 850 can result from the event tagging/panic button 826 incorporated into the SSMD 800 of FIGS. 3 and 14.

FIGS. 18, 19 and 20A through 20D describe embodiments of the present invention that provide improved accuracy for the determination of thresholds for detecting excessive ST shifts indicative of a potential heart attack. They include descriptions of the use of histogram-based storage of ST data to compute excessive ST shift detection thresholds. This technique can be used independent of whether the threshold computations occur in the ACMS physician's programmer 140 or the IMD 10, SSMD 800 SCM 900 or EXD 120 of FIG. 3.

An important part of having an accurate ST shift detection system relates to having a patient-specific threshold for detecting excessive ST shift. Prior art systems provide an overview of the use of histogram format stored ST levels to identify the distribution of patient ST levels over days or weeks and that those distributions can be utilized to calculate detection thresholds to be used in detecting excessive ST shift in real time. While the device can use ST segment measured voltages in the detection of ischemia, a preferred embodiment measures "ST deviation" which is the relative amplitude of each heartbeat's ST segment compared to a reference such as an Iso-Electric value which is the typically flat portion of the heart signal wave form that exists for each heartbeat between the P wave and the Q wave, (the PQ segment). An example of the P, Q, R, S and T wave portions of a heartbeat of the sensed heart signal are shown in FIG. 2 of Fischell et al U.S. Pat. No. 6,609,023. ST deviation may be measured, computed and/or stored as any one or more of the following:
1. actual measured voltage
2. arbitrary "ADC" units (e.g., units based on integral numbers produced by the Analog-to-Digital Converter (ADC units))
3. a percentage (or fraction) of a measured amplitude of a portion of the amplitude of the beat (e.g., the QRS section of a beat).

It is important to measure both ST deviation and compute and store the average heart signal amplitude (e.g., QRS amplitude or R-wave amplitude/height) over the same time periods for normalization as the amplitude of heart beats measured in the heart signal from an implanted lead will likely change slowly over time.

ADC units may be:
exactly as produced by the Analog-to-Digital Converter (ADC) (e.g. for an 8 bits the values would be values of 0 to 255 representing integer values of −127 to +128) or
scaled from the ADC output (for example −63 to plus 64).

In a preferred embodiment, ST deviation and average heart signal amplitude are measured and stored in ADC units. Normalization to the average heart signal amplitude as described below, may occur in two calculations:

1. in the computation of excessive ST shift detection thresholds as a percentage or fraction of the average heart signal amplitude, and
2. in the computation of ST shift for a newly collected beat of the sensed heart signal where ST shift is the change in ST deviation between said beat and a baseline value of ST deviation computed as a percentage of a baseline average heart signal amplitude where the baseline data was collected in a prior time period, or across a number of prior periods (e.g., the baseline may be the composite of 24 hourly baseline heart signal samples collected at the start of each hour).

In one aspect of the subject system, there is provided a method for actuating an alarm responsive to detection of excessive ST shift from a heart signal of the patient. Initially, the ST deviation is measured for each beat of a multiplicity of beats from a PQRST representation of the heart signal during a data collection time period. The ST deviation is substantially an ST segment average voltage minus a PQ segment average voltage within each of the beats. Subsequently, there is the creation and storing at least one histogram defined by a set of bins, with each of the bins being associated with an ST deviation range. Each bin maintains a running count of the number of beats whose ST deviation is measured to be within the ST deviation range associated with a respective bin during one data collection time period. The at least one histogram provides an efficient means to store the distribution of ST deviation values over a data collection time period.

A positive excessive ST shift detection threshold is calculated by processing the data from the bins associated with ST deviations greater or equal to zero. A negative excessive ST shift detection threshold is calculated by processing the data from the bins associated with ST deviations less than or equal to zero. The patient is then alerted when one of the multiplicity of beats has an ST shift that exceeds one of the positive or negative excessive ST shift detection thresholds.

The present invention envisions that this process can work in several ways including the use of an external ACMS physician's programmer 140 of FIG. 3 where the ST deviation and heart signal amplitude data are uploaded from the IMD 10, SSMD 800 or SCM 900 of FIG. 3 to the programmer 140. The programmer 140 then calculates excessive ST shift detection thresholds which are used to detect potential ACS events and are subsequently downloaded back to the IMD 10, SSMD 800 or SCM 900. It is also envisioned that the IMD 10, SSMD 800 or SCM 900 could compute excessive ST shift detection thresholds after collecting a sufficient amount of ST level data, automatically or following interaction with local or remote external systems.

Figure 18:
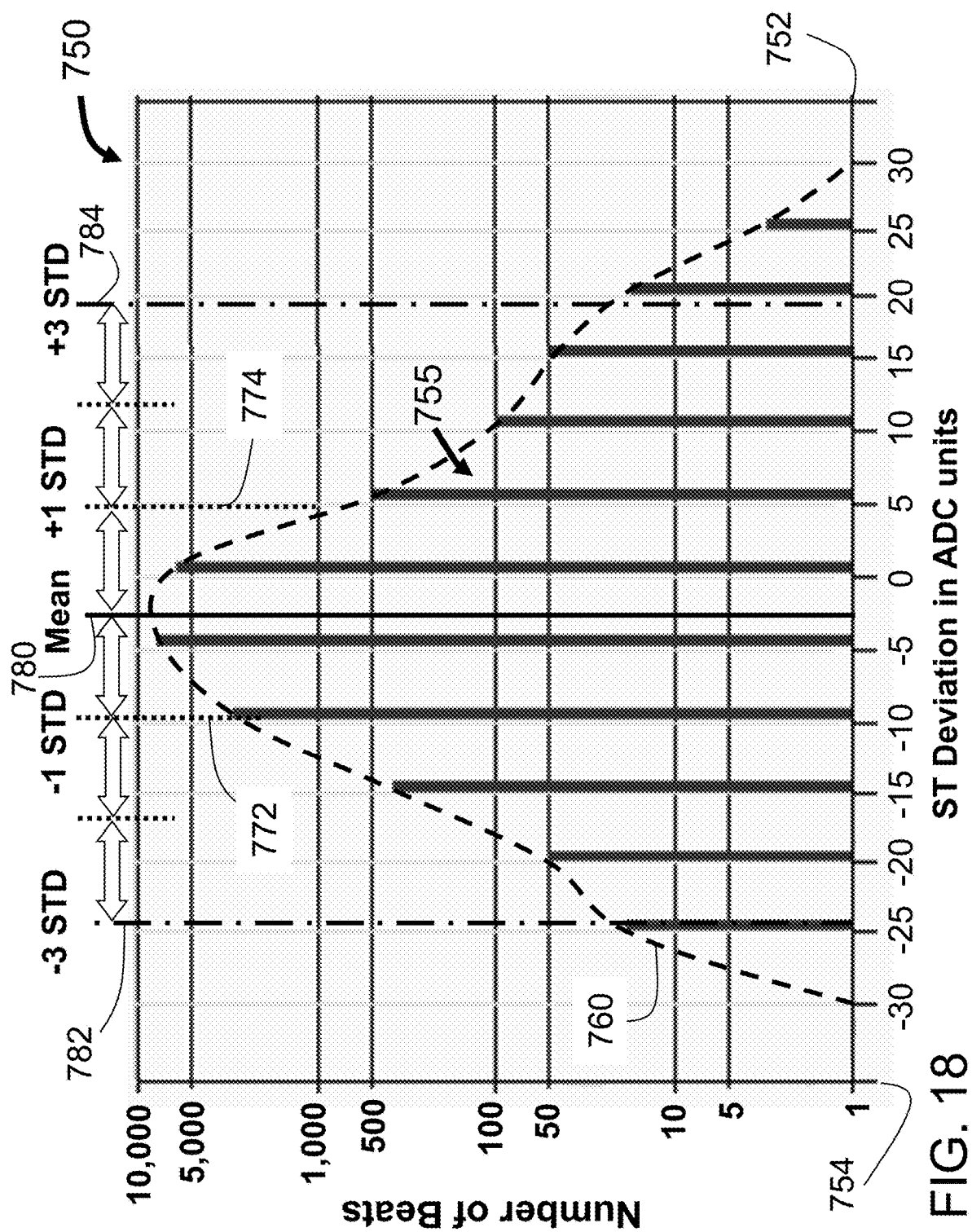
FIG. 18 is a graphical depiction of the data from an ST shift histogram utilized to calculate positive and negative excessive ST shift detection thresholds.

FIG. 18 shows an example of a relatively symmetric ST deviation histogram 750 collected over a sufficient number of days required to obtain a large set (e.g., tens of thousands of analyzed heart beats). The ST deviation histogram 750 is shown as a logarithmic plot as seen in the vertical axis 754. The horizontal axis 752 shows 13 bins corresponding to 13 values of ST deviation in the arbitrary ADC units that are produced by the ADC Converter. Each bin is 5 ADC units wide. For example, the −30 bin is incremented if the ST deviation in ADC units for a beat is −32, −31, −30, −29 or −28) Similarly, the 0 bin is incremented if the ST deviation in ADC units for a beat is −2, −1, 0, 1 or 2. FIG. 18 is an example that shows bins labeled −30 to +30, while the actual values will depend on the data and the range of ADC buffer. The bins in this example are 5 units wide, however the width can be a larger or smaller number of ADC units.

In another embodiment, the bins would represent the ST deviation as a percentage heart signal amplitude where the bins would be 5% wide.

In an embodiment, along with the histogram 750, the IMD 10, SSMD 800 or SCM 900 of FIG. 3 would measure and save an average value of heart signal amplitude (e.g., QRS amplitude or R-Wave amplitude/height) from a multiplicity of beats of the heart signal collected over the same data collection time period during which bins in the histogram 750 are incremented. It is most efficient if heart signal amplitude and ST deviation values are measured and stored in ADC units.

In one embodiment, the histogram 750 which provides the running count of ST deviation values in ADC units and a saved value of average heart signal amplitude in ADC units from a multiplicity of beats collected during a data collection time period are used to calculate positive and negative excessive ST shift detection thresholds as follows:

1. The mean (line 780) and negative and positive standard deviations (lines 772 and 774) are calculated from the data in the histogram 750,
2. the positive ST deviation threshold in ADC units (line 784) is set as the mean plus a multiple of (for example 3) standard deviations,
3. the negative ST deviation threshold in ADC units (line 784) is set as the mean minus a multiple of (for example 3) standard deviations,
4. The positive excessive ST shift detection threshold is then computed as the positive ST deviation threshold computed as a percentage or fraction of the average heart signal amplitude,
5. The negative excessive ST shift detection threshold is then computed as the negative ST deviation threshold computed as a percentage or fraction of the average heart signal amplitude, The histogram envelope 760 is also shown and may be part of the histogram display incorporated into the ACMS physician's programmer 140 or the SDAPP 220 of FIG. 3. Of great importance is the depiction of the mean ST deviation 780 and the positive and negative standard deviations 774 and 772 respectively of the histogram data 755.

While FIG. 18 shows the use of the mean ST deviation value as the basis for determining positive and negative detection thresholds, in embodiments the zero value or median ST deviation value is used.

Figure 19:
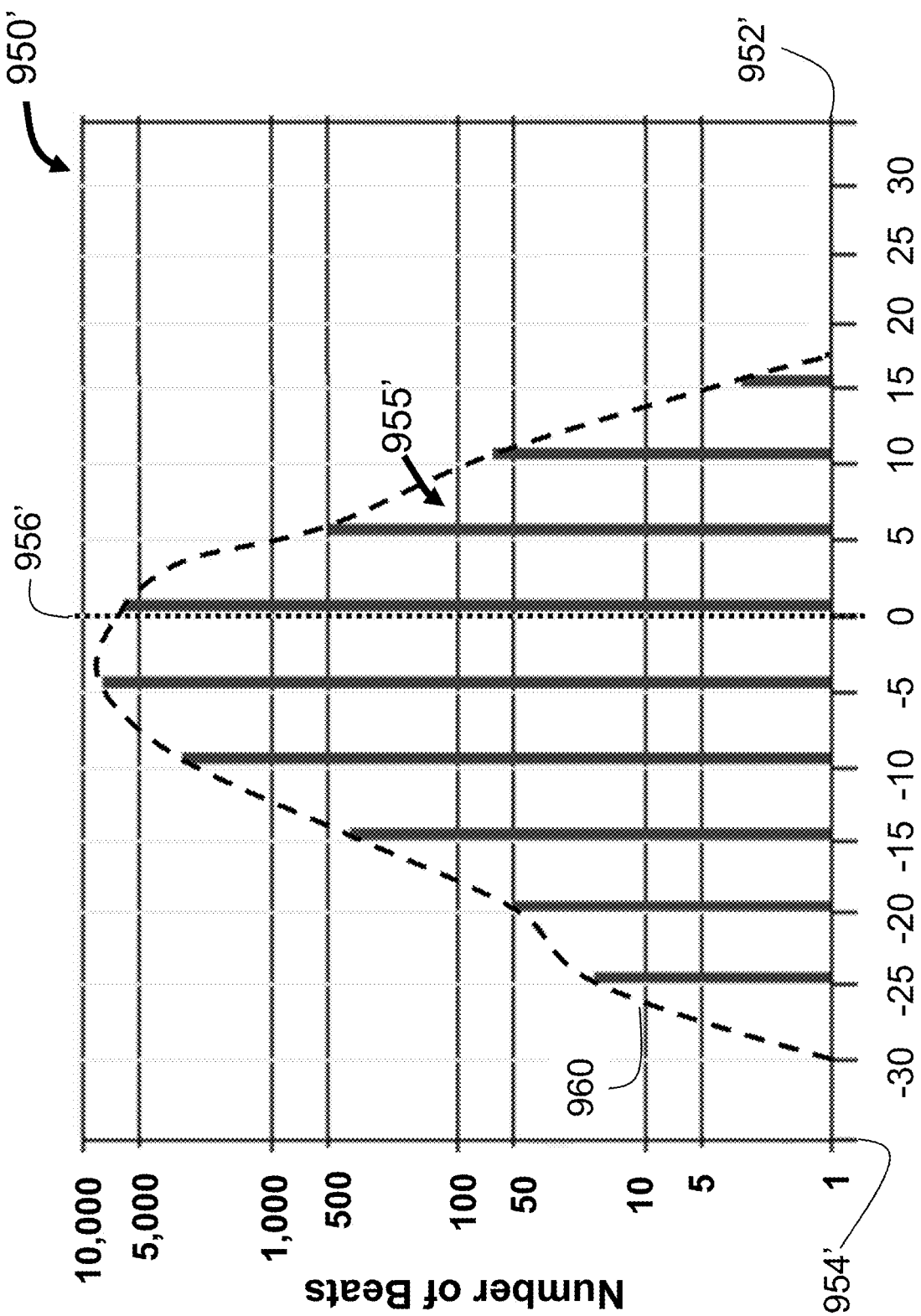
FIG. 19 shows an example of an asymmetric ST shift histogram collected over a sufficient number of days to obtain thousands of analyzed heart beats.

FIG. 19 shows an example of an asymmetric ST deviation histogram 950' collected over a sufficient number of days to obtain a large dataset of heartbeats (e.g., thousands of analyzed heart beats). The histogram is shown as a logarithmic plot as seen in the vertical axis 954'. The horizontal axis 952' shows 13 bins corresponding to 13 values of ST deviation in the arbitrary units that are produced by the Analog-to-Digital Converter (ADC units). Each bin is 5 ADC units wide. For example, the −30 bin is incremented if the ST deviation in ADC units for a beat is −32, −31, −30, −29 or −28) Similarly the 0 bin is incremented if the ST deviation in ADC units fora beat is −2, −1, 0, 1 or 2.

The histogram envelope 960 is also shown and may be part of the histogram display incorporated into the ACMS physician's programmer 140 or the SDAPP 220 of FIG. 3.

It should be noted that for many patients the ST deviation histogram 950' is not likely to be symmetrical around the zero ST deviation value shown by the line 956'. In embodiments of the present invention the positive and negative normal ranges of a patient are based upon variability statistics such as standard deviations that are calculated separately to determine ischemia detection thresholds that are reflective of the patient's normal ST levels. Not to be limited by theory, using a can-to-tip vector for measuring ST levels may typically produce a greater amount of data and larger values and amount of negative values of ST deviation as sub-endocardial ischemia from stenoses in the patient's coronary arteries may create ST depression even within the normal heart rate range. Typically, a negative shift in the can-to-tip vector from occlusion of a coronary artery occurs when the artery is feeding directly to the tip electrode location. Such shifts are typically much larger than positive shifts that occur from occlusion of a coronary artery feeding a portion of the heart muscle at some distance away from the tip electrode location.

Figure 20C:
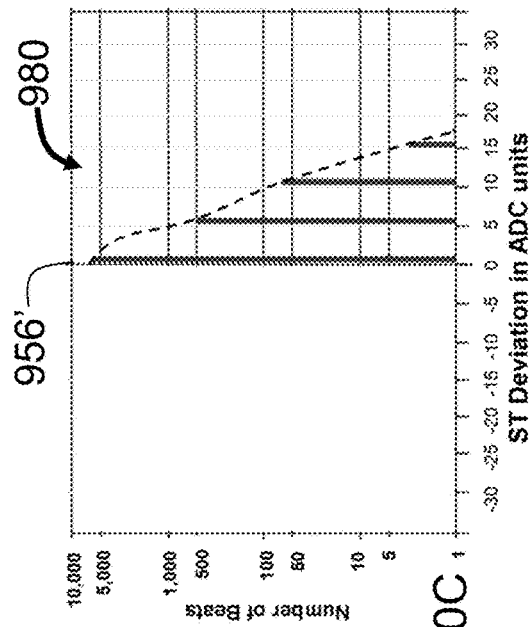
FIG. 20C shows the positive portion of the ST shift distribution of FIG. 19.
Figure 20D:
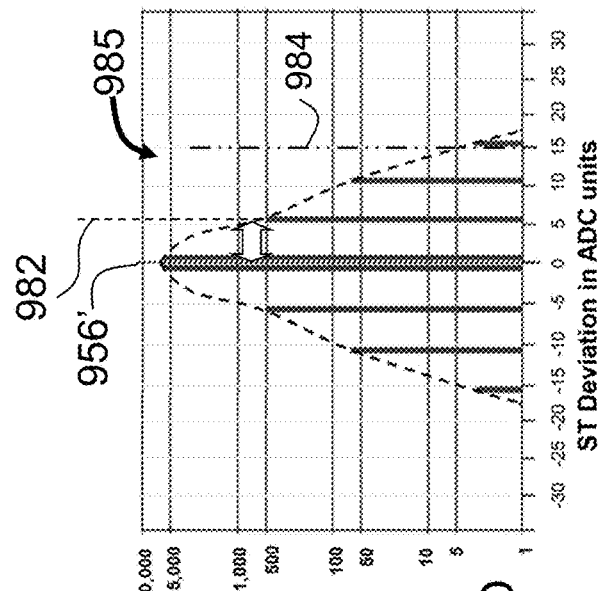
FIG. 20D shows the ST shift distribution with the positive portion of FIG. 20C mirrored about the zero value.
Figure 20A:
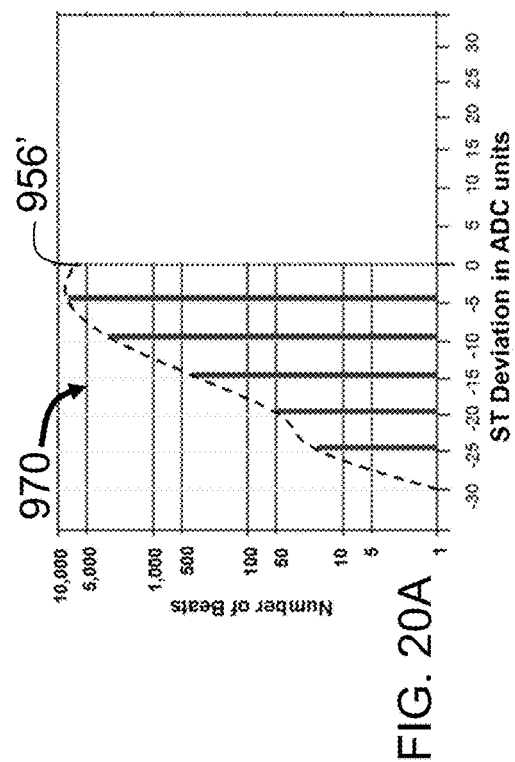
FIG. 20A shows the negative portion of the ST shift distribution of FIG. 19.
Figure 20B:
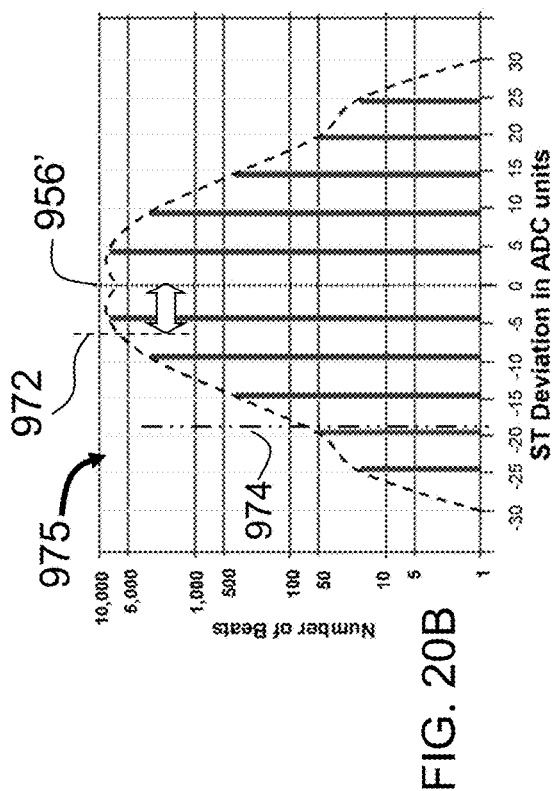
FIG. 20B shows the ST shift distribution with the negative portion of FIG. 20A mirrored about the zero value.

FIGS. 20A thru 20D illustrate embodiments how separate calculations of positive and negative distributions are accomplished. FIG. 20A shows the negative portion 970 of the ST deviation distribution 950' of FIG. 19. To calculate the standard deviation (or another statistically relevant metric of dispersion) for this portion of the distribution 950', the distribution 970 is mirrored about the zero value 956' creating the distribution 975 shown in FIG. 20B. These data are then analyzed to calculate the negative standard deviation shown as the line 972.

FIG. 20C shows the positive portion 980 of the ST deviation distribution 950' of FIG. 19. To calculate the standard deviation (or another statistically relevant metric of dispersion) for this portion of the distribution 950', the distribution 980 is mirrored about the zero value 956' creating the distribution 985 shown in FIG. 20D. These data are then analyzed to calculate the positive standard deviation shown as the line 982.

While standard deviation is mentioned here any statistical measure related to the range of ST levels may be used such as, for example, range, probability density functions, the inter-quartile range (IQR), and variance.

In the next step these separate positive and negative standard deviations 982 and 972 are used to calculate positive ST deviation threshold shown by the line 984 of FIG. 20D and the negative ST deviation threshold shown by the line 784 of FIG. 20C.

In one embodiment, over a data collection timer period, the histogram 950 provides the running count of ST deviation values in ADC units and the IMD 10, SSED 800 or SCM 900 also computes the average heart signal amplitude in ADC units from a multiplicity of beats. These data are used to calculate positive and negative excessive ST shift detection thresholds as follows:

1. the positive ST deviation threshold in ADC units (line 984) is set as the mean plus a multiple of (for example 3) standard deviations (982),
2. the negative ST deviation threshold in ADC units (line 974) is set as the mean minus a multiple of (for example 3) standard deviations (972),
3. The positive excessive ST shift detection threshold is then computed as the positive ST deviation threshold computed as a percentage or fraction of the average heart signal amplitude,
4. The negative excessive ST shift detection threshold is then computed as the negative ST deviation threshold computed as a percentage or fraction of the average heart signal amplitude, In one embodiment, the ST deviation thresholds described in step 2 above are then adjusted to take into account two additional factors:

all the ST deviation histogram data upon which these initial thresholds are based is stored in bins that are, for example, 5 ADC units wide. That means there is some uncertainty in the spread estimate and needs to be considered.

From one data collection time period to the next, variation in the mean (or median) value of the ST deviation histogram shown in FIG. 19 will change. It is also envisioned that this variation bay be used to adjust the ST deviation thresholds.

In one embodiment, once the positive and negative excessive ST shift detection thresholds (saved as a percentage or fraction) are stored in the Program Parameters Memory 475 of FIG. 4, the IMD 10 (or SSMD 800 or SCM 900) would identify an excessive ST shift event as follows:

1. Periodically, heart signal beats would be analyzed to update a baseline including two primary heart signal parameters of average ST deviation in ACS units and average heart signal amplitude (e.g., QRS amplitude or R-wave amplitude/height) in ACS units
2. The IMD 10 will collect new beats for which ST deviation in ACS units will be computed and then the ST shift for that beat will be computed as the ST deviation for that beat as a percentage (or fraction) of the baseline heart signal amplitude.
3. If the ST shift is positive and greater than the positive excessive ST shift detection threshold stored in the Program Parameters Memory 475 or the ST shift is negative and more negative than the negative excessive ST shift detection threshold, then the beat is identified as Shifted.
4. If a multiplicity of shifted beats is identified over a pre-set time period, the IMD 10 will initiate a patient alert.

In one embodiment, a 10 second segment of heart signal data is collected every 30-90 seconds and if 6 out of 8 beats are shifted in three successive 10 second segments, the patient alert is initiated.

In one embodiment the data collection time period for each histogram is 24 hours, an average heat signal amplitude is also saved for each 24-hour period and histograms and average heart signal amplitudes are maintained in memory for up to 14 days.

In another embodiment, an adjustment factor may be used for adjusting the setting for the negative excessive shift thresholds. For example, the positive threshold could be set at 3 standard deviations and the negative threshold at 4 standard deviations below the mean, median or zero point.

Rather than using histogram data, it is possible to store the set of raw values for ST-deviation or any other cardiac feature disclosed herein, and furthermore these can be identified in relation to the corresponding heart rate. The related summary statistics can also be computed from either summary constructs such as histograms, clusters, or other data reduction schemes, or can be computed from individual measures which require larger memory storage. Rather than mean/median, other measures of central tendency may be used including weighted averages and other statistics that exclude or minimize the contribution of atypical data, and measures of variance may similarly be extended from standard deviation to any other measure that relates to spread, bias, skewness, or other metric related to the distribution or variance of the data for an individual.

Lastly, various interpolation schemes may be used to provide metrics for various heart rate ranges if the recorded data for an individual are sparse within selected ranges. For example, if data for the normal range is sufficient for establishing ischemia detection thresholds, but the data in the elevated heart rate bin(s) is/are sparse because the patient's heart did not enter those ranges during a baseline period, then the thresholds for those elevated heart rate bins at range are determined from the positive and negative standard deviations 982 and 972 of FIGS. 20B and 20D respectively (or other variance measures) for the normal heart rate bin. In embodiments several factors are taken into consideration, such as:

- the number of beats in each elevated heart bin for each day: for any day/bin with a count of less than a threshold (such as, for example, 16), consider the count to be 0
- for days/bins where the median cannot be calculated for lack of beats in the histogram, set the median value to be the median value of the next lower heart rate bin
- the granularity of the histogram bin sizes With these considerations, the positive threshold for an elevated heart rate bin can be set as the sum of the positive threshold for the normal heart rate bin plus the difference in the medians of the elevated heart rate bin and the normal heart rate bin plus the size of the histogram bins (such as, for example, preferably 5) converted to a % of baseline RPQ. The negative threshold for an elevated heart rate bin is the negative threshold for the normal heart rate bin plus the difference in the medians of the elevated heart rate bin and the normal heart rate bin minus the size of the histogram bins (such as, for example, preferably 5) converted to a % of baseline RPQ. In an embodiment, the ischemia detection threshold for a heart rate range which meets a sparseness criterion is set by calculating the variance measure that is obtained from the normal heart rate range which is offset by the difference between the median (or other measure of central tendency) of the normal heart rate range and the median of the bin for the elevated heart rate range. Alternatively, the variance of the measure for the normal heart rate range can be multiplied by a constant that is calculated based upon population normative ranges for the elevated or high ranges. Alternatively, the threshold may be set as the difference between the threshold for the normal heart rate range and the range of an elevated or high heart rate range based upon the number of intervening bins. In other words, the threshold can be interpolated using threshold level above and below a missing heart rate bin. Elevated range thresholds could also be determined by an adjustment factor. For example, the thresholds could increase for positive shifts and decrease by negative shift by a preset percentage as one moves to successive elevated heart rate ranges.

The above system that calculates ST deviation (ST compared to Iso-Electric) for hundreds/thousands of beats over hours, days or weeks to provide data for calculating thresholds defining the normal patient heart signal so that only a significant acute event like a total occlusion of a coronary artery will produce sufficient changes that exceed the thresholds. The methods for establishing thresholds and enabling a detection algorithm for identifying abnormal ST changes that can be used to detect an acute myocardial infarction (heart attack) can be realized as follows.

Method 1 uses the physician's programmer 140 of FIG. 3 in conjunction with a Heart Signal Capture and Event Detection (HSCED) device that can be the IMD 10, SSMD 800 or SCM 900 of FIG. 3.

Method 1 includes the steps of:
1. Placing at least 2 electrodes in contact with a portion of the patient in a position to sense electrical signals from heart. Such positions include electrodes that are:
   - in contact with the heart including those that are part of a pacemaker or ICD lead,
   - on or including the surface of an implantable device,
   - electrodes on the patient's skin and implanted subcutaneously.
2. Connecting the electrodes with conducting means to the HSCED) device.
3. Enabling the HSCED to collect heart signal data for a multiplicity of beats including the measurement of the ST level, ST deviation or ST shift of each beat. This may run for a pre-set number of beats or a pre-set or variable period. For example, the HSCED could operate in a collection mode until it had a total of a thousand beats then stop collecting. It could also collect data for 24 hours, save the data and start a new 24-hour period of collection. In this second case, the data could be retained in memory for a second longer data retention period. For example, the 24-hour collections could be saved for 14 days before they are overwritten. Data can be saved as individual numbers or in a histogram or other appropriate format.
4. After a selected number of beats or time has elapsed, the HSCED would upload the data to the physician's programmer 140 of FIG. 3. This would ideally be done during incision check 7-14 days after an implantable HSCED is inserted or at any time after enough data is collected for a non-implantable HSCED has been in use.
5. The physician's programmer 140 would include statistical processing algorithms to calculate positive and/or negative excessive ST shift detection thresholds from the uploaded data. It is envisioned that this would be done at least for at those data where the R-R interval of the beats correspond to a normal heart rate range for the patient. Ideally, it would be done for one or more elevated heart rate ranges as well.
6. The calculated positive and negative thresholds would then be downloaded back to the HSCED.
7. The HSCED would then be activated to detect excessive ST shift using the downloaded thresholds as described herein.

Method 2—provides the calculation of detection thresholds within a HSCED that can be the IMD 10, SSMD 800 or SCM 900 of FIG. 3.

Method 2 substitutes the steps 4 and higher as follows:
4. After a sufficient number of beats or time have elapsed, the HSCED would process the data collected to calculate positive and/or negative excessive ST shift detection thresholds from the uploaded data. It is envisioned that this would be done at least for at those data where the R-R interval of the beats correspond to a normal heart rate range for the patient. Ideally, it would be done for one or more elevated heart rate ranges as well.
5. The calculated positive and negative thresholds would then be saved in memory of the HSCED for use in detection of excessive ST shifts.
6. The HSCED would then be activated to detect excessive ST shift using the downloaded thresholds as described herein.

The techniques described with FIG. 18, 19 or 20A-D are applicable to either Method 1 or Method 2. Method 2 may also include a verification step between steps 5 and 6 where wireless connectivity of the HSCED would be used to allow the information related to the calculation of the thresholds to be verified externally by humans or other computer systems.

All of the techniques described with respect to the descriptions of FIGS. 18 through 20D require a calculation of the standard deviation of the distribution stored in histogram format. An example of the formula used to calculate one standard deviation (sigma) including using samples from a histogram is:

$$\sqrt{\frac{n \times \sum x^2 - (\sum x)^2}{n \times (n-1)}}$$

where n is the total number of samples in each histogram bin and the x's are the values of the samples in the respective histogram bin.

Figure 21A:
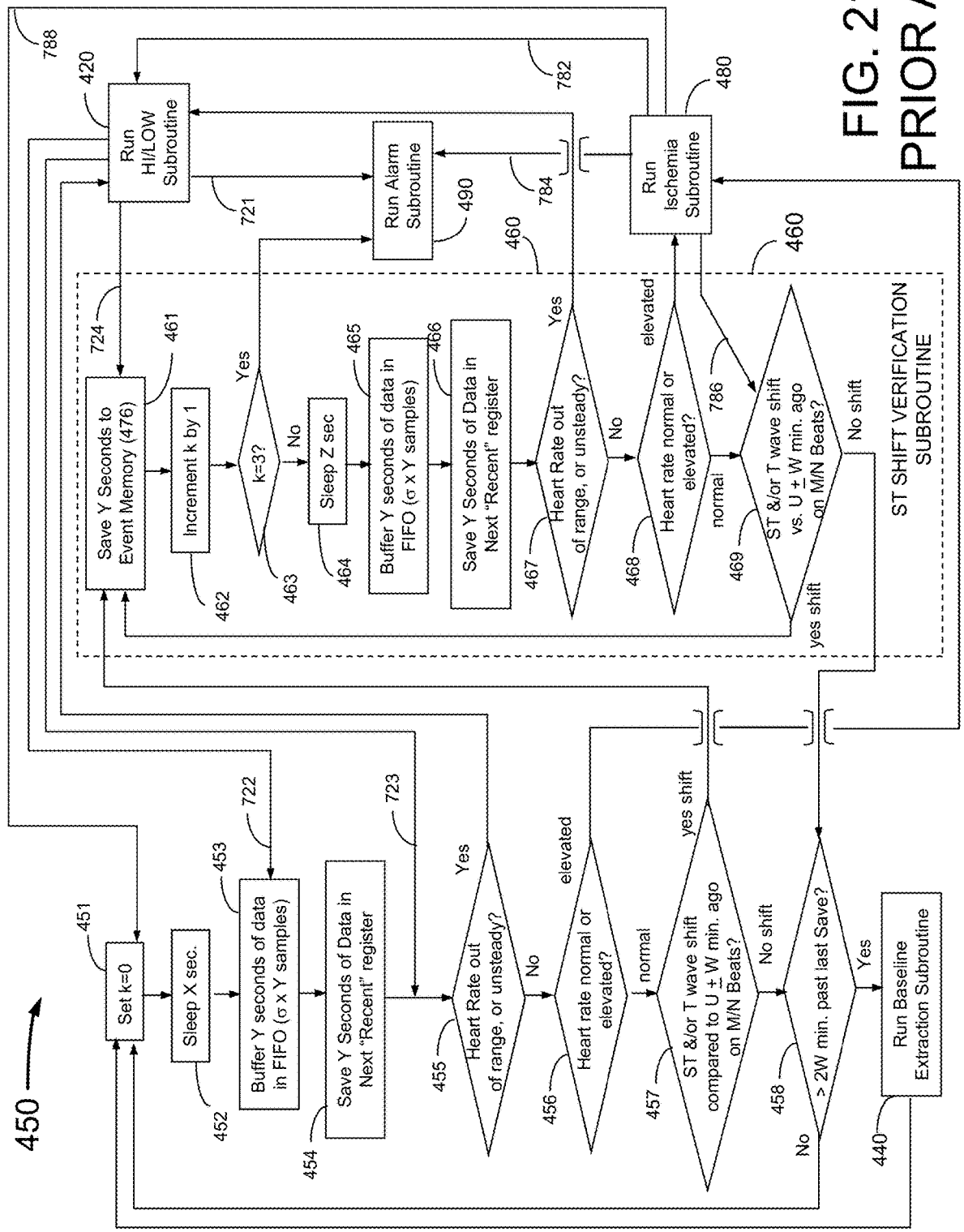
FIG. 21A shows a block diagram for the process for identifying excessive ST shift events of a prior art system.
Figure 21B:
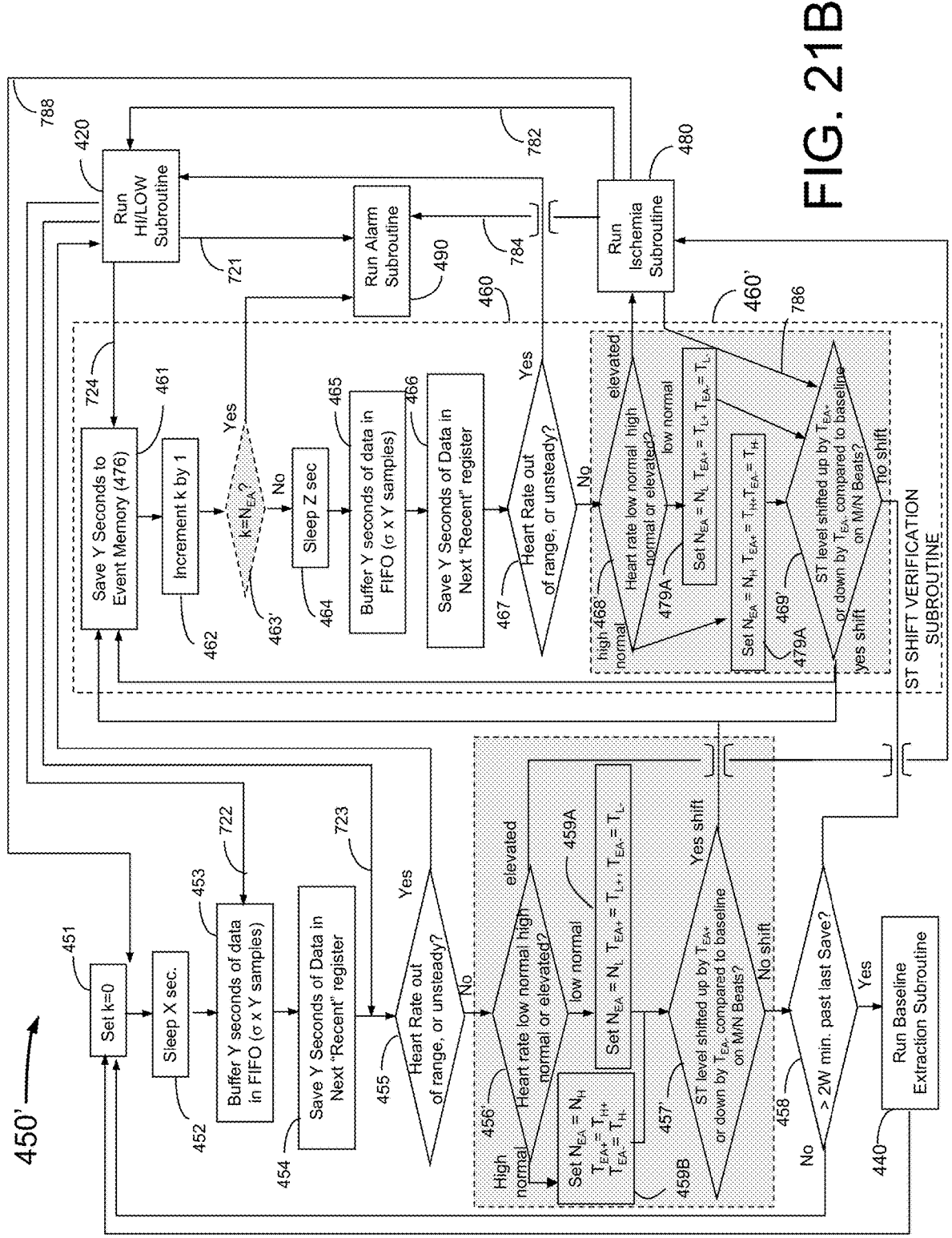
FIG. 21B shows a block diagram of the process used to enhance accuracy of ST shift based emergency alarms.

FIGS. 21A and 21B are used to illustrate an embodiment of the present invention that helps differentiate between ST changes from demand ischemia in the upper portion of a normal heart rate range and ST changes from a potential heart attack.

The present invention envisions enhancements to the process 450 prior art shown in FIG. 21A which is taken from FIG. 5 of U.S. Pat. No. 6,609,023 that is incorporated herein by reference. FIG. 21 A shows a process 450 for identifying excessive ST shift events by detecting 3 successive events that meet the criteria for detection of step 469. Upon 3 such events, step 463 initiates the running of the alarm subroutine 490.

FIG. 21B shows a block diagram of the process 450' used to enhance accuracy of ST shift based emergency alarms.

Improvements from the prior art shown in FIG. 21A are shown in the shaded boxes and include steps 456', 459A, 459B, 457', 463' and 469'.

Step 456' replaces step 456 of FIG. 21A that differentiates the average heart rate of the Y seconds into two categories (normal or elevated) by identifying whether the heart rate/RR interval associated with the Y seconds of electrogram data is in one of three categories (low-normal, high-normal, or elevated).

If elevated, the step 456' does the same thing as step 456 of FIG. 21A advancing to the ischemia subroutine step 480.

If low-normal, step 456' advances to step 459A and the number of successive segments shifted needed to trigger an emergency alarm $N_{EA}$ is set to the value $N_L$ and the positive threshold for detecting ST shifts for an emergency alarm ("$T_{EA+}$") is set to the positive threshold value ("$T_{L+}$") and the negative threshold ("$T_{EA-}$") is set to the negative threshold value $T_{L-}$.

If high-normal step 456' advances to step 459B where $N_{EA}$ is set to the value $N_H$ and positive threshold for detecting ST shifts for an emergency alarm $T_{EA+}$ is set to the value $T_{H+}$ and the negative threshold $T_{EA-}$ is set to the value $T_{H-}$.

Having a variable counter threshold $N_{EA}$ allows different values that are set in steps 459A or 459B depending on whether the average heart rate for the Y seconds of data is low-normal or high-normal. For example, $N_L$ could be 3 the same number of successive segments used in FIG. 21A. It is envisioned that $N_H$ would be higher than $N_L$ (e.g., 5 or more). In this way the system would be less likely to trigger an emergency alarm for ST changes caused by demand ischemia.

Steps 459A and 459B advance to step 457' where a baseline ST wave level is compared to the ST level seen on N beats in the Y seconds of data saved in step 454. If the M out of N beats are shifted up by more than the positive threshold for initiating an emergency alarm $T_{EA+}$ or down by more than the negative threshold $T_{EA-}$ the process advances to step 461 of the ST shift verification subroutine 460' where the Y seconds are saved to event memory and the successive event counter k is incremented by one in step 462 and then compared to $N_{EA}$ in step 463' which differs from step 463 in FIG. 21A where k is compared to the set value of 3.

Step 463' will advance to the Alarm subroutine 490 if k=$N_{EA}$. If not it will continue as in the prior art routine 460 of FIG. 21A by sleeping Z seconds in step 464, collecting Y seconds of data in steps 465 and 466, screening for abnormal heart rates in step 467 and the once again looking to see if the average heart rate is low-normal, high-normal or elevated in step 468' which is the same as step 456'

Step 468' replaces step 468 of FIG. 21A that differentiates the average heart rate of the Y seconds into two categories (normal or elevated) by identifying whether the average heart rate/RR interval associated with the Y seconds of electrogram data is in one of three categories (low-normal, high-normal or elevated).

If elevated, the step 468' does the same thing as step 468 of FIG. 21A advancing to the ischemia subroutine step 480.

If low-normal, step 468' advances to step 479A and the number of successive segments shifted needed to trigger an emergency alarm $N_{EA}$ is set to the value $N_L$ and the positive threshold for detecting ST shifts for an emergency alarm $T_{EA+}$ is set to the value $T_{L+}$ and the negative threshold $T_{EA-}$ is set to the value $T_{L-}$.

If high-normal step 468' advances to step 479B where $N_{EA}$ is set to the value $N_H$ and positive threshold for detecting ST shifts for an emergency alarm $T_{EA+}$ is set to the value $T_{H+}$ and the negative threshold $T_{EA-}$ is set to the value $T_{H-}$.

Having a variable counter threshold $N_{EA}$ allows different values that are set in steps 479A or 479B depending on whether the average heart rate for the Y seconds of data is low-normal or high-normal. For example, $N_L$ could be 3 the same number of successive segments used in FIG. 21A. It is envisioned that $N_H$ would be higher than $N_L$ (e.g., 5 or more). In this way the system would be less likely to trigger an emergency alarm for ST changes caused by demand ischemia.

Steps 479A and 479B advance to step 469' where a baseline ST wave level is compared to the ST level seen on N beats in the Y seconds of data saved in step 465. If the M out of N beats are shifted up by more than the positive threshold for initiating an emergency alarm $T_{EA+}$ or down by more than the negative threshold $T_{EA-}$ the process advances to step 461 of the ST shift verification subroutine 460' where the Y seconds are saved to event memory and the successive event counter k is incremented by one in step 462 and then compared to $N_{EA}$ in step 463' which differs from step 463 in FIG. 21A where k is compared to the set value of 3.

Step 463' will advance to the Alarm subroutine 490 if k=$N_{EA}$. If not it will continue as in the prior art routine 460 of FIG. 21A by sleeping Z seconds in step 464, collecting Y seconds of data in steps 465 and 466, screening for abnormal heart rates in step 467 and the once again looking to see if the average heart rate is low-normal, high-normal or elevated in step 468' which is the same as step 456'

Having different excessive ST shift detection thresholds depending on whether the heart rate is low-normal or high-normal can help the ACMS 100 of FIG. 3 differentiate between transmural ischemia created by a total coronary occlusion and sub-endocardial demand ischemia due to heart rates in the upper range of normal.

The detailed description of FIGS. 17-19 discusses how both negative and positive excessive ST shift detection thresholds would be set using collected ST data stored in histogram format. Prior art systems describe the use of a multiplicity of histograms associated with a data collection time period each one associated with a different heart rate/RR interval range. While the prior art describes use of a normal range and multiple elevated range, the present invention process shown in FIG. 21B envisions using two normal ranges (low-normal and high-normal). Each would have a histogram so that the thresholds selected based on these histograms would be better suited to avoid false detections compared to a single normal range.

In embodiments, instead of using low-normal and high-normal ranges, a first histogram for the entire normal range plus a second one just for high-normal could also function. In this case additional processing could be applied if the Y seconds have an average heart rate in the high-normal range to double check that the event is not a result of demand ischemia. This processing could be a follow-on comparison to the high-normal thresholds or an increase in $N_{EA}$.

In embodiments, use of both positive and negative thresholds for high-normal $T_{H+}$ is not needed so that only a separate negative threshold $T_{H-}$ would be used and positive excessive ST shift detection thresholds would have one for the entire normal range.

In embodiments, to reduce the likelihood of repeating false alarms in the upper range of normal heart rates or for cases where the patient's heart rate is going back and forth from the normal to first elevated ranges one could either adjust down the upper limit for the normal heart rate range or increase the number of consecutive segments needed to alarm. For example, if the number is 3, increasing it to 5, 6, or 7 that is set by the ACMS physician's programmer 140 of FIG. 3 for specific cases where the patient has demand ischemia related false positive events. It might be adjusted for positive and negative shift events or only for positive or only for negative.

While the embodiments described herein have been directed at a stand-alone monitoring device, all of the capabilities are envisioned for use in therapeutic implanted medical devices such as drug pacemakers, cardioverters, ICDs and drug pumps and many of the features including those related to heart rate monitoring would be applicable to loop recorders, Holter monitors and other heart rate monitoring devices.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A method for actuating an alarm responsive to detection of excessive ST shift from a heart signal of a patient comprising:
   (a) attaching electrodes connected to electronic circuitry devoid of circuitry adapted to deliver electrical energy through the electrodes to the patient's heart, the circuitry adapted to process the patient's heart signal;
   (b) measuring for each beat of a multiplicity of beats from a PQRST representation of said heart signal during a data collection time period, the ST deviation being substantially an ST segment average voltage minus a PQ segment average voltage within each of said beats;
   (c) creating and storing in a processor at least one histogram comprising a set of bins, each of said bins being associated with an ST deviation range, wherein each bin contains a running count of the number of beats whose ST deviation is measured to be within the ST deviation range associated with the bin during one data collection time period;
   (d) initially independently only calculating either a positive or negative excessive ST deviation threshold in said at least one histogram;
   (e) sequentially operating said processor to calculate only said positive or negative ST excessive deviation threshold which has not been calculated in step (d) in said at least one histogram; and,
   (f) alerting said patient when at least one of the multiplicity of beats within said at least one histogram has an ST shift that exceeds at least one of said positive or negative excessive ST shift detection thresholds.

2. The method of claim 1 wherein two or more histograms over two or more data collection time periods are combined into a combined histogram for the calculations of steps c and d.

3. The method of claim 1 wherein the running count of beats stored within bins of said histogram are restricted to beats with an R-R interval range.

4. The method of claim 3 wherein there are multiple histograms each corresponding to a different R-R interval range.

5. The method of claim 1 where the method for calculating the positive detection threshold for excessive ST shift in step (c) comprises creating a positive mirrored histogram by the steps of:
   (a) replacing the counts in the bins corresponding to negative ST deviation values in the at least one histogram with a mirror of the counts in the bins corresponding to positive ST deviation values,
   (b) computing the standard deviation value for the positive mirrored histogram,
   (c) calculating an average heart signal amplitude for the data collection time period,
   (d) calculating a positive ST deviation threshold by multiplying the standard deviation for the positive mirrored histogram by a positive threshold preset multiplier value, and
   (e) calculating the positive excessive ST shift detection threshold as the positive ST deviation threshold normalized to the average heart signal amplitude.

6. The method of claim 5 where the positive ST deviation threshold preset multiplier value is an integer greater than or equal to 1.

7. The method of claim 1 where the method for calculating the negative detection threshold for excessive ST shift comprises creating a negative mirrored histogram by the steps of:
   (a) replacing the counts in the bins corresponding to positive ST deviation values in the at least one histogram with a mirror of the counts in the bins corresponding to negative ST deviation values,
   (b) computing the standard deviation value for the negative mirrored histogram, and
   (c) calculating an average heart signal amplitude for the data collection time period,
   (d) calculating a negative ST deviation threshold by multiplying the standard deviation for the positive mirrored histogram by a negative threshold preset multiplier value, and
   (e) calculating the negative excessive ST shift detection threshold as the negative ST deviation threshold normalized to the average heart signal amplitude.

8. The method of claim 7 where the negative ST deviation threshold preset multiplier value is an integer greater than or equal to 1.

9. The method of claim 7 wherein the average heart signal amplitude is calculated from one of the following: the average R-Wave amplitude of a multiplicity of beats or the average QRS amplitude of a multiplicity of beats.

10. The method of claim 9 wherein the normalization is calculated as a percentage of the average heart signal amplitude.

11. The method of claim 1 wherein the data collection time period is at least 6 hours.

12. A system for alerting patients to a potential heart attack by identification of excessive ST shift from the heart signal of a human patient, the system comprising:
at least two electrodes for sensing beats of the electrical signal from the patient's heart
a patient alerting mechanism;
electronics devoid of circuitry adapted to deliver electrical energy through the electrodes to the patient's heart connected to the at least two electrodes including a processor with associated digital memory adapted to compute the values of the ST deviation and ST shift being the change in ST deviation compared to baseline normalized to the baseline heart signal amplitude for a multiplicity of beats sensed by the at least two electrodes;
the processor adapted to save in memory the values of ST deviation for a pre-set data collection time period, the data providing the distribution of ST deviation over the data collection time period, an ST deviation distribution having a mean, a median, a positive standard deviation and a negative standard deviation, the positive standard deviation computed by creating a first symmetric distribution by mirroring the positive values of the ST deviation distribution about a central value selected from the group consisting of: mean of the distribution, median of the distribution, and zero ST deviation value;
the negative standard deviation computed by creating a second symmetric distribution by mirroring the negative values of the ST deviation distribution about a central value selected from the group consisting of: mean of the distribution, median of the distribution, and zero ST deviation value;
the system further adapted to calculate positive and negative ST deviation thresholds, the positive ST deviation threshold being the central value of a histogram of the ST deviation distribution plus at least two positive standard deviations, the negative ST deviation threshold being the central value of a histogram of the ST deviation distribution minus at least two negative standard deviations,
the system further adapted to calculate positive and negative excessive ST shift detection thresholds as the respective positive and negative ST deviation thresholds normalized to an average heart signal amplitude captured during the data collection time period,
the processor further adapted to activate the patient alerting mechanism based on either the positive or negative excessive ST shift detection thresholds being exceeded by the ST shift for a multiplicity of beats of the patient's heart signal.

13. The system of claim 12 wherein the average heart signal amplitude is based on the QRS amplitude of the multiplicity of beats.

14. The system of claim 12 wherein the normalization to the average heart signal amplitude results is calculated to be the ST deviation as a percentage of the average heart signal voltage amplitude.

15. The system of claim 12 wherein the average heart signal amplitude is based on the average R-wave amplitude of the multiplicity of beats.

16. The system of claim 15 wherein the normalization to the R-Wave voltage amplitude results is calculated to be the ST deviation as a percentage of the R-Wave voltage amplitude.

17. The system of claim 12 wherein a memory is within an implantable device.

18. The system of claim 17 wherein the excessive ST shift detection thresholds are calculated by the implantable device.

19. The system of claim 12 wherein the electronics are part of an implantable device with wireless data communication capability.

20. The system of claim 19 further including a physician's programmer having wireless data communication capability for receiving histogram data collected by the implantable device.

21. The system of claim 20 wherein the calculation of positive and negative excessive ST shift detection thresholds is performed by the physician's programmer and transmitted wirelessly to the implanted device.

22. A system for actuating an alarm responsive to detection of excessive ST shift from a heart signal of a patient comprising:
at least two electrodes for sensing beats of the electrical signal from the patient's heart
a patient alerting mechanism;
electronics devoid of circuitry adapted to deliver electrical energy through the electrodes to the patient's heart connected to the at least two electrodes including a processor with associated digital memory adapted to compute the value of the ST deviation for each beat of a multiplicity of beats from a PQRST representation of said heart signal during a data collection time period, the ST deviation being substantially an ST segment average voltage minus a PQ segment average voltage within each of said beats;
the processor further adapted to create and store in digital memory at least one histogram comprising a set of bins, each of said bins being associated with an ST deviation range, wherein each bin contains a running count of the number of beats whose ST deviation is measured to be within the ST deviation range associated with the bin during one data collection time period;
the system further adapted to calculate a positive excessive ST shift detection threshold by processing the data from the at least one histogram associated only with an ST deviation greater or equal to zero;
the system further adapted to calculate a negative excessive ST shift detection threshold by processing the data from the at least one histogram associated only with an ST deviation less than or equal to zero; and,
the processor being adapted to activate the patient alerting mechanism when at least one of the multiplicity of beats has an ST shift that exceeds at least one of said positive or negative ST shift detection thresholds.

23. The system of claim 22 wherein the patient alerting mechanism is selected from the group of:
(a) a vibrator
(b) an acoustic transducer
(c) a visual display.

24. The system of claim 22 wherein the processor and digital memory are contained in an implantable device.

25. The system of claim 24 wherein system includes a physician's programmer and both the implantable device and physician's programmer have wireless communications capability that enables transmission of the data from at the least one histogram stored in digital memory of the implantable device to the physician's programmer.

26. The system of claim 25 wherein the system calculation of positive and negative excessive ST shift detection thresholds is performed by the physician's programmer and said thresholds are subsequently downloaded back to the implantable device using the wireless communications capability of the implantable device and physician's programmer.

27. The system of claim 22 wherein two or more histograms over two or more data collection time periods are combined into a combined histogram for the calculation of positive or negative excessive ST shift thresholds.

28. The system of claim 22 wherein the running count of beats stored within bins of said histogram are restricted to beats with an R-R interval range.

29. The system of claim 28 wherein there are multiple histograms each corresponding to a different R-R interval range.

30. The system of claim 22 wherein the system is adapted to calculate the negative excessive ST shift detection threshold from the counts within a subset of the histogram bins, the subset being only the bins corresponding to ST deviation values less than or equal to zero.

* * * * *